US007937132B2

(12) United States Patent
Piron et al.

(10) Patent No.: US 7,937,132 B2
(45) Date of Patent: May 3, 2011

(54) HYBRID IMAGING METHOD TO MONITOR MEDICAL DEVICE DELIVERY AND PATIENT SUPPORT FOR USE IN METHOD

(75) Inventors: Cameron Anthony Piron, Toronto (CA); Christopher Alexander Luginbuhl, Toronto (CA); Donald B. Plewes, Toronto (CA)

(73) Assignee: Sunnybrook Health Sciences Center, Toronto, Ontario (CA)

( * ) Notice: Subject to any disclaimer, the term of this patent is extended or adjusted under 35 U.S.C. 154(b) by 0 days.

(21) Appl. No.: 12/031,271

(22) Filed: Feb. 14, 2008

(65) Prior Publication Data
US 2008/0132785 A1 Jun. 5, 2008

Related U.S. Application Data

(63) Continuation of application No. 10/916,738, filed on Aug. 12, 2004, now Pat. No. 7,379,769.

(60) Provisional application No. 60/506,784, filed on Sep. 30, 2003.

(51) Int. Cl.
*A61B 5/05* (2006.01)
(52) U.S. Cl. .................................. 600/415; 5/601; 5/600
(58) Field of Classification Search .................. 600/407, 600/437, 434, 415; 606/130; 5/600, 601, 5/615
See application file for complete search history.

(56) References Cited

U.S. PATENT DOCUMENTS

| 4,503,844 A | 3/1985 | Siczek |
| 4,552,346 A | 11/1985 | Schnelle et al. |
| 4,572,203 A | 2/1986 | Feinstein |
| 4,825,162 A | 4/1989 | Roemer et al. |
| 4,930,516 A | 6/1990 | Alfano et al. |
| 4,943,986 A | 7/1990 | Barbarisi |
| 4,989,608 A | 2/1991 | Ratner |
| 5,154,179 A | 10/1992 | Ratner |

(Continued)

FOREIGN PATENT DOCUMENTS

EP 0396866 11/1990
(Continued)

OTHER PUBLICATIONS

Gregory Palmer, et al, "Optimal Method for Fluorescence and Diffuse Reflectance Measurements of Tissue Biopsy Samples," Lasers in Surgery and Medicine, 30:191-200 (2002).

(Continued)

*Primary Examiner* — Brian Casler
*Assistant Examiner* — Joel M Lamprecht
(74) *Attorney, Agent, or Firm* — Quarles & Brady LLP

(57) ABSTRACT

This invention discloses a method and apparatus to deliver medical devices to targeted locations within human tissues using imaging data. The method enables the target location to be obtained from one imaging system, followed by the use of a second imaging system to verify the final position of the device. In particular, the invention discloses a method based on the initial identification of tissue targets using MR imaging, followed by the use of ultrasound imaging to verify and monitor accurate needle positioning. The invention can be used for acquiring biopsy samples to determine the grade and stage of cancer in various tissues including the brain, breast, abdomen, spine, liver, and kidney. The method is also useful for delivery of markers to a specific site to facilitate surgical removal of diseased tissue, or for the targeted delivery of applicators that destroy diseased tissues in-situ.

22 Claims, 35 Drawing Sheets

U.S. PATENT DOCUMENTS

| | | | |
|---|---|---|---|
| 5,426,685 A | 6/1995 | Pellegrino et al. | |
| 5,548,218 A | 8/1996 | Lu | |
| 5,590,653 A | 1/1997 | Aida et al. | |
| 5,590,655 A | 1/1997 | Hussman | |
| 5,594,337 A | 1/1997 | Boskamp | |
| 5,678,549 A | 10/1997 | Heywang-Koebrunner et al. | |
| 5,682,098 A | 10/1997 | Vij | |
| 5,682,890 A | 11/1997 | Kormos et al. | |
| 5,706,812 A | 1/1998 | Strenk et al. | |
| 5,744,958 A | 4/1998 | Werne | |
| 5,782,764 A | 7/1998 | Werne | |
| 5,855,554 A | 1/1999 | Schneider et al. | |
| 5,868,673 A | 2/1999 | Vesely | |
| 5,868,757 A | 2/1999 | Koutrouvelis | |
| 5,944,023 A | 8/1999 | Johnson et al. | |
| 6,066,102 A | 5/2000 | Townsend et al. | |
| 6,091,985 A | 7/2000 | Alfano et al. | |
| 6,159,221 A | 12/2000 | Chakeres | |
| 6,163,717 A | 12/2000 | Su | |
| 6,174,291 B1 | 1/2001 | McMahon et al. | |
| 6,201,392 B1 | 3/2001 | Anderson et al. | |
| 6,295,671 B1 | 10/2001 | Reesby et al. | |
| 6,298,506 B1 | 10/2001 | Heinold et al. | |
| 6,302,579 B1 | 10/2001 | Meyer | |
| 6,421,553 B1 | 7/2002 | Costa et al. | |
| 6,437,567 B1 | 8/2002 | Schenck et al. | |
| 6,446,286 B1 | 9/2002 | Karmalawy | |
| 6,459,923 B1 | 10/2002 | Plewes et al. | |
| 6,498,489 B1 | 12/2002 | Vij | |
| 6,521,209 B1 | 2/2003 | Meade et al. | |
| 6,526,299 B2 | 2/2003 | Pickard | |
| 6,593,101 B2 | 7/2003 | Richards-Kortum et al. | |
| 6,639,406 B1 | 10/2003 | Boskamp et al. | |
| 6,640,364 B1 | 11/2003 | Josephson | |
| 6,675,037 B1 | 1/2004 | Tsekos | |
| 6,697,652 B2 | 2/2004 | Georgakoudi et al. | |
| 6,723,303 B1 | 4/2004 | Quay | |
| 6,806,711 B2 | 10/2004 | Reykowski | |
| 6,822,450 B2 | 11/2004 | Klinge et al. | |
| 6,867,593 B2 | 3/2005 | Menon et al. | |
| 6,904,305 B2 | 6/2005 | Tsekos | |
| 7,023,209 B2 | 4/2006 | Zhang et al. | |
| 7,379,769 B2 | 5/2008 | Piron et al. | |
| 2001/0039378 A1 | 11/2001 | Lampman et al. | |
| 2002/0056161 A1 | 5/2002 | Falbo | |
| 2002/0073717 A1 | 6/2002 | Dean | |
| 2002/0099264 A1 | 7/2002 | Fontenot | |
| 2002/0131551 A1* | 9/2002 | Johnson et al. | 378/62 |
| 2002/0156365 A1 | 10/2002 | Tsekos | |
| 2002/0164810 A1 | 11/2002 | Dukor et al. | |
| 2002/0180442 A1 | 12/2002 | Vij | |
| 2002/0193815 A1 | 12/2002 | Foerster | |
| 2003/0007598 A1 | 1/2003 | Wang | |
| 2003/0191397 A1 | 10/2003 | Webb et al. | |
| 2003/0194050 A1* | 10/2003 | Eberhard et al. | 378/37 |
| 2003/0199753 A1 | 10/2003 | Hibner et al. | |
| 2003/0199754 A1* | 10/2003 | Hibner et al. | 600/411 |
| 2003/0206019 A1 | 11/2003 | Boskamp et al. | |
| 2004/0183534 A1 | 9/2004 | Chan et al. | |
| 2005/0104591 A1 | 5/2005 | Qu et al. | |
| 2005/0228267 A1 | 10/2005 | Bulkes et al. | |
| 2006/0133580 A1 | 6/2006 | Vezina | |
| 2008/0077005 A1 | 3/2008 | Piron et al. | |

FOREIGN PATENT DOCUMENTS

| | | |
|---|---|---|
| EP | 0753758 | 1/1997 |
| WO | WO 01/28412 | 4/2001 |
| WO | WO 02/39135 | 5/2002 |

OTHER PUBLICATIONS

Nicole Kline, et al., "Raman Chemical Imaging of Breast Tissue," Journal of Raman Spectroscopy, vol. 28, 119-124 (1997).

Ramasamy Manoharan, et al., "Histochemical Analysis of Biological Tissues using Raman Spectroscopy," Spectrochimica Acta Part A.52 (1996) 215-249.

K.E. Shafer-Peltier, et al., "Raman Microspectroscopic Model of Human Breast Tissue: Implications for Breast Cancer Diagnosis in Vivo," Journal of Raman Spectroscopy, 2002, 33:552-563.

Ntziachrstos V., et al., "Concurrent MRI and Diffuse Optical Tomography of Breast After Indocyanine Green Enhancement," PNAS, Mar. 14, 2000, vol. 97, No. 6, 2767-2772.

Cameron A. Piron, "Hybrid Imaging Guidance System for Biopsy of the Breast," thesis paper, University of Toronto, 2001.

Buadu LD, Murakami, J, Murayama S., et al., "Breast Lesions: Correlation of Contrast Medium Enhancement Patterns on MR Images with Histophathological Findings and Tumor Angiogenesis," Radiology 1996, 200:639-649.

M. Kriege, C.T.M. Brekelmans, C. Boetes, J. Klijn, et al., "Efficacy of MRI and Mammography for Breast-Cancer Screening in Women with a Familial or Genetic Predisposition," N Engl J Med 2004; 351:427-437.

Non-Final Office Action mailed Feb. 9, 2007 in U.S. Appl. No. 10/916,738.

Response to Feb. 9, 2007 Office Action in U.S. Appl. No. 10/916,738, Jul. 11, 2007.

Non-Final Office Action mailed Sep. 24, 2007 in U.S. Appl. No. 10/916,738.

Response to Sep. 24, 2007 Office Action in U.S. Appl. No. 10/916,738, Dec. 26, 2007.

Non-Final Office Action emailed Nov. 16, 2009 in U.S. Appl. No. 11/442,944.

Response to Nov. 16, 2009 Office Action in U.S. Appl. No. 11/442,944, May 17, 2010.

Non-Final Office Action mailed May 12, 2000 in U.S. Appl. No. 12/031,271.

Response to May 12, 2009 Office Action in U.S. Appl. No. 12/031,271, Nov. 12, 2009.

Final Office Action mailed Feb. 5, 2010 in U.S. Appl. No. 12/031,271.

Response to Feb. 5, 2010 Office Action in U.S. Appl. No. 12/031,271, Aug. 5, 2010.

Non-Final Office Action mailed Jan. 22, 2010 in U.S. Appl. No. 11/447,053.

Response to Jan. 22, 2010 Office Action in U.S. Appl. No. 11/447,053, Jul. 22, 2010.

International Search Report mailed Dec. 13, 2007 in International Application No. PCT/CA2007/001513.

International Preliminary Report on Patentability issued Mar. 3, 2009 in International Application No. PCT/CA2007/001513.

European Search Report mailed Jul. 30, 2009 in EP Application No. 09007010.3.

European Search Report mailed Oct. 10, 2009 in EP Application No. 09007010.3.

* cited by examiner

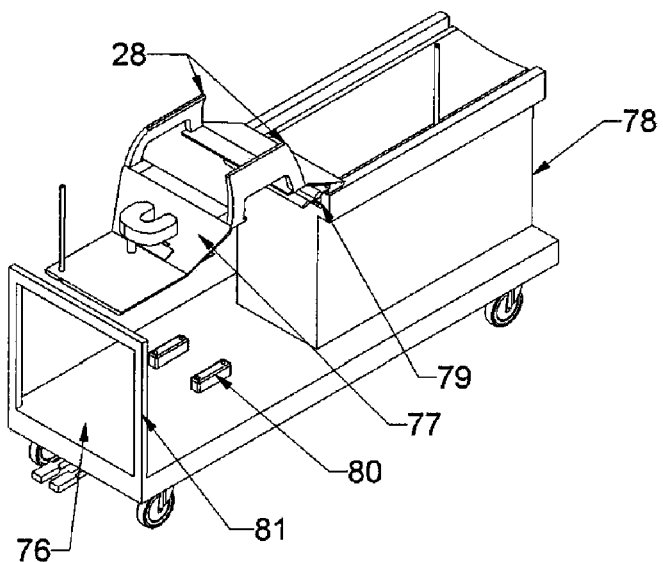
FIG. 4a
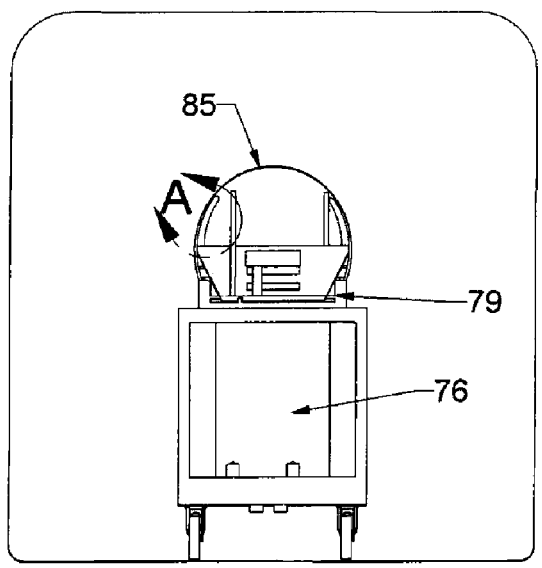
FIG. 4b
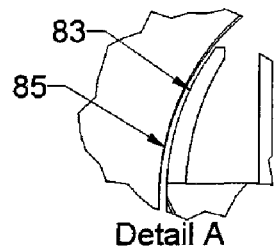
FIG. 4b1

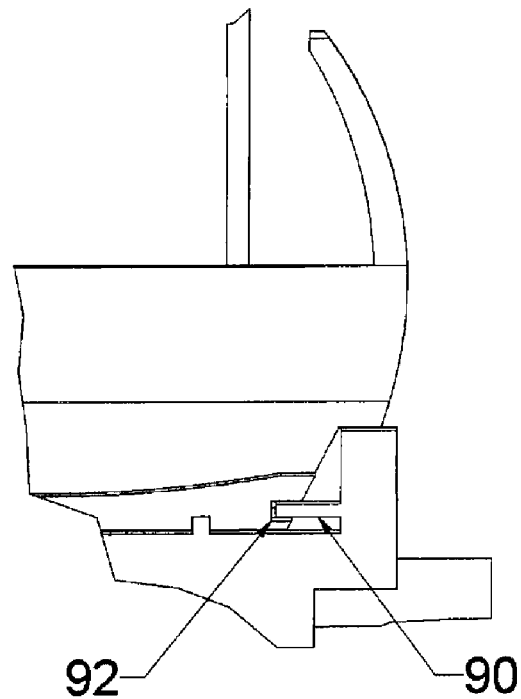
FIG. 4c1
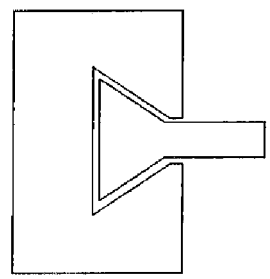
FIG. 4c2
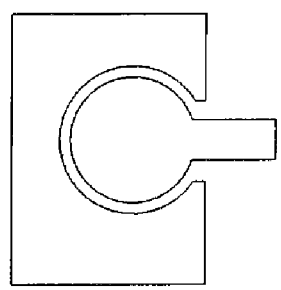
FIG. 4c3

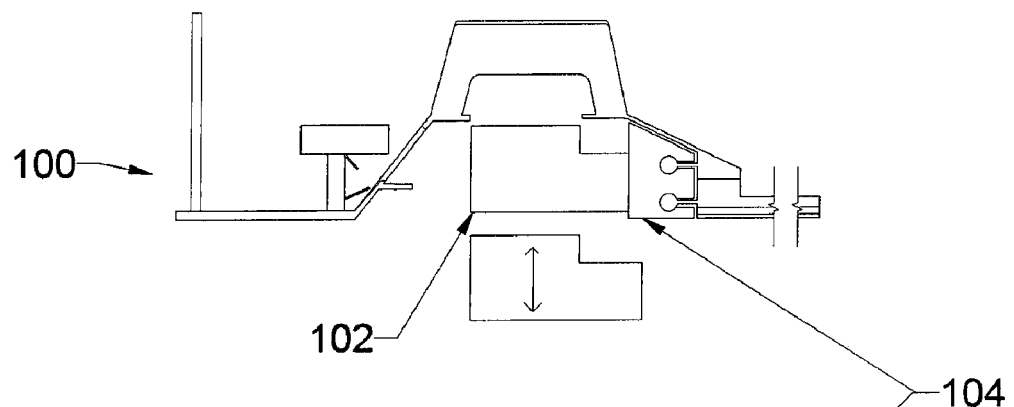
FIG. 5a1
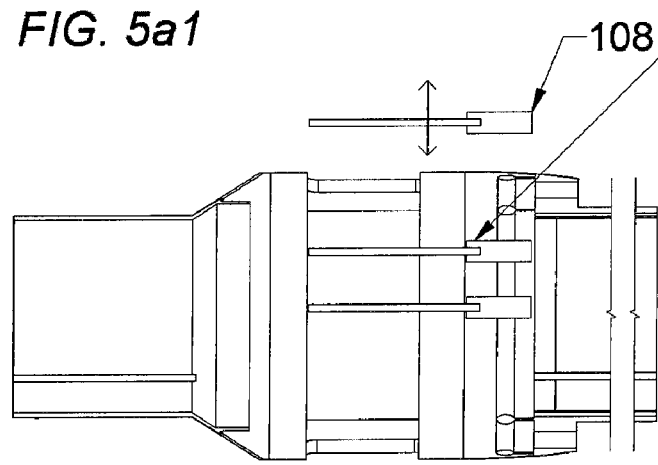
FIG. 5a2

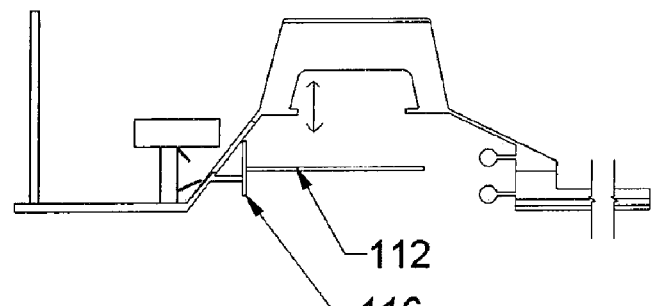
*FIG. 5b*
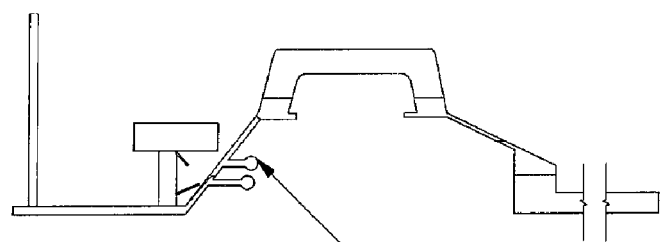
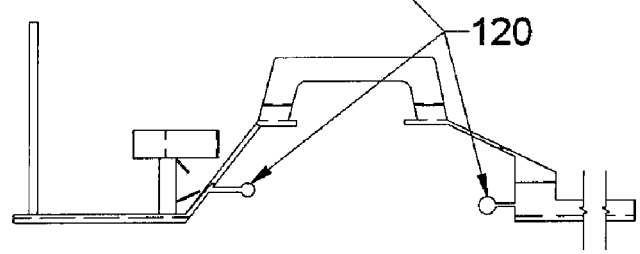
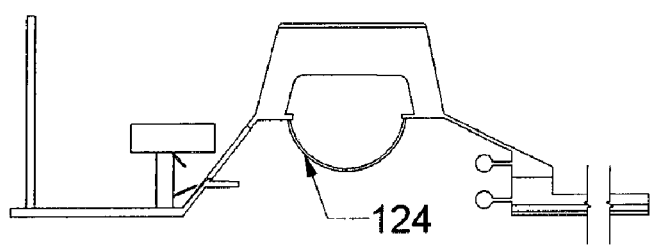
*FIG. 5c*

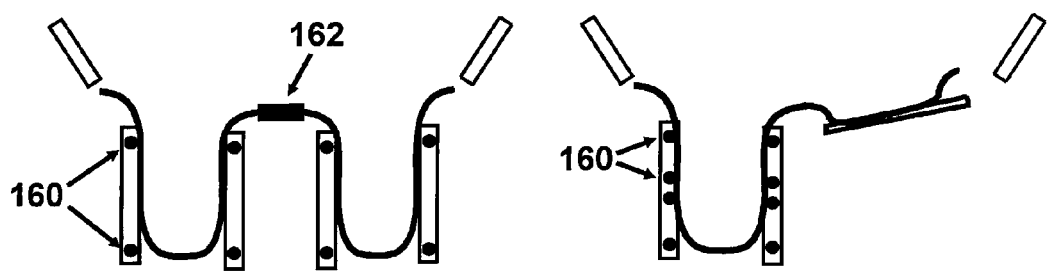
*FIG. 7a)*   *FIG. 7b)*
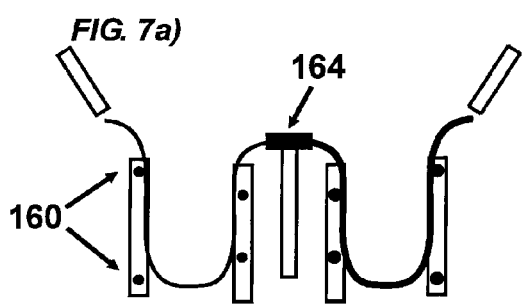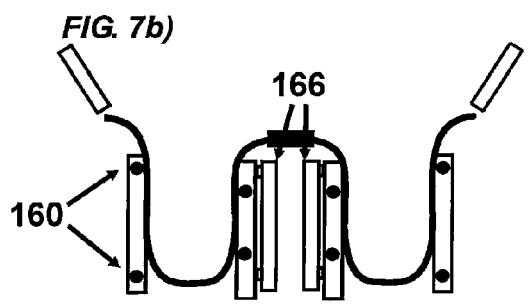
*FIG. 7c)*   *FIG. 7d)*
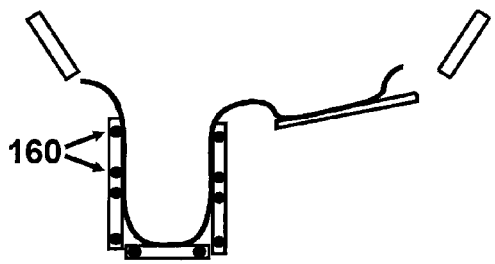
*FIG. 7e)*

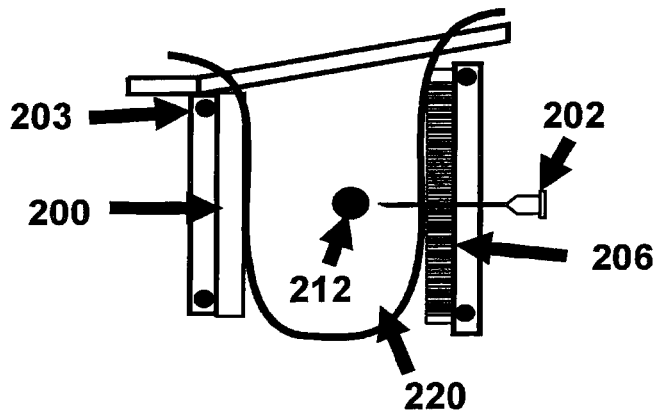
FIG. 9 a)
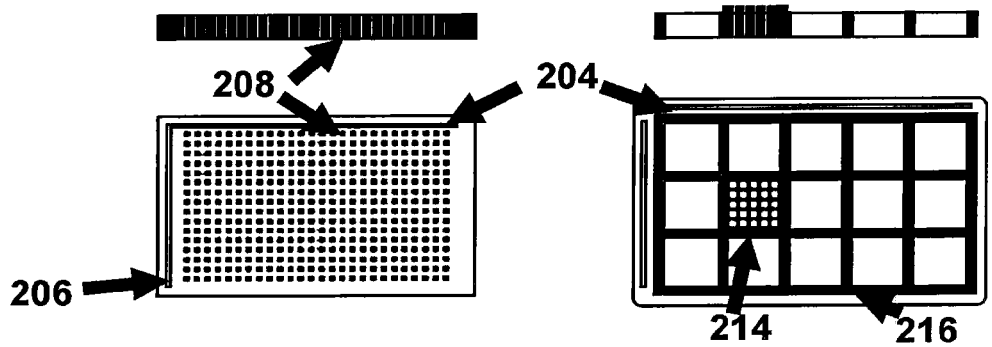
FIG. 9 b)         FIG. 9 c)
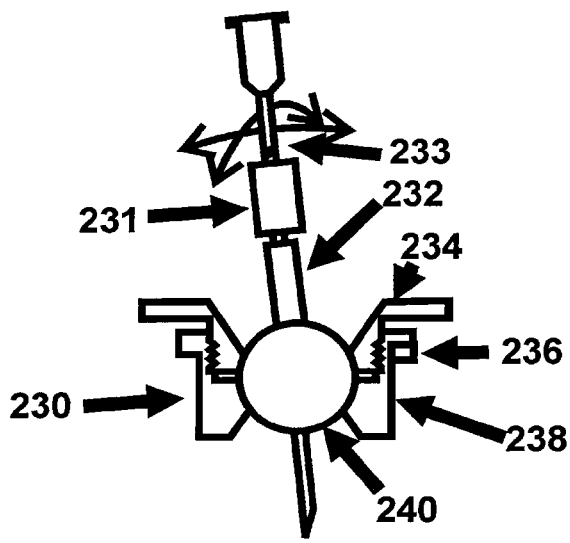 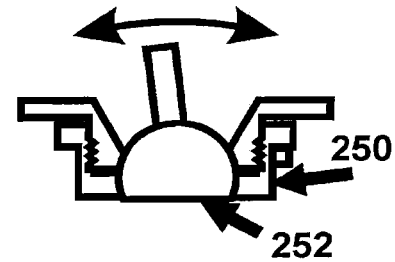
FIG. 10 a)         FIG. 10 b)

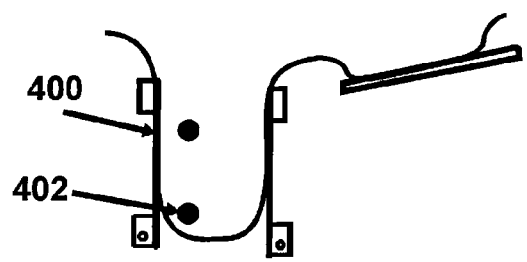 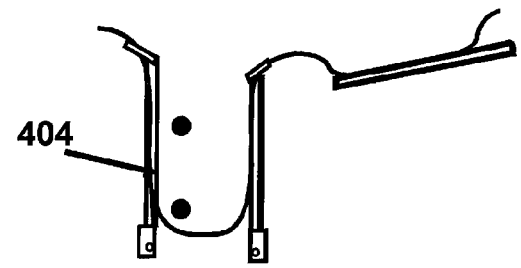
FIG. 19 a)  FIG. 19 b)
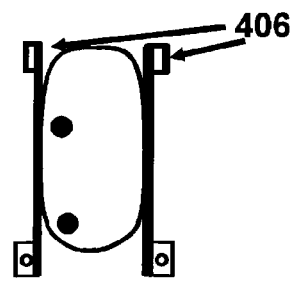 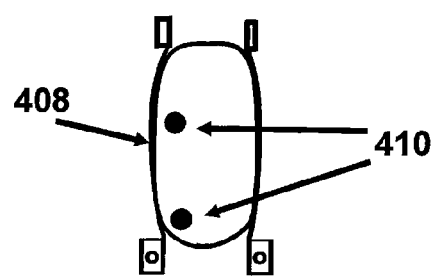
FIG. 19 c)  FIG. 19 d)

HYBRID IMAGING METHOD TO MONITOR MEDICAL DEVICE DELIVERY AND PATIENT SUPPORT FOR USE IN METHOD

CROSS-REFERENCE TO RELATED APPLICATION

This application is a continuation of U.S. patent application Ser. No. 10/916,738, filed Aug. 12, 2004 now U.S. Pat. No. 7,379,769, which claims the benefit of U.S. Provisional Application No. 60/506,784, filed Sep. 30, 2003.

STATEMENT CONCERNING FEDERALLY SPONSORED RESEARCH OR DEVELOPMENT

Not applicable.

FIELD OF THE INVENTION

This invention relates to the field of medical imaging and particularly to a hybrid imaging method and apparatus used to monitor and optimize the placement of interventional medical devices in human tissues.

BACKGROUND OF THE INVENTION

A number of techniques, methodologies, apparatus and systems have been proposed to improve the accuracy of instrumentality placement such as needle or catheter placement into tissue based on measurements from 3D imaging formats. These imaging formats (such as Magnetic Resonance Imaging, sonographs (ultrasound), fluoroscopy, X-ray, and the like) locate the needle entry device in relation to treatment- or therapy-targeted tissue, such as MR-detected target tissue. These imaging formats generate imaging data that are used to determine the appropriate positioning of the needle during treatment, which needle typically is placed in a guide device and moved into the tissue. In many cases, the needle is delivered solely on the basis of this imaging data information and confirmation of the final needle position relative to the target requires a second set of images to be acquired. In cases where tissue stiffness variations are extreme, the needle may deviate from the desired path and deflect on-route to the target tissue. Similarly, the needle may distort the tissue itself and thereby move the target tissue to a new location, such that the original targeting coordinates are no longer correct. Further limitations of current systems include the fact that needle position is often determined by reference to its artifact generated in the MR images. From this artifact, the operator infers the actual needle position relative to the target position. In many situations this is appropriate; however, when targeting small lesions (i.e. <7 mm), the needle artifact (often 5-9 mm) may obscure the target, limiting the ability to use even real-time imaging data, as from MRI, to validate needle/target position.

Numerous articles have been published in the medical literature describing imaging methods which can be used to monitor and optimize the placement of interventional medical devices in human tissues (e.g., Greenman et al, *Magnetic Resonance in Medicine*, vol. 39:108-115, 1998; Orel et al., *Radiology*, vol. 193, pp. 97-102, 1994; Kuhl et al., *Radiology*, vol. 204, pp. 667-675, 1997; Fischer et al., *Radiology*, vol. 192, pp. 272-272, 1994; Doler et al., *Radiology*, vol. 200, pp. 863-864, 1996; Fischer et al., *Radiology*, vol. 195, pp. 533-538, 1995; Daniel et al., *Radiology*, vol. 207, pp. 455-46, 1998; Heywang-Kobrunner et al., *European Radiology*, vol. 9, pp. 1656-1665, 1999; Liney et al., *Journal of Magnetic Resonance Imaging*, vol. 12, pp. 984-990, 2000; Schneider et al., *Journal of Magnetic Resonance Imaging*, vol. 14, pp. 243-253, 2001; Sittek et al., *Der Radiologe*, vol. 37, no. 9, pp 685-691, 1999; Jolesz, *Journal of Magnetic Resonance Imaging*, vol. 8, pp. 3-6, 1998; Lufkin et al., *Radiology*, vol. 197, pp. 16-18, 1995; Silverman et al., *Radiology*, vol. 197, pp. 175-181, 1995; Kaiser et al., *Investigative Radiology*, vol 35, no. 8, pp. 513-519, 2000; Tsekos et al., *Proceedings of the IEEE 2nd International Symposium on Bioinformatics and Bioengineering Conference*, 2001, pp. 201-208).

To address limitations described in the published prior art, a means to verify the actual trajectory of the needle is needed. A satisfactory method must be capable of observing the target tissue to ensure either that needle deflection or target tissue movements can be incorporated into the needle delivery path, thereby ensuring accurate needle delivery. Modified bore design MR magnet systems have been developed to provide more open access to the patient. As such, imaging and needle manipulation can take place concurrently with the physician having some access to the patient while the patient is positioned in the bore. However, these "open" systems are not always available and are often of suboptimal field strength, which can result in reduced image quality. Other proposed solutions in the art involve in-bore robotic devices that enable manipulation of the needle within the bore of the imaging magnet. While this approach usefully addresses the issues of tissue/needle deflection, it also removes the normally close interaction between the radiologist and patient, which may lead to high levels of patient anxiety.

SUMMARY OF THE INVENTION

The present technology provides a medical imaging system capable of various imaging and interventional tasks based on non-invasive detection, such as MR-detection, of diseased tissue, with many of these applications utilizing a hybrid imaging approach in combination with ultrasound imaging techniques. The apparatus and techniques disclosed are combined in a system capable of various imaging and interventional strategies that can be utilized for comprehensive treatment protocols, for example, complete breast cancer management. Typically, the devices are delivered through thin needles (ranging from 20 to 9 gauge sizes (0.81 mm-2.91 mm)) which may either place devices into the tissue or retrieve tissue from a specific anatomical region.

The present technology uses 3D imaging data obtained by conventional non-invasive imaging techniques, particularly MRI (magnetic resonance imaging), US (ultrasound), positron emission tomography (PET), computerized tomography (CT), or other three-dimensional imaging system. The technology discloses a number of imaging and interventional functions required for complete breast-MRI patient management, including screening for breast cancer, determination of tumor extent and multi-focality of previously diagnosed cancer, and diagnosis of suspicious lesions. Further applications of the technology include MR-guided positioning of wires and marking devices in the breast to facilitate any treatment or diagnostic procedure, such as those including but not limited to surgical excision/biopsy, MR-guided core biopsy for lesion diagnosis without surgery, and MR-guided and monitored minimally invasive therapy to destroy diseased tissue. Multimodality MR/US breast imaging disclosed in the descriptions of the present technology enables a more effective means of interventional device positioning (more accurate, faster, less invasive to the patient), a means of tissue diagnosis without biopsy (through ultrasound (referred to herein as "US examination"), and a means of monitoring tissue ablation boundaries when performing minimally invasive therapies.

While the method of the present technology was specifically optimized for breast cancer management, it will be understood by those of ordinary skill in the art that the techniques and apparatus of this technology can be easily adapted to various other body parts and pathologies.

One aspect of the present technology is to provide a patient physical support system, including patient support and transport stretcher that is designed in such a manner to enable maximum access to one or both breasts by the operator.

A second aspect of this technology is to provide a compression system with four or more independently movable plates designed to avoid interference with US examination transducer and biopsy needle delivery. "Four or more" may limit bilateral-only implementations A third aspect of the present technology is to provide a transport stretcher or gurney to aid patient access to the interventional area, the apparatus to include a bridged interventional gap, IV (intravenous) poles which accompany the patient during the entire procedure, a headrest which accommodates the patient's arms and permits a view out of the magnet, and mirrors and lighting to help better position the patient.

A fourth aspect of this technology is to provide breast compression plates with various apertures and fixtures to accommodate various MR imaging coils or other radio frequency devices, US examination-transparent imaging plates, device guide plugs with straight or/and angled orientations, a goniometer system for needle positioning, US examination transducer positioning system, and freehand transducer calibration system.

A fifth aspect of the present technology is to provide software to calculate needle trajectory based on fixed fiducial positions, to enable multiple targeting, and to determine a shortest distance to lesion.

A sixth aspect of this technology is to provide additional software to calculate angled needle trajectory based on fixed fiducial positions, to enable multiple targeting through multiple incisions, to enable multiple targeting though a single incision, to determine a shortest distance to lesion, and to determine any potential interference of needle handle with surrounding apparatus.

A seventh aspect of the present technology is to provide software for US examination transducer delivery based on fixed fiducial positions, to enable multiple targeting, to determine shortest imaging distances to lesion, to recalculate with transducer in two orientations, to recalculate with transducer at various angulated orientations, and to convert tracked transducer coordinates to corresponding stereotactic frame coordinates.

An eighth aspect of the present technology is to provide still additional software to convert MR-data, set scan plane and distance to target.

A ninth aspect of this technology is to provide additional software for various MR/US image co-registration, visualization, and image processing tasks

BRIEF DESCRIPTION OF THE DRAWINGS

FIG. 5 shows the plate locking/positioning system of the patient support and the related apparatus according to the invention. The compression plates can be moved anterior/posterior within the plate locking support. a illustrates how the compression plates/locking supports can be introduced from the side of the apparatus. Each plate can be moved independently and to any position in the left/right direction. b shows that additional compression plates in the superior/inferior direction can be accommodated so as to "box" the breast. c shows another aspect of the invention whereby various embodiments of rail positions are possible as well as flexible sling designs to compress the breast against the chest wall.

FIG. 7: shows various coil configurations that may be used according to the invention. a Bilateral imaging application with 4 coil array. b Unilateral imaging configuration with 4 coil array. c Bilateral imaging with 4 coil array. In order to minimize the interaction between the medial coils, their size has been reduced and one or more RF devices which operate to decouple the medial coils is introduced. These can be attached to sternum support or positioned by attaching to the plate locking/positioning system as shown in d. and e Additional coils may be incorporated at other positions such as within an anterior/posterior compression plate, or within the patient support structure.

FIG. 9 illustrates systems for breast biopsy disclosed in the prior art which are based on a pair of parallel compression plates to immobilize the breast and provide means to direct a needle to a lesion based on fiducial marker measurements made in the MR image.

FIG. 10a shows how a needle holder may be used according to the invention to allow arbitrary orientations of a needle for biopsy. After the correct orientation is achieved, the gimbal is locked in position by tightening the threaded clamp. By reducing the dimension of the gimbal as illustrated in b the point of rotation is positioned near the skin surface.

FIG. 19 illustrates some useful features of the US transparent compression frame according to the present invention. The thin, angled top support member helps support the patient and the U-shaped support frame enables full US imaging access to the breast. b, c and d show alternative embodiments of the US permeable membrane with many cut away openings.

Figure 1A:
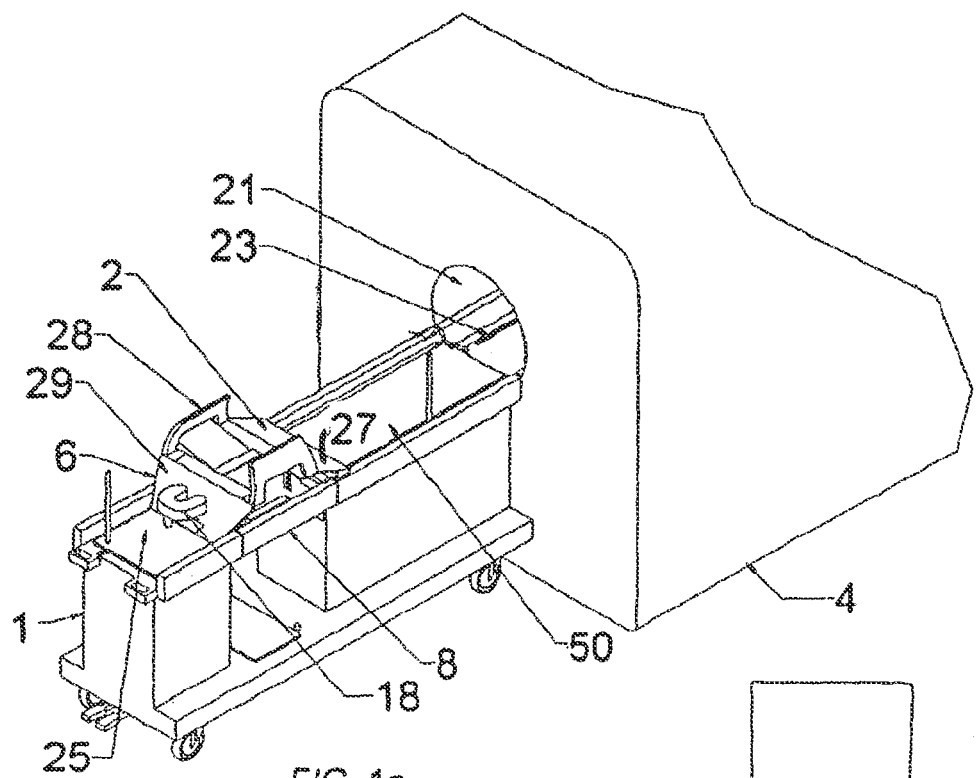
FIG. 1a shows the stretcher and patient support attached to the MR imaging system according to the invention; b is a side-view of the stretcher with patient in the 'arms back' position.

The foregoing features, objects and advantages of the present invention will be apparent to one generally skilled in the art upon consideration of the following detailed description of the invention.

DETAILED DESCRIPTION OF THE PREFERRED EMBODIMENT

The following described technology encompasses a hybrid imaging method to monitor the placement of interventional medical devices and apparatus that can be used in such an imaging method and other medical or therapeutic procedures. The preferred embodiments are described by reference to both the general and specific attributes and features of the components of the technology. However, this specification discloses only some specific embodiments as examples of the present technology, which are not intended to be limiting in the interpretation of the scope of the claimed invention of this patent. It will be readily apparent that variations and modifications may be effected without departing from the true spirit and scope of the novel concepts of the invention.

Patient Support Structure and Transport Stretcher

One of the areas of disclosure of this technology is a patient support and transport apparatus including a structure, gurney or transport stretcher 1 as indicated in FIG. 1, supporting a patient support structure 2. This patient transport stretcher 1 and table top patient support structure 2 act to support the patient 26 and to immobilize the breasts 36, while providing a transportation system for carrying the patient 26 to an MR imaging system 4, as well as providing a stretcher 1 and support structure 2 for the patient during imaging which can be attached and detached from the MR imaging system 4 and moved to other locations. The patient 26 lies on the patient support structure 2 in the prone position (face downward) and may be advanced feet first into the bore 21 of the MR imaging system 4. The patient's breasts 36 fall into an opening 19 at the chest level of the patient support structure 2 and then can be immobilized by compression plates (not shown in this FIG.) in a medial-lateral direction. According to the technology described herein, the patient support structure 2 has been designed to: 1) provide room for large breasts to extend into the access volume without touching the bottom of the magnet bore 21, 2) optimize room available for the patient in the magnet bore 21, 3) allow the patient's arms to be positioned forward above their head or at their sides, 4) provide access both medially and laterally to either breast, particularly towards the chest wall, 5) ensure devices with a wide ranges of oblique orientations have maximal access to all points within the breast, all with optimization for patient comfort. The design of the present apparatus thus serves a multitude of imaging and intervention functions, with very little adjustment of the components. Medial and lateral interventions and hybrid imaging interventions can be accomplished without prior knowledge of the approach required. The apparatus disclosed by the present invention is substantially different from systems currently available commercially, such as, for example, the equipment made by MRI Devices, and USA Instruments. Systems presented by Su (U.S. Pat. No. 6,163,717), Liney et al, "Bilateral Open Breast Coil and Compatible Intervention Device," Journal of Magnetic Resonance Imaging, 2000 are dual function breast imaging and intervention systems. These systems lay on the MRI bed with no modification to the normal stretcher's table top. As space is limited in an MRI magnet bore, the unmodified tabletop limits to space available for access to the breast and for the patient in the magnet. None of these systems are used for functions other than MR imaging or MRI-only interventions and require significant setup time in the MR imaging magnet to convert from an MR imaging to MR interventional system.

The concept of a specially designed patient support system and stretcher is not believed to have been presented in the prior art. Schneider et al, 2001, presented a modified MR stretcher for the purpose of MRI breast biopsy. This invention was also presented in U.S. Pat. No. 5,855,554. The top support surface was modified to enable more access to the breast, whereas the bottom part of the stretcher was not modified. Breast biopsy systems presented by S. H. Heywang-Kobrunner, 1999, Kuhl 1999, Fischer (U.S. Pat. No. 5,913,863), Cardwell (U.S. Pat. No. 6,423,076) all present modifications to the top surface as well, with no modification made to the stretcher component. These systems compromise MR imaging capability for improved access to the breast. No integrated system has been developed in an attempt to maximize access to the breast by modification of the tabletop and stretcher, and providing provisions to use the system for imaging, intervention and multiple modality functions. These concepts can be easily transferred to embodiments wherein the stretcher is a non-wheeled structure, or a stationary structure.

Figure 1B:
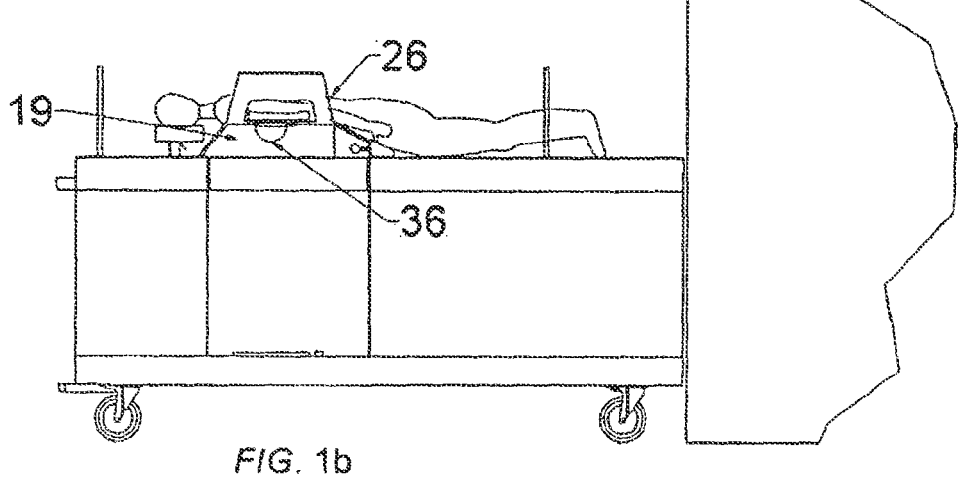
Figure 2A:
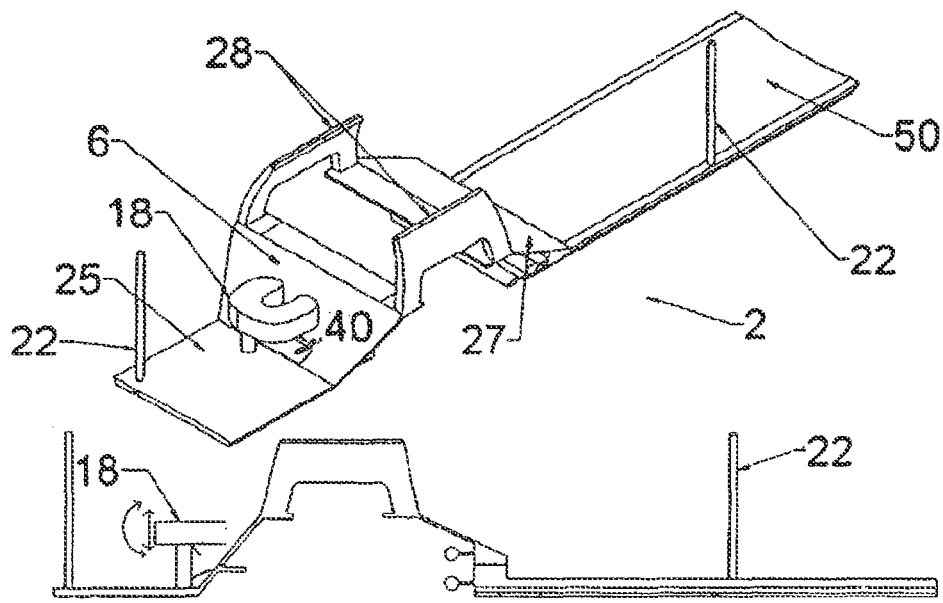
FIG. 2a shows the patient support structure without sternum or contralateral breast support. b shows the support structure with attached breast constraint and sternum support, which is angled so as to provide good medial access to the breast. c and d show the ability to access various positions in the breast with various interventional probe orientations with respect to the patient support structure and compression plates.

As shown further in FIGS. 1a, 1b and FIGS. 2a) and b), in an exemplary embodiment of the technology described herein, the patient support structure 2 consists of a winged structure with no medial or central structural members. There is a cervical (shoulders, neck and head) support area 6. The two arches 28 connect the head support 18 and arm support 25 (cervical section) to the lower patient support 50 (lumbar or thoracic section). The horizontal aspects of these arches 28 are positioned posterior to the patient's breasts so as to maximize access to the patient's breasts in a lateral approach. These arches 28 further provide a restraint for the patient's arms when they prefer to have their arms at their sides. Another feature of these arches 28 is to ensure a strong structural joint between the superior and inferior portions of the patient support structure 2. The arches can be made as large as needed to ensure the required strength and introducing a curved geometry to the arches ensures that the arches can be introduced into the MR imaging bore. In the extreme, these arches 28 could form a complete cylinder in which the patient would be placed to maximize the strength of the patient support. Double arch supports have not been presented as a means to provide the fundamental support or connectively between the cervical and thoracic sections of the apparatus.

The patient support structure 2 may ramp upward (inferior ramp 27) towards the opening 19, and may slope downward away from the opening 19 towards the head support 18 (superior ramp 29). The inferior ramp 27 positions the patient 26 so that her pendulant breasts will not touch the floor of the magnet bore 21, providing a large volume for interventional access. The superior ramp 29 (if present) provides a region for the patient's arms to rest when in the arms-forward position (arms above the head). The use of arching members as the primary structural component to the system, with or without a removable sternum support is unique. The geometry presented in FIG. 4, has been designed to provide structural support and patient support so as not to interfere with access to the breast.

The volume available for interventional access is maximized by the transport stretcher and the design of the table top patient support structure 2 to provide an angulated entry geometry to the lateral aspect of the breast volume but creating wide or tapered entry of the table structure toward the patient volume from the lateral aspects. The access provided by this arch design is illustrated in FIG. 2a) b), c), d). A bridge section 8 of the transport stretcher 1 provides support when the patient support structure 2 is being rolled into the magnet bore 21, but is designed to retract out of the way when the patient support structure 2 is fully removed from the magnet bore 21 for intervention. In one embodiment of this technology, a headrest 18 is situated at the superior end of the patient support structure 2, whose height and angle may be adjusted. Mirrors 40 may be provided below the headrest 18 to allow the patient 26 a right-side-up view out the front of the magnet. This feature of the technology is intended to reduce patient anxiety. The embodiment shown has a single telescoping headrest 18 which incorporates a tilting adjustment to maximize the room available at the superior end of the structure, and to permit adjustment and clamping of the headrest orientation with one hand. A simplistic headrest design has been presented by Schneider et al, 1999, however this design does not embody any additional features described above.

Figure 2B:
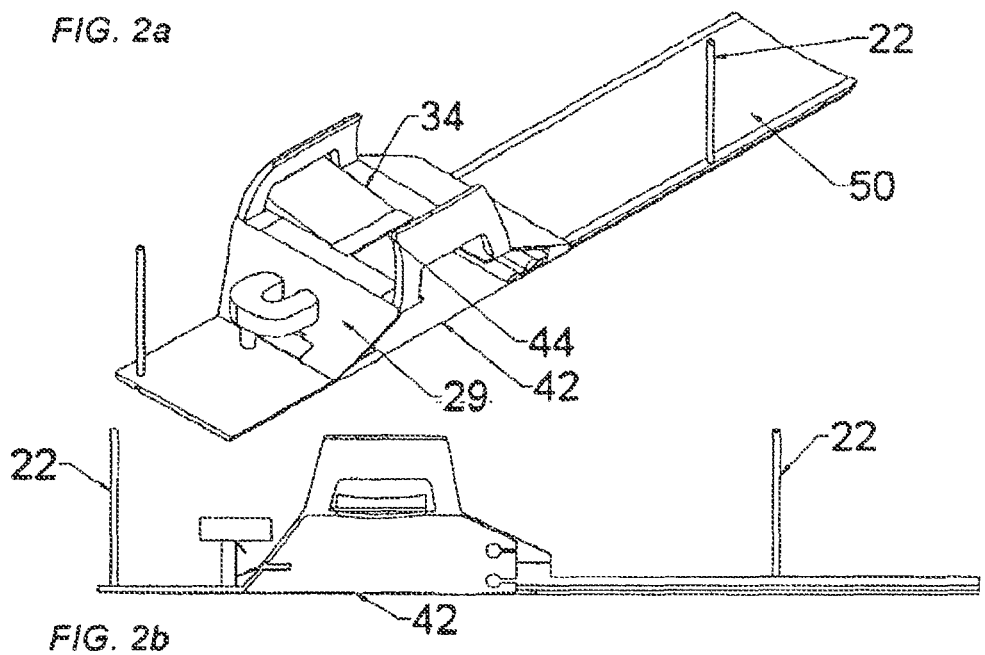

In further embodiments of the technology described herein, bridge members may be used to support the patient over the breast access volume, as shown in FIGS. 2a, b), c) and d). For applications involving both breasts (i.e., bilateral applications) a sternum support member (44 as shown in FIG. 2b)) may be used. For unilateral applications, a bridge member breast support 34 that supports the contralateral breast and compresses it against the chest wall is attached. Unlike the device described by Heywang-Kobrunner et al., "MR-Guided percutaneous excisional and incisional biopsy," European Radiology, vol. 9, pp. 1656-1665, 1999, in the present technology, the angle of this support optimizes medial access to the breast while supporting the patient in a comfortable position. Angulation of the breast support 34 (10-30 degrees) further provides improved access to the breast for medial access with an angulated device approach. The embodiment of a removable sternum support member 44 and contralateral breast support 34 maximizes access to the breast from medial and lateral aspects and is unique with respect to the prior art. Removal of the breast and sternum supports are indicated in FIGS. 2a) and b). This resulting improved angulation with a breast support 34 is demonstrated in FIG. 2c) with the needle approaching the breast beneath the contralateral breast support 34. Maintaining the sternum support member 44 in place would result in a limited angular access to the breast. Schneider et al, 2001 (E. Schneider, K. W. Rohling, M. D. Schnall, R. O. Giaquito, E. A. Morris, and D. Ballon, "An Apparatus for MR-Guided Breast Lesion Localization and Core Biopsy: Design and Preliminary Results," Journal of Magnetic Resonance Imaging, vol. 14, pp. 243-253, 2001) shows the top portion of the tabletop could be rotated to accommodate either left breast or right breast access. No attempt was made to improve access to the breast for imaging or interventional procedures as is provided by the system presented in this document by way of a unique patient support structure 2 and optionally removable sternum support member 44 and contralateral breast supports 34.

Figure 2C:
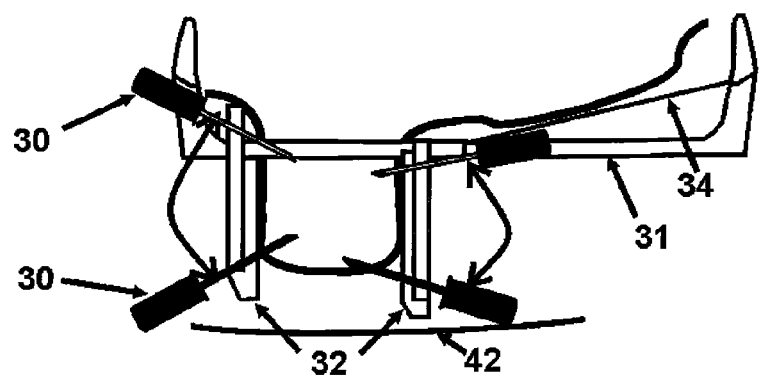
Figure 2D:
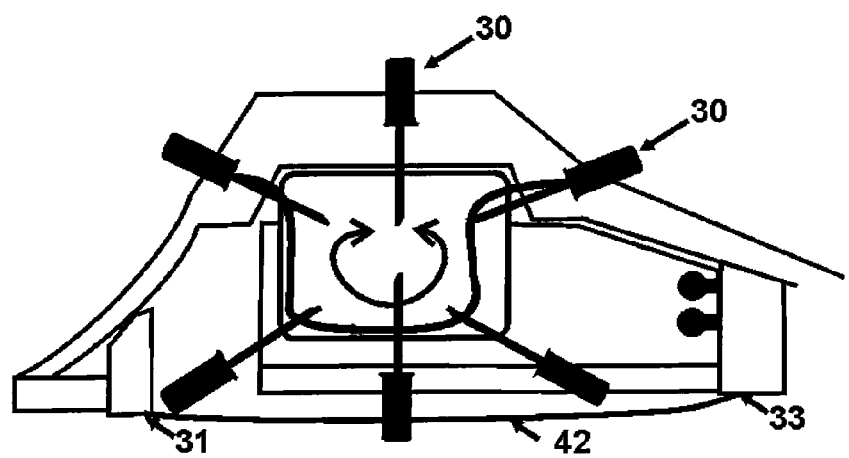

Another feature demonstrated in FIG. 2b and FIG. 2d is the addition of a disposable blood barrier 42 that is attached to the patient support structure 2. Features at the base of the thorax (thoracic) support 33 and the shoulder and neck (cervical) support 31 allow attachment of various blood catchments (plastic diapers). These can be easily attached and removed during the procedures. A further preferred embodiment shown in FIGS. 2a and b consists of IV poles 22 at the inferior and superior ends of the apparatus. These poles act to hold the saline drip during the breast procedures. No attempts have been made to implement any of these embodiments in the prior art.

FIGS. 2c and d shows a patient support structure with respect to interventional and imaging probe access. FIG. 2c (Front View) shows Interventional or imaging probes 30 may be introduced at various orientations to the breast from either medial or lateral directions. (Note: only a portion of the patient support structure 2 and compression plates 32 are shown in this view). Arrows indicate range of probe 30 positioning without interfering with apparatus infrastructure. FIG. 2d (Lateral view): Varied access of probes 30 is shown in a side view. Tapered geometry of patient bed (not shown) and positioning of compression plate 32 locking mechanisms and rail guides (not shown) far from a breast enables large angular and positional access. This tapered geometry extends to the medial aspect through a gradually sloped contra-lateral breast support 34.

Transport Stretcher

The transport stretcher 1 is used to transport the patient to and from the MR image 4r, to dock to the MR imager 4 such that the patient support structure 2 may be moved to advance the patient 26 into the magnet's bore 21, and as a table for the patient support structure 2 during interventional procedures and ultrasound (US) exams, which are performed away from the MR magnet's field (FIG. 1). The patient support structure 2 (e.g., FIG. 2a)) rolls on the guides of the transport stretcher 1 when advancing into the guides 23 in the bore 21. On the underside of the patient support structure 2 are a set of wheels (not shown). The cross-section of the patient support structure 2 corresponds to the internal geometry of the bore of the magnet. The transport stretcher 1 attaches (docks) to the connection mechanisms of the imaging system 4. The interlocks and safety mechanisms depend on the specific design of the MR imaging system 4. In order to have complete access to the breast when the patient 26 and the patient support structure 2, are removed from the magnet bore 21, a large section of the transport stretcher 1 can be retracted (FIG. 3a-d), leaving a large gap. In the method of this technology, this can be accomplished in a variety of ways as illustrated in FIG. 3a-d). The patient support structure 2 will be supported across this gap and not be in a full cantilever position at any time (i.e., wheels on patient support structure 2 will always be in contact with a surface on the transport stretcher 1 or MRI bore 21 when the patient support structure 2 is moving in or out of the bore 21). In order for this to be accomplished, there are a variety of embodiments. 1) A member (e.g., 56) that folds up from either the torso, or the head end of the stretcher., 2) A member (e.g., 72) that pulls out from under the torso end of the stretcher, 3) Two members (e.g., 68) that split apart and hinge out laterally. The gap 57 in the structure provides additional interventional volume. Additional embodiments may also include side walls 58 that match the geometry of the magnet. This provides the operator with a means of verification that needles extending from the breast will not hit the side of the magnet as the patient is returned into the magnet for any additional MRI scanning. As the large interventional access area is unique to this invention, mechanical provisions to enable use of this additional space without compromising patient safety, or complexity for the operator as presented in this document are unique with respect to the prior art.

Additional features of the stretcher may include a set of drawers in the side to organize all the secondary apparatus associated with the system. Further embodiments of this technology may include a set of lights 60 on the medial/lateral faces of the right and left sides of the breastand at the bottom of the gap in the stretcher. The orientations and intensities of these lights may be adjusted by the technician or radiologist. Another embodiment may be an adjustable mirror 62, or a mirror positioned on the lower part of the apparatus that allows the radiologist to more easily see the position of the nipple when the breast is compressed. This is a desirable feature in the method of the technology described herein, because the nipple is often used as an imaging landmark in the breast, and uneven compression may cause it to deviate either medially or laterally, thereby providing an unreliable landmark. These features of the present invention are shown in FIG. 3a-d.

Figure 3:
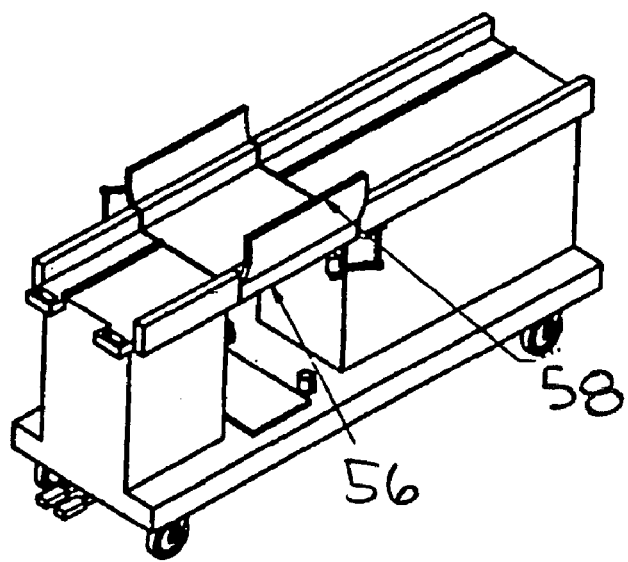
FIG. 3 shows the extra interventional volume provided by an opening in the stretcher according to the invention. a shows one aspect in which the member bridging the opening may fold down into the volume. b shows another aspect in which the member may roll under the patient support in the stretcher. c shows that the member may also break into multiple sections that may swing laterally and out of the way. d shows another aspect in which a portion of the patient support member may lower to provide an accessible volume. e shows another aspect in which the front and rear sections of the patient support raise in order to provide an accessible volume. f shows another aspect in which a slim support with a gap smaller than the support wheelbase distance ensures one wheel on the head end of the apparatus is always in contact. g Shows another aspect in which a bridge support that may move either to the right or left side allowing medial access to the breast while ensuring the wheels are in contact with the stretcher support surface h Alternatively, sections of the stretcher may be removed to permit increased access to the breast.
Figure 3A:
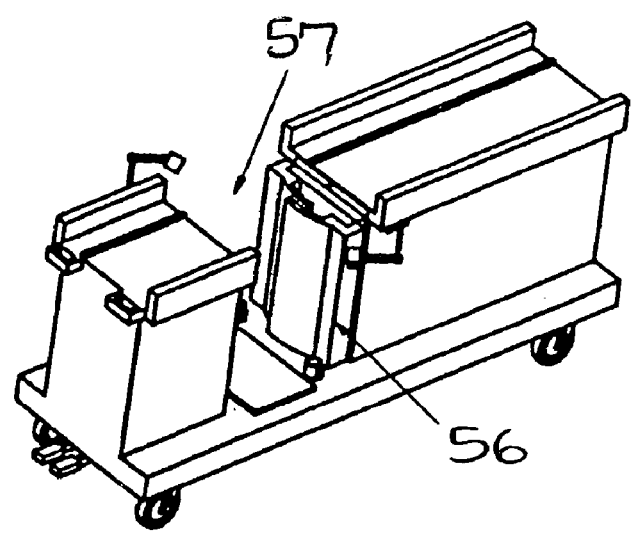
Figure 3B:
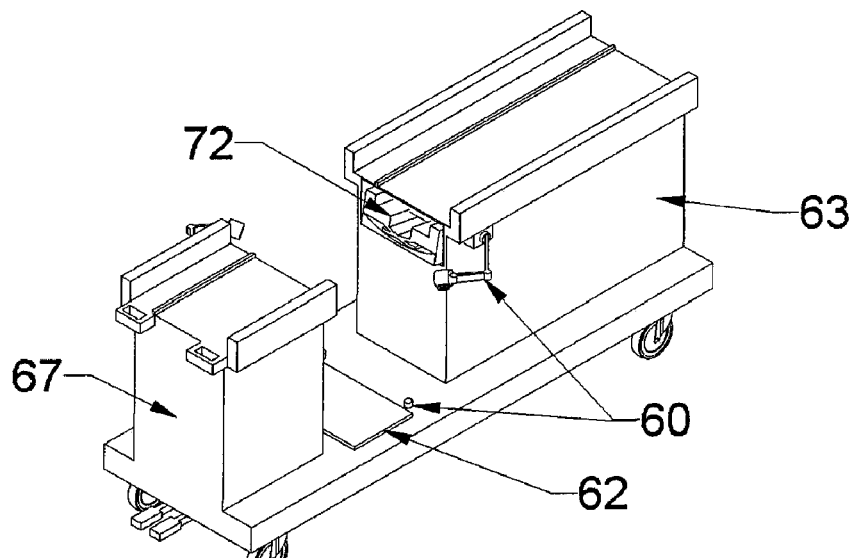
Figure 3C:
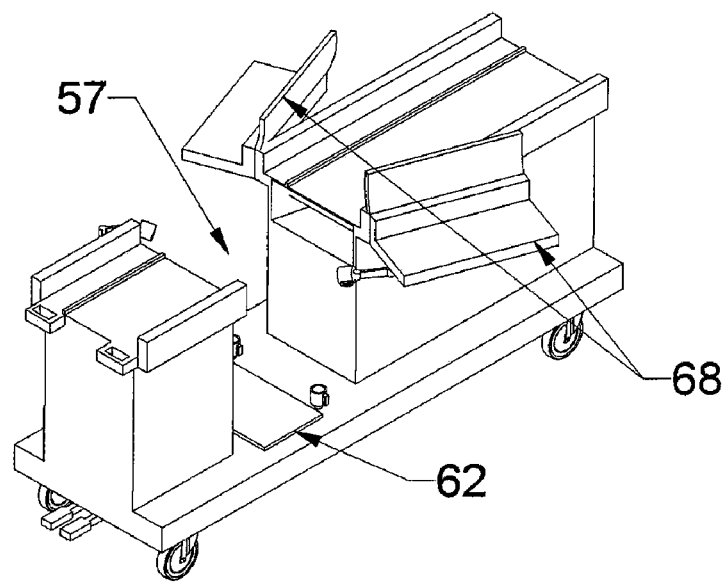
Figure 3D:
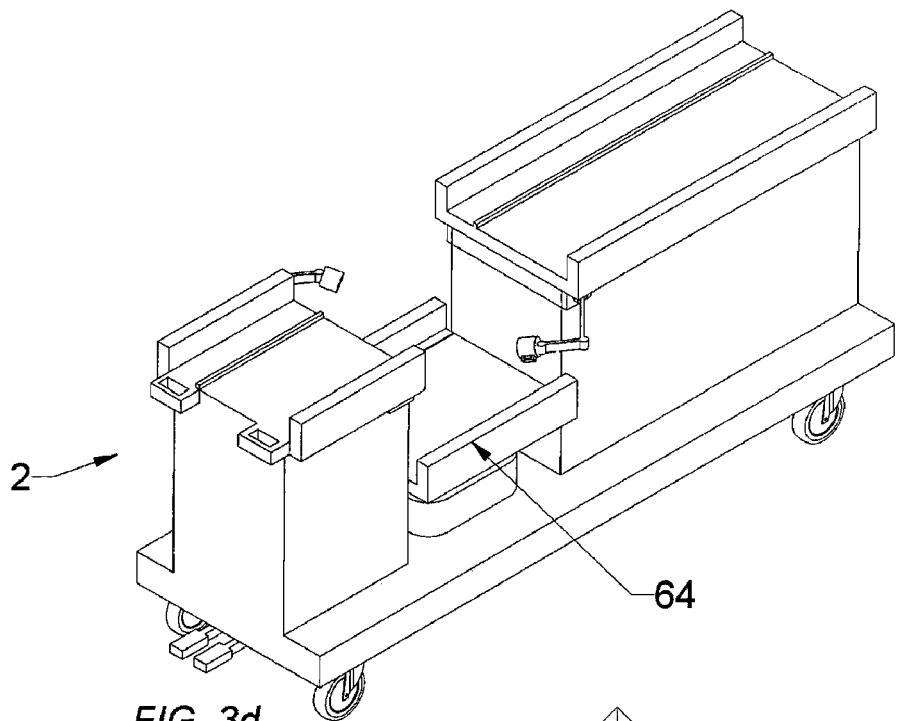

In FIG. 3 d, the stretcher is shown with the telescoping bridge 64 being elevated into support position.

Figure 3E:
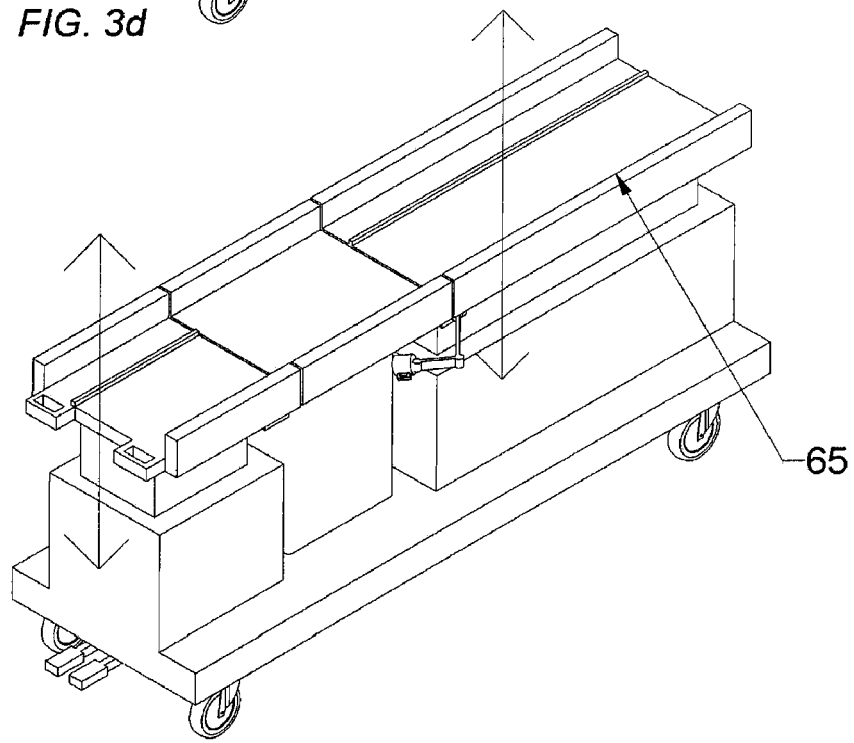

FIG. 3e shows that the entire stretcher, with the exception of the bridging 65 can be raised or lowered to provide a flat surface when advancing the patient support into the bore or to provide a gap facilitating device delivery and intervention.

Figure 3F:
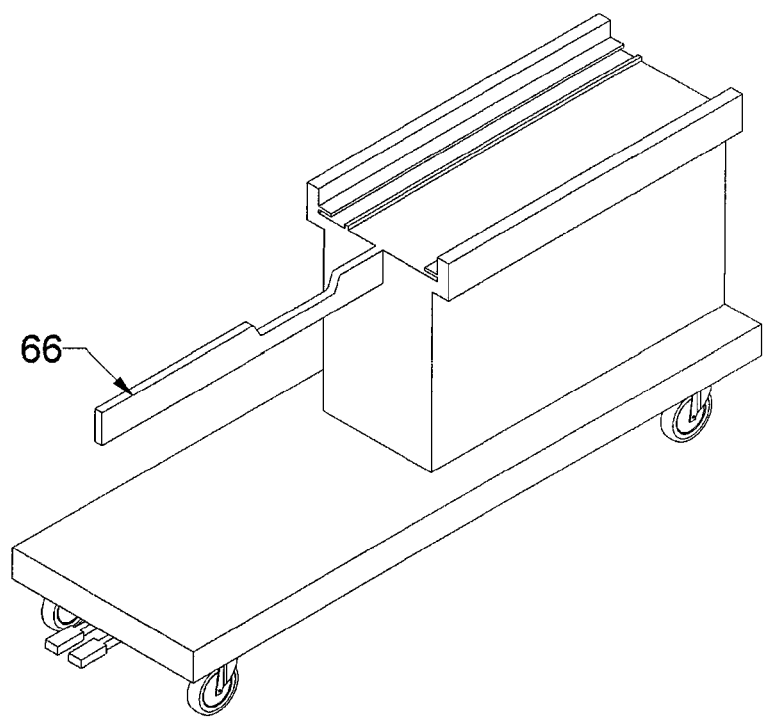
Figure 3G:
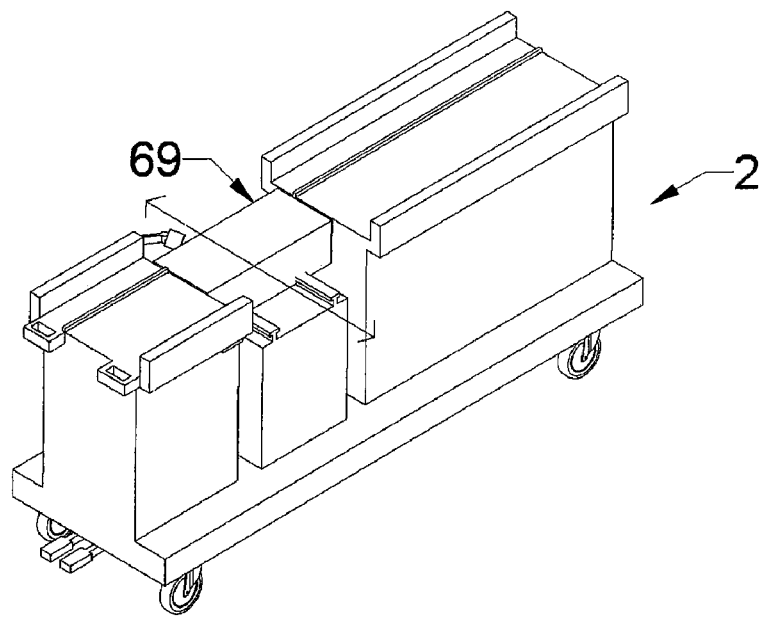

FIG. 3f shows that the stretcher may have a slim support 66 with a gap smaller than the support wheelbase distance, which ensures one wheel on the head end of the patient support is always supported FIG. 3g shows a stretcher with a bridge 69 that moves left or right allow medial access to one or the other breast.

Figure 3H:
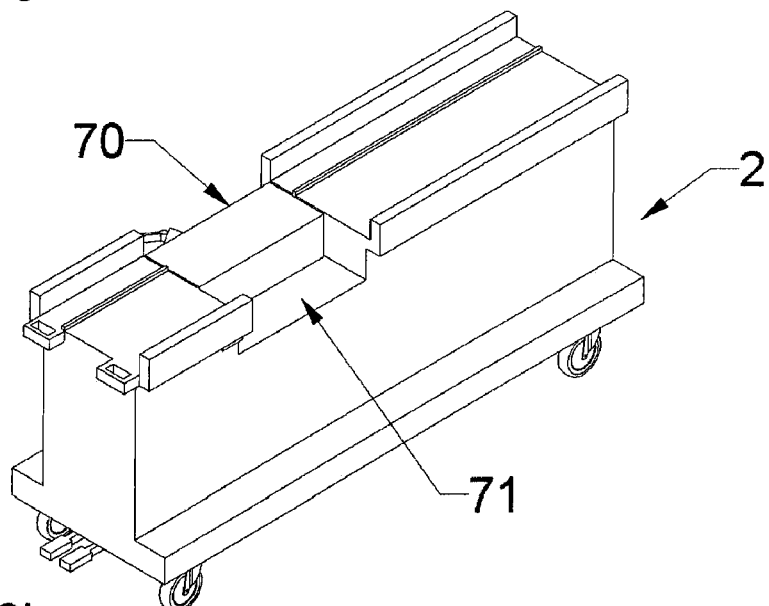

FIG. 3h shows a patient stretcher with a removable section 70 and the area from which it has been removed 71. This allows medial access to the breasts while assuring that the patient support structure 2 is in contact with the stretcher support surface 1.

Figure 4D:
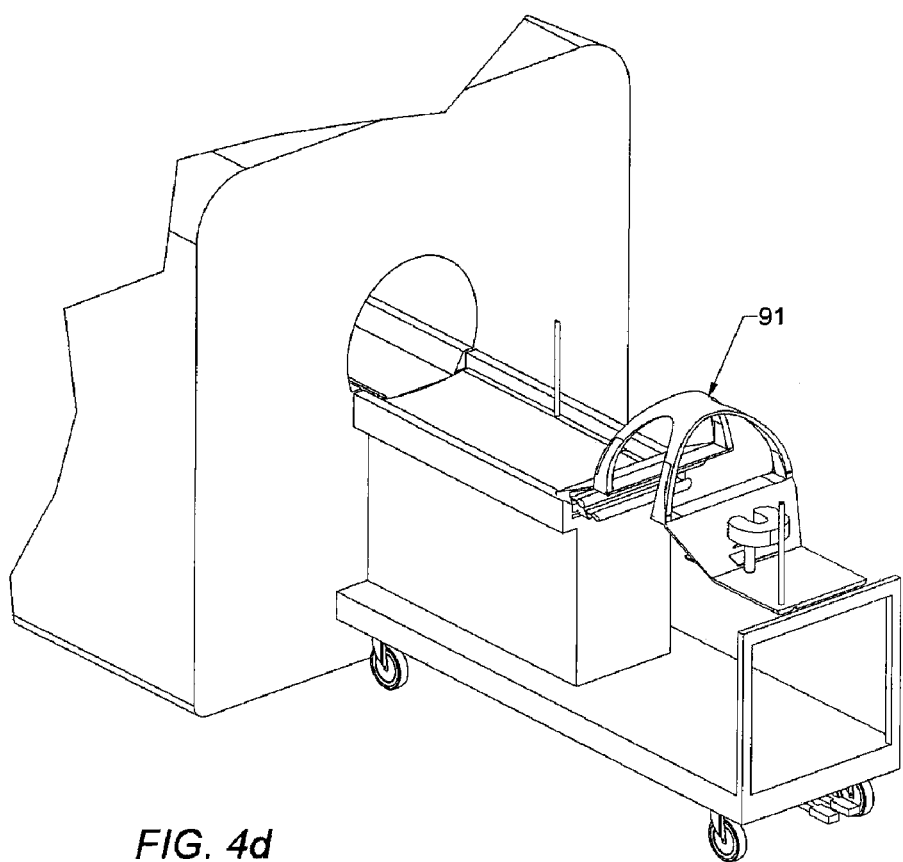
FIG. 4a shows how the patient support structure may be cantilevered over the interventional volume according to the method of the invention. This design provides for the maximum access to the breast. b shows the shape of the arches relative to the MR bore. In order to prevent the structure from tipping over with a patient in place and separation of the patient support from the stretcher, sliding or rolling constraints can be incorporated into the system. c shows various embodiments of these constraints. d shows the extension of the arch support structures so that they form a complete cylinder around the patient.

FIG. 4 shows another embodiment of a transport stretcher 78 and a cantilevered patient support structure 77 which provides patient support in a full cantilever position based on stronger arched members, adjusting the mass distribution of the apparatus to move the center of mass towards the inferior end of the bed and the addition of sliding or rolling constraints in the transport stretcher and magnet bore as needed to ensure the patient support cannot tip from the transport stretcher during patient manipulation. An example of appropriate tabletop constraints are illustrated in FIGS. 4a, b, c and d. In the context of a cantilevered design, the shape of the cantilevered patient support structure 77 and the arches 28 ensure rigidity of the support and its stability on the transport stretcher 78 while carrying a patient load. As illustrated in FIG. 4d, the arches 28 may be extended around the posterior of the patient to form a continuous or near continuous cylinder. This extension of the arches provides a continuous geometry that is extremely rigid and appropriate for a cantilevered patient support strategy.

In FIGS. 4a and 4b, the cantilevered patient support structure 77 may be cantilevered over the interventional volume 76 as indicated. This design maximizes access to the breast (not shown). In order to prevent separation of the cantilevered patient support structure 77 from the transport stretcher 78, sliding constraints 79 are incorporated to prevent tipping. Also indicated in FIG. 4a, is the addition of positional tracking devices 80 into the body of the stretcher. Removable handles 81 ensure full access to breasts (not shown).

In FIGS. 4b and 4b1, the matched fit of the curved arch 83 into the curve of the MRI bore 85 is shown.

This cantilevered approach of FIG. 4 provides the maximum real-estate and access in the vicinity of the breast for ancillary instrumentation such as US (ultrasound) imaging probes, therapeutic devices and positioning systems and to maximize access to the breasts from medial, lateral, superior-inferior or oblique directions for breast manipulation or interventional procedures. Also present may be an embedded positional tracking system. By integrating a positional tracking device into the stretcher (not restricted to, but including optical and magnetic tracking devices) at a position that provides line-of-sight, or reasonable proximity to the interventional volume t enables or significantly simplifies the procedures discussed further in this document.

FIGS. 4c1, c2 and c3 show alternative linear guides for the patient support guides. In FIG. 4c1, a tongue 90 in the transport stretcher 78 fits into a groove 92 in the patient support structure 77 to prevent rotational movement. In order for the cantilevered patient support structure 77 not to overturn during patient transport, it is necessary to constrain the motion of the patient support structure 77 to move in and out of the bore of the magnet 85 (S/I patient orientation). Some possible alternative embodiments of motion constraints are illustrated as FIG. 4c2 and FIG. 4c3.

FIG. 4d shows a modification of the arch structure 91 of the cantilevered design. The arches 91 in this illustration have been extended to form a complete cylinder around the patient. The opening provided in the arch structure 91 still enables access to the breast in the manner illustrated in FIGS. 2c and 2d. The degree to which the arches are extended around the patient is dependent on the structural strength deemed appropriate. Furthermore, the opening of the arch 91 may be widened in the Superior/Inferior direction resulting in more access to the breast at the expense of a relatively weaker structure.

FIG. 5a (1 and 2)-c shows only the plate locking system 104 of the patient support 100 and the related apparatus. The compression plates 102 can be moved anterior/posterior within the plate locking support 104. The compression plates/locking supports 104 can be introduced from the side of the apparatus. FIG. 5a1 is a side view and FIG. 5a2 is a bottom view. Each plate can be moved independently and to any position in the left/right direction. Additional compression plates in the superior/inferior direction can be accommodated so as to "box" the breast. In FIG. 5b, are shown height adjustable plates 112 and a guide 116 for the anterior-posterior compression plate that slides left and right. Various embodiments of rail positions that are possible are shown in FIG. 5c, as well as flexible sling 124 designs to compress the breast against the chest wall. Alternative locations for plate locking guide rails 120 are also shown.

Compression System

Each breast is compressed in the medial-lateral direction by a pair of compression plates 102 that are in turn held in place by a pair of plate locking supports 104 (FIG. 5a1, 5a2, 5b, 5c). "Compression plates" may have a number of different designs as described in the practice of this technology. Two or four compression plates may be used at a time depending whether unilateral or bilateral applications are being performed. The plate locking supports 104 may be constrained to move along linear guides in a medial/lateral direction. They may be free to be removed completely or added from the left or right sides of the patient support structure 100 while the patient is lying on it. The height of the compression plates 102 in the anterior-posterior direction can be adjusted along a linear guide fixed to each plate locking support 104. The compression plates 102 likewise can be added or removed from the plate locking supports 104 from the top or bottom, though only from the bottom when the patient is above them. Both plate locking supports 104 and compression plates 102 are continuously adjustable across the entire range of their support, do not interfere with one another and can be locked in place. The system illustrated in FIG. 5a-c shows two guide rails 120 to support the compression plate 102. With two guided rails on one side, this provides a completely open geometry toward the opposite end of the compression plate 102 to maintain greatest access. However, with such a geometry, the compression plate 102 may not demonstrate adequate rigidity that can be overcome by placing one guide rail at the opposite end of the compression plate 102. Similarly, using multiple guide rails placed at each end of the compression would further stiffen the system. In these FIGS. we have illustrated the guide rails to be rods and the compression plates 102 are fitted on the guide rails with linear bearings. Multiple configurations are possible, including the use of T slots and dovetails as dictated by the space available for these mounting structures. The locking mechanism for the compression plate 102 could be formed by a simple cam mechanism or ratchet and pawl structure which allow the use of one hand to both secure (lock) and position the compression plates 102. The positioning of plate-locking guide rails 120 can be variously positioned as shown in FIG. 5c.

Rail systems and tongue-and-groove compression plate support systems have been presented in the prior art. The design presented by Kuhl, 1997, demonstrates a dual rod system. This design differs significantly from the presented embodiments in that the medial and lateral plates can not be independently positioned, there is only provision for access to one breast at a time, and both plates can not be removed with the patient on the apparatus. Other designs presented in the prior art including U.S. Pat. Nos. 5,913,863, 5,855,554, 6,423,076 do not detail the compression apparatus, or demonstrate limited ability to position the plates as described by Kuhl 1997 (C. K. Kuhl, A. Elevelt, C. C. Leutner, J. Gieseke, E. Pakos, and H. H. Schild, "Interventional breast MR imaging: clinical use of a stereotactic localization and biopsy device," Radiology, vol. 204, pp. 667-675, 1997) and Heywang-Kobrunner 1999. (S. H. Heywang-Kobrunner, A. Heinig, and R. P. Spielmann, "MR-Guided percutaneous excisional and incisional biopsy," European Radiology, vol. 9, pp. 1656-1665, 1999.)

Another aspect of the present technology enables compression of the breast in the anterior/posterior direction. This is a particularly beneficial feature because US imaging and interventional procedures are optimized by increased breast contact with the compression plates. According to this technology, this can be accomplished by compressing the breast into a box-like shape as illustrated in FIG. 5c. U.S. Pat. No. 5,706,812 to Strenk et al. discloses an inflated bladder which improves access to the breast during US imaging. However, unlike the present technology, the invention disclosed by Strenk et al. does not provide for equivalent access to the lateral and medial sides of the breast during imaging and interventional procedures. This concept may be further extended to include rods, pointers, convex or concave surfaces, or the like that are attached to the compression plates and/or the patient support structure that perform the function of improving breast contact with the compression plates.

Another feature of the present technology is the ability to move and lock the medial and lateral plates independently through the plate locking supports using just one hand. This enables the operator to compress the breast with one hand, while locking it in place with the other. The ability to adjust the positions of the plates along the entire width of the bed is a useful feature which accommodates the various sizes of patients and various clinical applications (e.g. medial/lateral interventions, bilateral imaging). Another further aspect of the invention enables movement of the plates in the vertical direction during compression. This allows the operator to position the plate as close to the chest wall as possible. In the method of the invention, compression plates inserted into the plate locking supports may take different forms as described in the following section of this specification. The present technology provides a method to quickly interchange plates for various functions by vertically loading the plates into the plate locking supports. Furthermore, compression plates may be introduced or removed with the patient still on the apparatus by way of removal or addition of the plate locking supports (FIGS. 5a1 and 5a2).

Compression Plates

According to the present technology, numerous functions are accomplished using various types of compression plates. These functions include:

1) MR imaging coils: various coil arrays—single or multiple per compression plate.

Figure 6A:
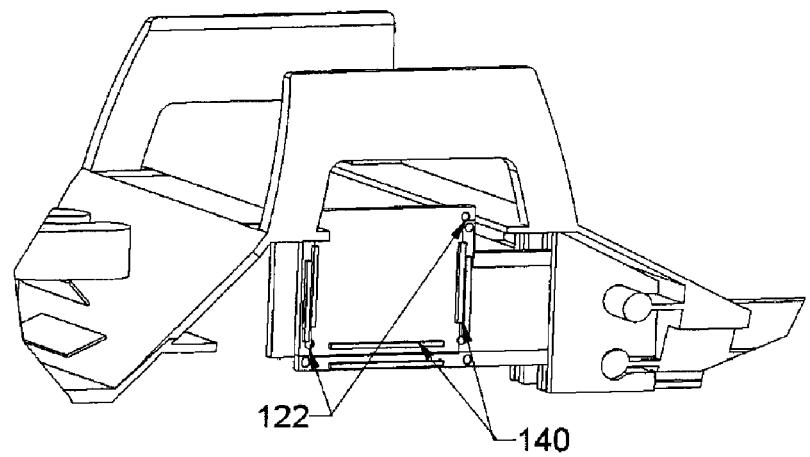
FIG. 6: illustrates how various compression plate designs may be accommodated according to the invention. a Attached to the compression plate are fiducial markers and fixed positions to attach coils and positioning stages. b Attached to these compression plates (or embedded within) are sets of coils. c The compression plate may be a fenestrated plate for needle access. d The plate may provide an acoustical opening for US imaging and intervention. e A transducer positioning stage may be attached at a fixed position on any compression plates.
Figure 6B:
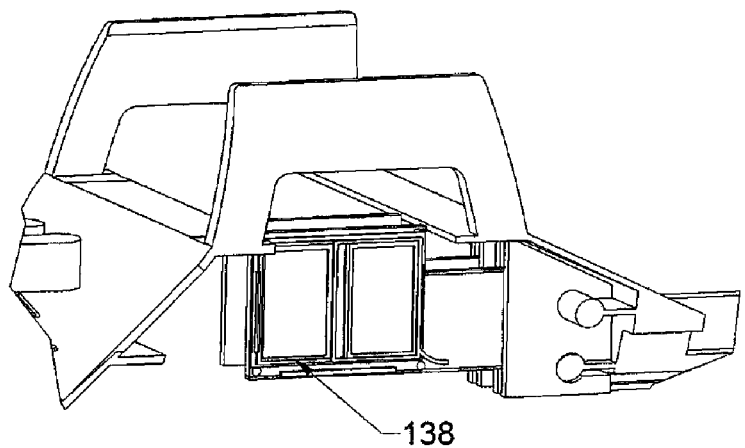
Figure 6C:
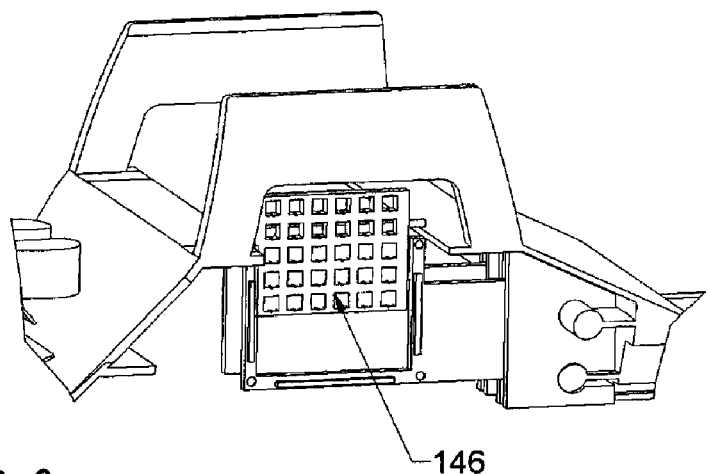
Figure 8:
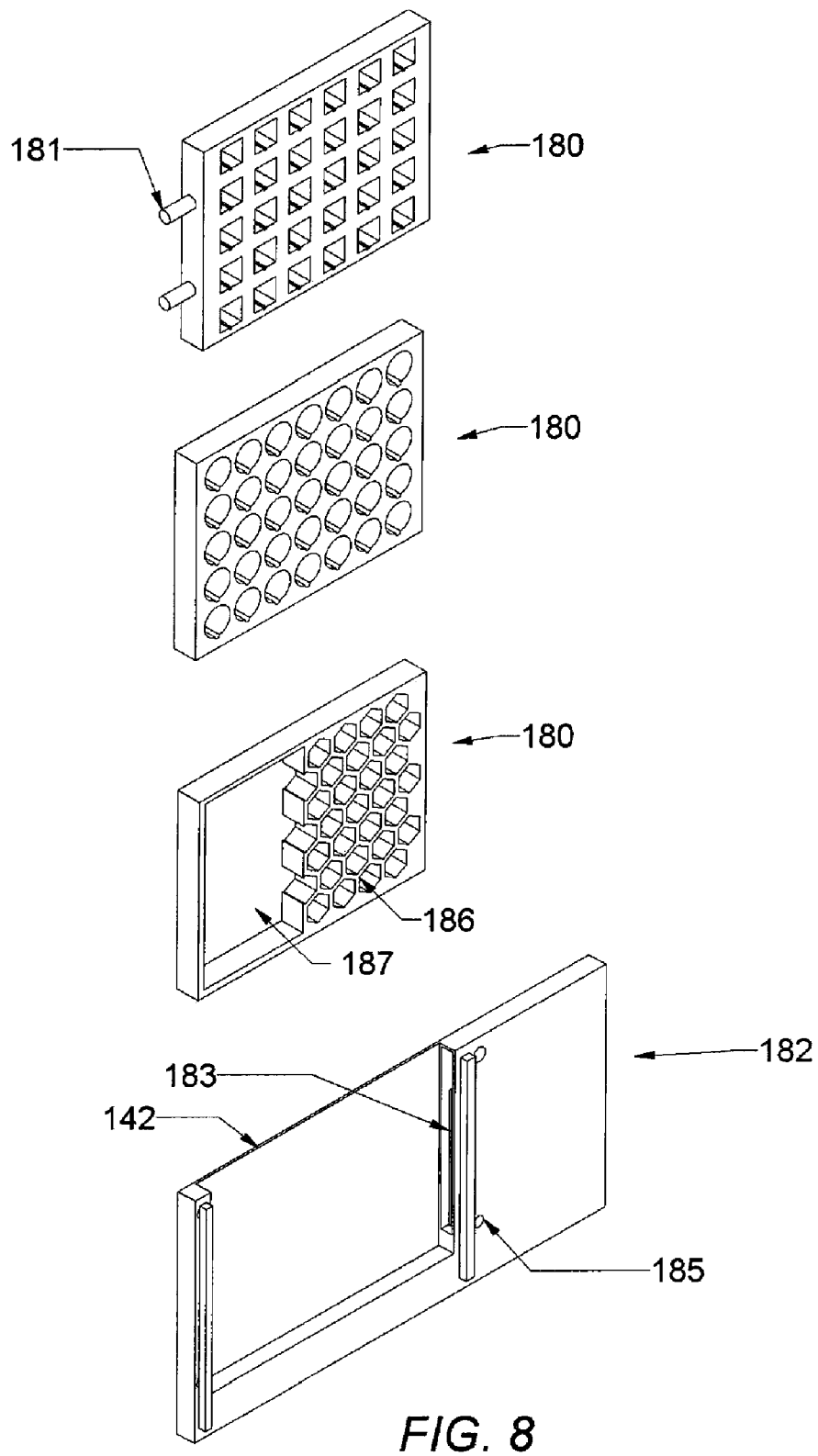
FIG. 8: shows various interventional compression plates that may be used according to the invention. Different fenestration shapes can be implemented as illustrated. A unique feature is the addition of a notch to one side of the opening or indexing component to make it asymmetric. This ensures plugs may be positioned into the opening in only one orientation. A compression plate consisting of a sterile membrane pulled taut across the frame as illustrated can be used to compress the breast as well can enable needle entry after making a small incision in the surface.

2) Interventional plates: multiple hole plates, fenestrated plate as shown in FIG. 6c, 8 (with various aperture shapes)

Figure 6D:
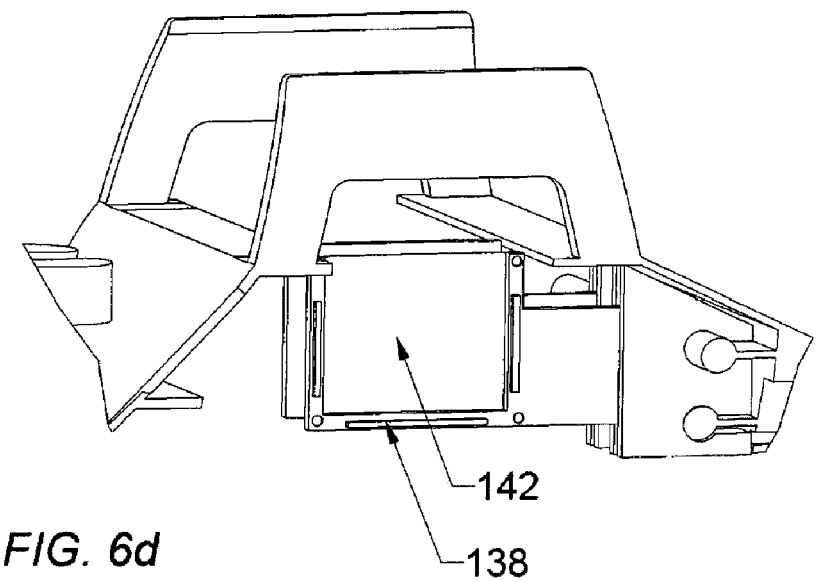
Figure 6E:
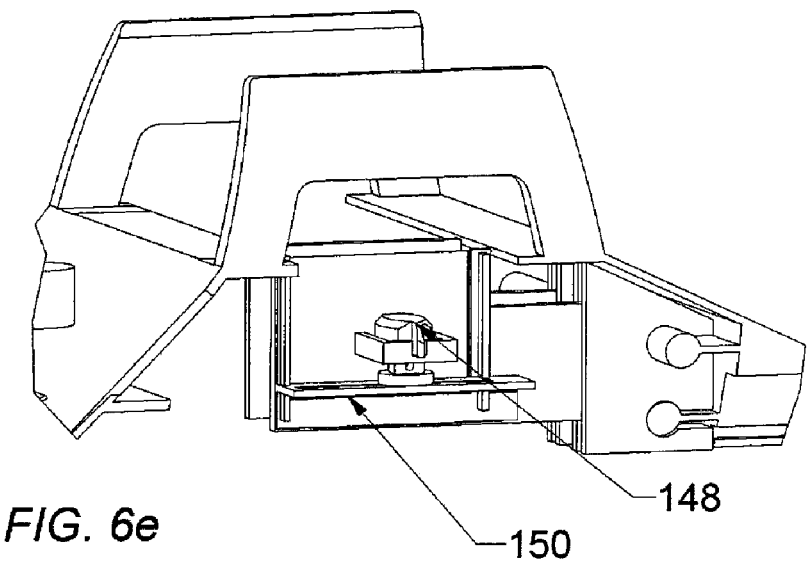

3) US-transparent membrane and membrane support frame which is
  a. Reusable for imaging
  b. Can be sterilized
  c. Can be cut to allow incisions in the breast
  d. Tension adjustable to adjust flexibility and conformation The compression plates also holds a breast immobile while a fenestrated plate in contact with it is moved The plates disclosed by this invention can be sterilized and can hold several fiducial markings 140 (e.g., FIG. 6a) visible on MRI which act as reference points between the MR images and the physical space. The plates can also have attachment points for MR imaging coils (FIG. 6b), needle positioning apparatus (FIGS. 10a and 10b) and US transducer positioning systems (FIG. 6e). The design and function of these plates will be discussed in detail in a subsequent section of the specification in the context of their clinical use. A plurality of compression plates that may be used according to the technology are identified on FIG. 6a, 6b, 6c. The compression plates may be positioned at any of the 4 compression points (left medial, left lateral, right medial, right lateral) on the breast in any combination required. FIG. 6c shows compression plates with fenestrated plates 146. FIG. 6e shows a transducer 148 and a positioning stage 150. These coils can be interchanged in a modular fashion to maximize and optimize the number and types of coils used, whether for unilateral or bi-lateral imaging or intervention. Modular coils may also provide either large or small coils of various designs, RF shields, and coils for different field strength and field shapes.

FIG. 7 shows various coil configurations a, b, c, d, and e from an axial view of a patient on the apparatus. a) shows a Bilateral imaging application with 4 coil array. b) shows a Unilateral imaging configuration with 4 coil array. c) shows a Bilateral imaging with 4 coil array 160. In order to reduce coupling between the medial coils, their size has been reduced and an RF-shield has been inserted (attached to sternum support) to limit coil interactions. This shield may take a variety of forms all with the same purpose—passive medial coil decoupling. d) shows RF-shields have been attached to the medial compression frames. e) shows that Coils may also be attached to the A/P (anterior/posterior) compression plate and used with any of the aforementioned coil geometries. In all cases the maximum number of allowable coils, for the maximum number of data collection channels should be used. A sternum support 162 is also shown, as well as a sternum support with RF shield 164, and RF-shields attached to the medial compression plates 166.

Imaging Coils

MR imaging coils are considered in this technology. In one embodiment, the coils may be incorporated into the system by being embedded into the compression plates as by way of non-limiting examples, using fixtures 122 for coil attachment in FIG. 6a. In another embodiment, the coils 138 may be attached to the outside of the interventional or US transparent plates 142 as shown in FIG. 6d. In another embodiment additional coils may be embedded into the patient support structure. In another embodiment, the coils may be positioned as close as possible to the breast in order to produce higher-quality images. The MR coils may consist of a single pair of coils per breast (1 medial, 1 lateral), or an array (more than two coils, multiple pairs of coils) per compression plate. Further enablement for coil configurations per se may be found in Schneider et al., "An Apparatus for MR-Guided Breast Lesion Localization and Core Biopsy: Design and Preliminary Results," Journal of Magnetic Resonance Imaging, vol. 14, pp. 243-253, 2001, which is incorporated herein by reference. However in that description, no attempt was made to maximize the number of coils used for imaging unilateral or bilateral anatomy. As a comparison, in the description provided by Greenman, et al., MRM 1998, no attempt was made to ensure the medial and lateral plates could both be positioned as close as possible to the breast through an appropriate compression system to maximize image quality. In the present technology, moving the medial coils further from one another would provide reduced coil decoupling and limit the issue of coil interactions and the complexity of coil switching circuitry. Furthermore, no attempt to substitute coil arrays so as to maximize the number potentially used for unilateral or bilateral imaging without has been made.

The present technology can also provide for coils specific to different sized patients. A different set of coils could be used for needle positioning sequences than those used for simple imaging. These coils for needle positioning would have a large central opening through which needles could be placed and would be mounted over top of other compression plates (e.g. a fenestrated plate and/or US transparent membrane). According to the invention, these coils would be removable and their positions on the underlying compression plate would be adjustable to ensure clearance from a device being inserted into the breast.

Fiducial Marker System

In the methods of the present technologies, device delivery may be based on the use of MR-visible fiducial markers as a reference between MR images and physical space. "MR Imaging-guided Localization and Biopsy of Breast Lesions: Initial Experience," Radiology, vol. 193, pp. 97-102, 1994, and Kuhl et al., "Interventional breast MR imaging: clinical use of a stereotactic localization and biopsy device," Radiology, vol. 204, pp. 667-675, 1997 describe the use of fiducial markers placed at a known position on the embedded or attached apparatus. The more reference points that are used, the more accurate is the registration of the two spaces (physical/imaging). Various embodiments of the fiducial markers may be used. The fiducial markers may be embedded into some compression plates in the apparatus for simplicity. In other structures, such as fenestrated plates which may be moved relative to the breast during a procedure, the markers may be removable. They may also need to be removable if they may not be sterilized. Device targeting and trajectory calculations can be automated if the fiducials are at a known position on the apparatus. Another embodiment of fiducial marker arrangements includes a detachable plate which may be positioned at a fixed position in the compression frame relative to the fenestrated plate positions (e.g. FIG. 18a).

MR Breast Imaging

The prior art references indicate that the majority of breast imaging procedures involve simple contrast-enhanced breast imaging without intervention. It is important to have a system that is capable of single or bilateral breast imaging for screening, diagnostic or surgical planning purposes.

According to the present technology described herein, both unilateral and bilateral breast imaging procedures can be performed with the simple removal and replacement of compression plates containing coils and coil arrays and the removal and replacement of the central support member (used in bilateral imaging) with various support members. The addition of coil decoupling mechanisms such as coil windings, specially designed conductive layers, and electronically active blocking circuits into the space between the two coil pairs is enabled by the open architecture of the apparatus of the present technology. One embodiment includes attachment of the mechanism (illustrated in FIG. 7 as an RF shield), to the bottom of the central support member. Quick attachment of this member enables easy preparation of the system for various imaging purposes. Alternatively, more than one RF shield could be introduced and mounted on the guide rails to be positioned in a patient-specific manner to optimize imaging performance. The open architecture disclosed in this invention further enables improved access to the breast for the operator for breast positioning before imaging. The addition of lighting and a mirror system enables visualization of the breast. The ability to see the nipple and the ability to move the medial and lateral plates independently facilitates having the nipple pointed downward and in the middle of the imaging field. This is important as the nipple is used as a reference point for the radiologist. Furthermore, the ability to move the plates up towards the chest wall ensures optimal compression of the breast ensuring there is minimal motion during the procedure.

According to this invention, the ability to use different coil configurations for different purposes (bilateral, unilateral) and to accommodate various patient breast sizes (e.g. one set for large, one set for small breasts) is critical to acquire optimal images. Depending on the number of data acquisition channels in the MR imaging system, multiple coil arrays can be used. Various coil geometries which may be used in the method of the invention are presented in FIG. 7. This concept of removable coils has not been presented in the prior art with respect to 1) providing the maximum number of coils for the imaging application (bi-lateral, unilateral, interventional imaging) so as to maximize the number of active data collection channels. 2) Adjusting coil arrays for smaller or larger breasts, 3) Upgrading coils and coil cabling as the associated MRI system is upgraded for increased number of data channels, 4) Providing coils operating at different frequencies for higher magnetic field applications. The ability to easily remove coils and exchange them for other coils without modification of the main imaging structure is a critical feature enabling optimized imaging and interventional functions with a single apparatus.

MR-Guided Breast Interventions

Various breast interventional procedures are enabled by the apparatus and method of the present invention. The ability to perform core biopsy, wire localization, lesion marker placement, guide tissue ablation devices and placement of tissue therapy devices (chemotherapy, radiotherapy, cryotherapy, heat therapy, gene therapy) are some of the clinical applications enabled by the invention. Apparatus and techniques common to these procedures are presented in the following section.

MR-Guided Device Delivery

The ability to accurately deliver a plurality of needles to a lesion or to multiple sites within the breast using MRI guidance is a fundamental aspect of the present invention. According to the method of the invention, fiducial markers can be used as reference points, so that the operator can position various MRI-compatible needles (e.g. titanium and composite needles) ranging from fine aspiration needles (approx 24 gauge (0.51 mm)), to wire delivery needles (20 gauge, (0.81 mm)), to conventional core biopsy needles (16 to 14 gauge (1.29 mm-1.63 mm)), coaxial introducer needles (14 to 11 gauge (1.63 mm-2.30 mm) to accommodate the core biopsy needles), and large vacuum assisted biopsy needles and their introducer needles (14 to 9 gauge (1.63 mm-2.91 mm), or larger). The ability to infer needle position using signal void produced by needle susceptibility artifacts is well established in the prior art, for example, U.S. Pat. Nos. 4,989,608 and 5,154,179 to Ratner, U.S. Pat. Nos. 5,744,958 and 5,782,764 to Werne, and U.S. Pat. No. 5,944,023 to Johnson et al.

Delivery of hollow needles for purposes such as acquiring tissue samples by biopsy, or implanting wires or other markers as guides for surgical excision is founded on the same general procedure. Initially the breast of interest is compressed between two plates designed to allow needle access to the breast. These plates may take many different forms as indicated in FIG. 8. One embodiment consists of a plate with a large number of apertures to guide needles of interest. Other plates contain a series of apertures of specific shapes and size which provide access to the breast to prepare for intervention by injecting local anesthesia and making a skin incision. These are known as fenestrated plates. An array of square apertures have been disclosed in prior art references, for example, U.S. Pat. No. 5,855,554 to Schneider et al and U.S. Pat. No. 6,423,076 to Cardwell et al. Various other implementations may include circular, triangular, hexagonal, or other aperture shapes, with various positioning, or packing orientations on the compression plate 180 as indicated in FIG. 8. Each plate 180 may have features 181 for positional adjustment (e.g., anterior-posterior). Each fenestration preferably has an asymmetrical shape to assure proper orientation within the support assembly 182 that has a membrane 142, fixture for fenestrated plate attachment 183, and fixture for orienting coil attachment 185. There may be keyed fenestrations 186 and ultrasound transparent membranes 187 in the assemblies of the compression plates 180. Needle guidance is accomplished by installing a guide plug with appropriate cross section in one of the apertures. These guide plugs have boreholes sized to guide interventional devices (such as needles) of various gauge sizes and lengths. The simplest implementation involves an array of holes in a plug sized to fit into one of the fenestrated plate's array of apertures. These smaller holes act to guide the needle into the breast in a straight manner, minimizing the tendency for the needle to deviate from a medial-lateral trajectory. Other types of needle guide plugs can be used with the system. For a particular fenestrated plate, a number of guide plugs can be provided to accommodate various needle gauge sizes.

The procedure of MRI needle guidance according to the invention is demonstrated in FIGS. 9a, b and c. A typical example of such a fixation frame 200 is shown in FIG. 9a, which serves to hold the breast 220 in a fixed geometry during the biopsy procedure and also support MRI-visible fiducial markers 204, which are used for subsequent registration. The frame 200 holds the breast while the patient is in a prone position in the MR system. The frame holds the breast in a medial-lateral direction. The biopsy needle 202 and MR coils 203 are shown. A cancer lump 212 is shown within the breast 220 and guide holes 208 are shown in the guide plate 206. Plug inserts 214 are shown for the window assembly 216. Other orientations such as cranial-caudal or oblique are possible, however have not been presented in the prior art to our knowledge. A means of MRI-guided needle delivery as indicated in FIG. 9 has been presented in various forms in the Prior Art (Orel et al., *Radiology*, vol. 193, pp. 97-102, 1994; Kuhl et al., *Radiology*, vol. 204, pp. 667-675, 1997; Fischer et al., *Radiology*, vol. 192, pp. 272-272, 1994; Doler et al., *Radiology*, vol. 200, pp. 863-864, 1996; Fischer et al., *Radiology*, vol. 195, pp. 533-538, 1995; Heywang-Kobrunner et al., *European Radiology*, vol. 9, pp. 1656-1665, 1999; Liney et al, *Journal of Magnetic Resonance Imaging*, 2000, Su (U.S. Pat. No. 6,163,717), Fischer (U.S. Pat. No. 5,913,863), Cardwell (U.S. Pat. No. 6,423,076)) and embodied in commercial breast imaging devices by MRI Devices Inc, USA Instruments, MachTech Inc. The basic premise of this approach is not novel for use as an MRI-guided needle positioning method. This prior art forms the basis of many of the inventions described further in this document where guidance of needles based on fiducial markers at known relative positions to fenestrated guides and plates is required. Differing features are highlighted where appropriate with respect to MRI-guided needle insertion and the associated apparatus.

Fundamental to MR-guided needle guidance in the manner described above is a compression frame constructed of a fenestrated plate 206, which serves to accept a guide plug 214. As shown in FIG. 9, this holder has an array of small apertures, on close centers. Fiducial markers 204 are placed on the grid array of the window assembly 216 and imaged along with the breast 220 during the MRI aspect of a procedure. These markers 204 are visible in the MRI data set along with the suspicious mass 212. By measuring the location of this mass relative to the fiducial markers in the image, the exact location of the lesion can be determined relative to the grid array frame in physical space.

Figure 11:
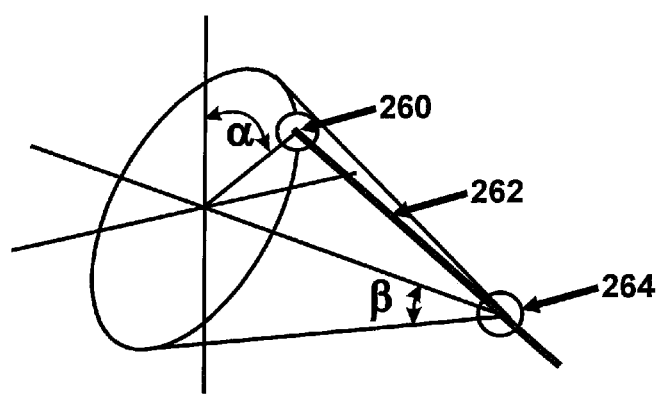
FIG. 11 illustrates some useful aspects of needle orientation geometry according to the invention.
Figure 12:
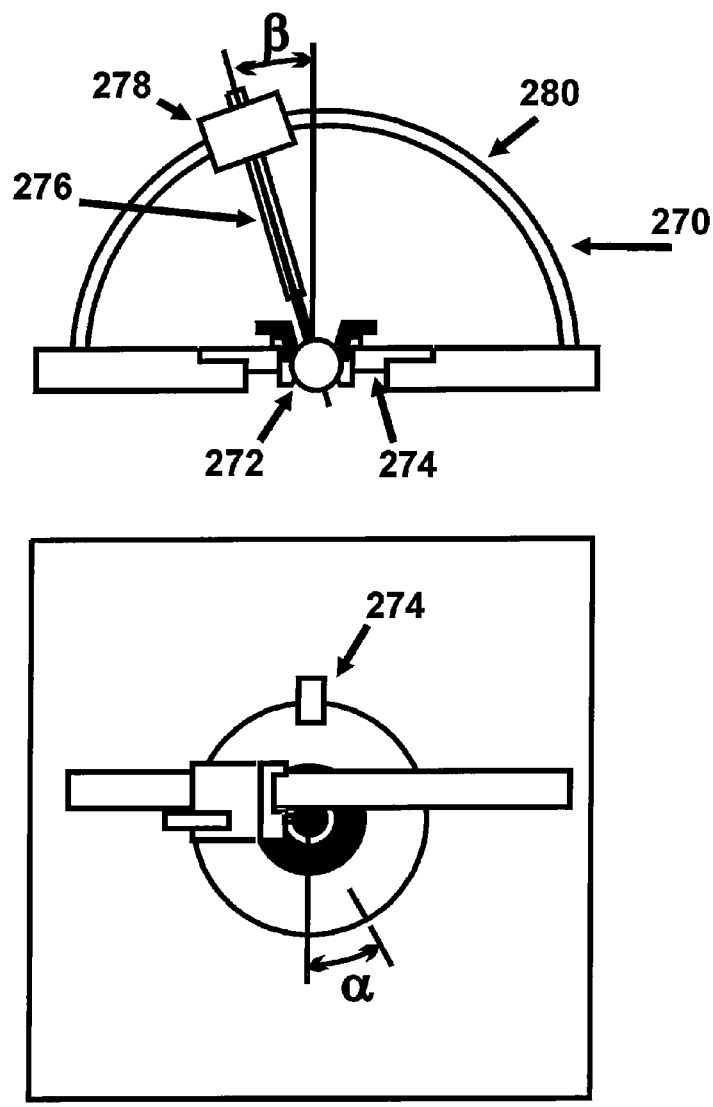
FIG. 12 shows a goniometer that may be used according to the invention to define needle guide orientation.

According to the invention, it may be desirable to deliver devices to multiple locations within the breast (e.g. core biopsy requiring multiple core samples) or to bring the device along an oblique trajectory. In these applications, limiting the needle orientation to a straight (medial to lateral) trajectory is undesirable. Positioning the needle in a straight manner limits the accuracy, which the needle may be positioned, and multiple samples would require multiple skin incisions. Since device delivery can only be achieved through a finite number of holes, the specificity of device positioning is limited. So for some applications a different guide plug capable of defining an angled needle trajectory is required. An embodiment of such a guide plug 230 is shown in FIG. 10. It is composed of a gimbal 240 which allows rotational freedom in two directions. The needle guide 232 is a hollow tube passing through the centre of the gimbal 240 which allows free rotation of the gimbal 240 about a centre of rotation in the insert form 238. By turning the clamp 234, it is possible to lock the needle guide orientation. We later propose a goniometer to set this orientation (FIGS. 11, 12). Such a design for a gimballed guide plug has been demonstrated in previous U.S. patent documents (U.S. Pat. Nos. 6,195,577 Truwit et al, 6,267,769 Truwit, and 6,368,329 Truwit) and is embodied in the Navigus brain biopsy system developed by Image Guided Neurologics, Inc. However, the design of the system of the present invention is substantially different in that the base of the guide plug can only be positioned in the slots of the fenestrated plate in one orientation. Furthermore, the present invention can be further distinguished from the prior art because the plug is constructed so as to minimize the variations in the needle entry point for varying angles of the gimbal as discussed above This is desired to provide a common entry point to the skin for gathering multiple tissue samples. As such, it is desired to have the design optimized such that the centre of rotation of the needle 233 is close to the surface of the skin in order to facilitate multiple needle entries at different needle trajectories without the need to increase the size of the incision as discussed above. This can be achieved by removing a portion of the gimbal is shown in FIG. 10 to create a flat zone which is applied to the skin surface while still providing a spherical surface for rotation and locking of the gimbal. In FIG. 10b, the insert form 250 is shown with an alternatively designed gimbal 252.

Once the gimbal is set, its orientation relative to the fenestrated plate must be fixed. This is accomplished by the use of a key or some other unique shape which aligns with a feature in the fenestrations of the compression plate. Based on the MRI coordinates, the lesion 260 location is defined by two angles shown as $\alpha$ and $\beta$, and an insertion depth z as shown in FIG. 11. The angle $\beta$ determines the offset angle of the needle trajectory 262 from a perpendicular delivery into the tissue and describes a cone with its apex at the center of the needle gimbal 264. The surface of the cone passes through the lesion at azimuthal angle $\alpha$ on this cone surface. To prescribe these two angles to the guide plug, a goniometer 270 may be used as shown in FIG. 12. This device is a simple mechanical structure, provides specified orientation of the needle (not shown) in the gimballed guide plug 272 prior to insertion. The guide plug 272 is placed in the keyed guide plug disc or needle holder disk 274 and a sterile needle guide extender 276 is placed over the needle guide plug disk 274. This extender is used to deliver the desired angles in the goniometer system. First the guide plug disc 274 is rotated to angle α and the guide plug slider clamp 278 is secured to preserve this angle on the slider ring 280. Then the slider clamp is rotated to define the angle β as shown, after which this is also clamped to prevent further motion. To preserve the orientation of the guide plug, a clamp on the guide plug 234 is activated to lock the gimbal and needle holder in position. The guide plug can be removed and inserted into the fenestrated array. Once in position, the needle is advanced the necessary distance as determined from the MRI data to intersect the lesion as desired.

In order to ensure sterility throughout the procedure, the guide plug disc, guide plug and needle guide extender can be sterilized for each patient, or may be disposable items. If multiple biopsies or entries into the tissue are needed, multiple guide plugs can be used, each of which are positioned to the desired location by the goniometer prior to or during the biopsy procedure. With each guide plug pre-set, or set elsewhere by an assistant, the biopsy procedure can be efficient and rapid.

According to the present invention, it is possible to introduce a device at an arbitrary orientation while preparing another device orientation in a separate guide plug using a goniometer. The design and use of a goniometer to define and set the position of a guide plug for interventional procedures is unique with respect to the prior art. Attempts to precisely define angulations through mechanical apparatus at the site of interest have resulted in bulky and inappropriate devices as demonstrated in U.S. Pat. No. 6,048,321 by McPherson et al, and a neurological application U.S. Pat. No. 5,984,930, by Maciunas. Specific implementations for breast biopsy include U.S. Pat. No. 6,423,076, Cardwell et al, and Heywang-Kobrunner 1999. These designs differ in that the angular position of the needle is defined by an apparatus attached to the compression frame immobilizing the breast. In this manner, large bulky apparatus are required and limited angulation is available.

Various embodiments of the fenestrated plates, gimballed plug and goniometer are possible according to the invention. The apertures of the fenestrated plates, the base of the guide plug and the corresponding aperture in the goniometer are of the same cross-section (e.g., circular, square, triangular, hexagonal, etc). Furthermore the goniometer would serve the same purpose if either the arch or the disc (but not both) subtended only one-half of the range shown (i.e. either 90 degrees or 180 degrees respectively). In the method of the invention, the needle can be introduced from either the medial or lateral sides of the breast by placing a grid plate on the corresponding side of the breast. The needle trajectory is preferentially determined such that the minimal amount of breast tissue is traversed, however in cases where many needle passes may be required, a constraint to minimize the number of skin incisions and make all passes through one aperture may take precedence. This system enables a flexibility to allow for many different needle trajectories to approach the lesion. Similarly, it allows the needle to be introduced at arbitrary angles to ensure safe and appropriate insertion of a needle into a tumour. For example, for lesions near the chest wall, it is imperative that the needle follows a path parallel to the chest wall and not inclined to it, so that the possibility of chest wall penetration is eliminated.

Figure 13A:
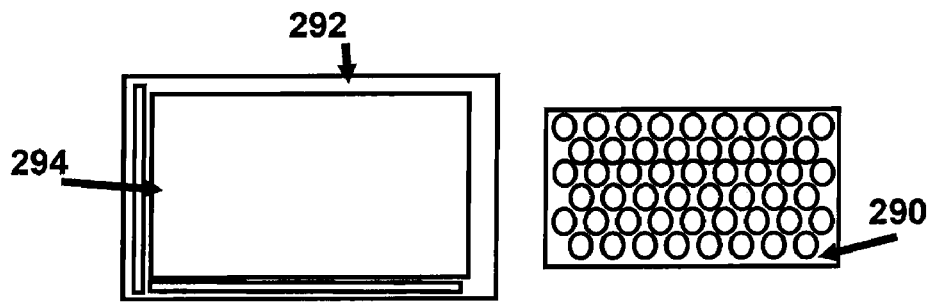
FIG. 13 illustrates the angulated biopsy procedure according to the invention.
Figure 13B:
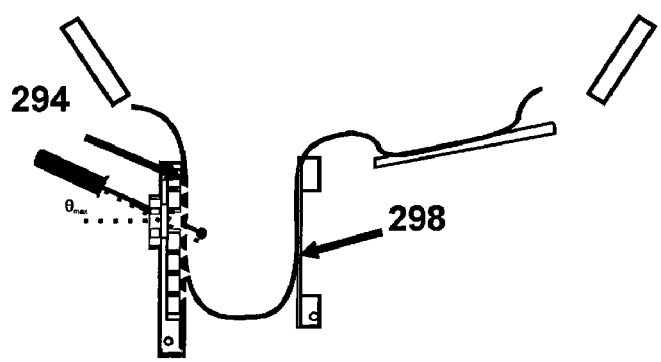
Figure 13C:
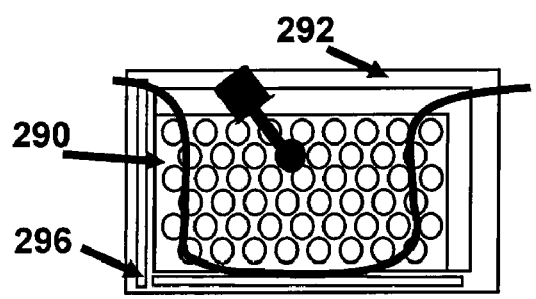
Figure 14A:
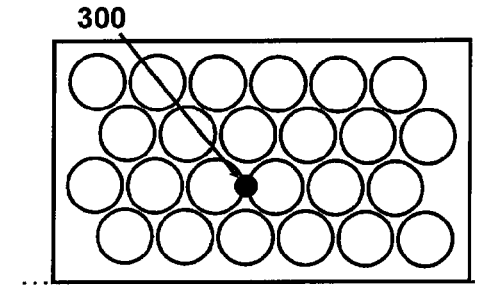
FIG. 14 shows a combination fenestrated plate and compression membrane. According to the invention, by compressing the breast using a compression membrane with a fenestrated plate that can move relative to the breast, more of the breast is accessible for needle guidance.
Figure 14B:
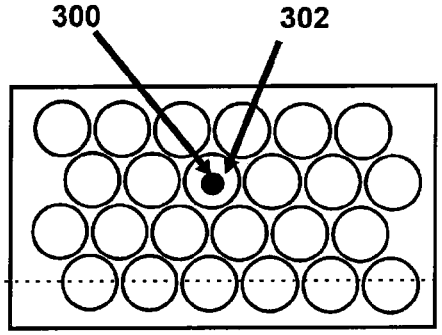
Figure 14C:
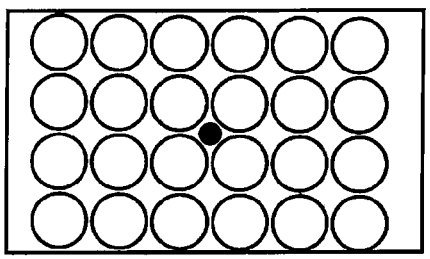
Figure 14D:
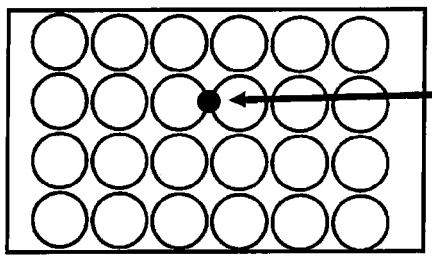
Figure 14E:
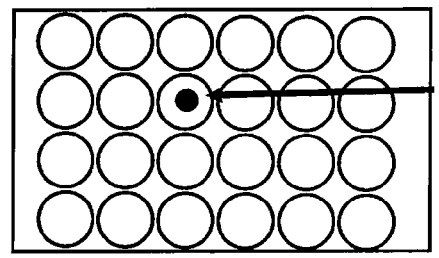

A weakness with a fixed fenestrated plate is that various regions of breast tissue are inaccessible to the needle (areas at the edges of the fenestrated plate and those occluded by the material of the plate itself). Due to limitations on the angulation of the gimballed guide plug, large areas of tissue may be inaccessible. A solution to this is provided by the present invention as shown in FIG. 13. By decoupling the two functions of compression/immobilization of the breast and stereotactic frame, accessibility of the breast tissue can be optimized to minimize the effects of "blind-spots" in the breast. This fenestrated compression plate consists of a frame 292 with a sterile plastic membrane 294 pulled taut across its surface that can be cut and punctured with a scalpel or a needle (e.g., Opsite™ surgical material, or other membrane transparent to ultrasound). This plate is used to compress and immobilize the breast. Attached to this frame/membrane combination on the side opposite the breast is a fenestrated plate 290 as identified in FIG. 13. This effectively decouples the function of the previous embodiment of the stereotactic frame: the film compresses the breast, while the frame provides a plug and needle guidance reference frame). Fiducial markers 296 may either be attached to the compression plate 292 or the fenestrated plate 290. The fenestrated plate 290 must be designed such that it can be attached to the frame in various orientations, adjustable for position such that the fenestrations can be centered over different regions of breast tissue. Removing the fenestrated plate and repositioning it into the frame at a different orientation, or adjusting its position (in superior-inferior or anterior-posterior directions) without removing it would provide access to tissue which would otherwise be occluded. When the fenestrated plate is moved or removed, the breast would not move relative to the compression plate, as the function of breast compression and immobilization is provided by its membrane. Different embodiments of this concept are illustrated in FIG. 13. Furthermore, it is important to distinguish that required repositioning of the fenestrated plate to access previously inaccessible regions depends on whether fenestrations are organized in a hexagonally package structure or a rectangular grid and indicated in FIG. 14. For example, in this FIG., consider a desired point for biopsy 300. In the various fenestrated plate orientations, the openings have been shifted (by shifting the fenestrated plate within the frame) to assure that the desired target point 300 is accessible through a hole 302. The plates may be shifted up, down, left and right to align the hole 302 with the target point 300. If we had a rectangular grid of holes moving the plate up does not put the point at the centre of a hole. A second repositioning of the plate is required in the S/I direction. As such hexagonal arrangements are more efficient. As mentioned previously, many fenestrated plate systems are available, and have been presented in the Prior Art. However none have demonstrated the ability to decouple the function of compression and providing a stereotactic frame. This invention provides a significant advantage to access the "blind-spots" associated with fenestrated plate stereotactic systems.

According to the invention, both straight and angled needle trajectories can be determined with a calculation based on various criteria:

Adopt shortest needle path to target (medial or lateral approach as appropriate, minimal angulation of needle).
Limit multiple samples through a single fenestration.
Select arbitrary fenestration—determine appropriate needle trajectory.
Avoid patient support apparatus and other equipment.
Avoid anatomical features such as chest wall.
Needle Position Verification:
According to the invention, for all MR-guided needle guidance strategies, MRI verification is required to ensure the needle is positioned appropriately. However a strategy that includes software verification of the needle trajectory before needle insertion can be embodied in the needle trajectory guidance software. Visualization of the planned needle trajectory on the MR image set used to identify the lesion can be accomplished by superimposing an indicator on the MR images. This is particularly important to identify the expected position of biopsy needles after insertion.

Identification of the lesion after needle insertion may be difficult in situations where the lesion is smaller than the artifact generated in the MR image. According to the invention, software may be implemented to determine whether the lesion has moved after needle positioning. Imaging along the length of the needle (axial image acquisition corresponding to a needle trajectory in the medial/lateral direction), enables visualization of the needle depth. Identification of anatomical features of the breast before and after needle insertion provides a comparison to identify whether there has been gross motion of the lesion (inferring lesion motion from the surrounding interfaces when the lesion cannot be identified). MR images acquired before or after contrast agent injection prior to needle insertion can be compared to images acquired after needle insertion. Scaling and registration of these images, detection of tissue interfaces in the images and determination of the differences in these edge positions enables measurement of the tissue motion after needle insertion. In cases where there is large tissue deflection and/or deformation, the needle position may be corrected.

EXAMPLES OF CLINICAL APPLICATIONS OF THE INVENTION

Example 1

MR-Guided Wire Localization

Figure 25:
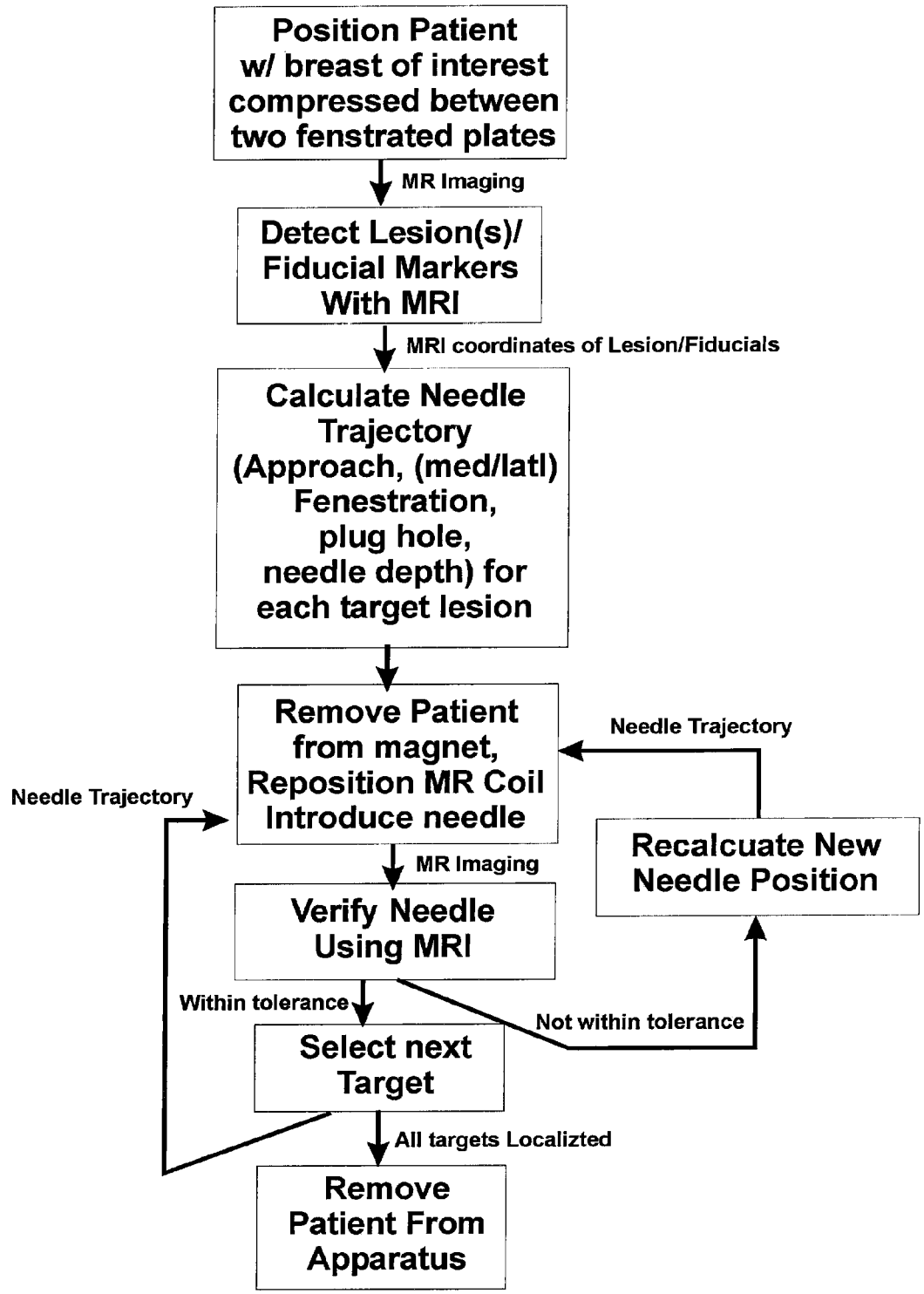
FIG. 25. Flowchart illustrating the MRI-guided needle localization procedure according to the invention.

The use of device guidance techniques to deliver a localization wire or marker to guide surgical intervention is illustrated in the flowchart shown in FIG. 25. The patient is first positioned on the patient support apparatus. The breast of interest is then compressed between two fenestrated compression plates with attached fiducial markers, which are attached in turn to the compression plate locking supports. These fenestrated plates are sterile and can be introduced while the patient is in the prone position. These plates can be moved in the anterior-posterior direction to positions near the chest wall to enable full interventional access to the breast. MR imaging coils are attached to these compression plates. MR imaging is then used to identify the lesion and the fiducial markers. Using this information, the appropriate fenestrated plate aperture and needle guide plug hole are determined in order to position the needle as closely as possible to the desired target position. Medial or lateral needle trajectories will be selected to minimize the depth of tissue being traversed, depending on the position of the target within the breast.

The patient is then removed from the imaging magnet and the marker guide needle (which is hollow in order to permit delivery of markers through it) is inserted according to the trajectory calculations. If more access room is required, the interventional volume below the breast may be accessed by retracting the bridge in the transport stretcher. The MRI coils may be removed as required to provide more access to the breast, and can be repositioned on the compression plates in order to reduce any interference with the marker guide needle or wire/marker. The transport stretcher's bridge is replaced. Walls on the side of the stretcher's bridge may be used to ensure clearance of all devices from the magnet bore. The patient and patient support are next advanced back into the magnet bore and MRI is used to validate the needle position. Strategies to determine if surrounding tissue has deflected in cases where the lesion may not be well visualized may be implemented based on the images acquired. The needle position may be repositioned and again verified for position. The final step entails insertion of the wire or marker into the tissue through the hollow guide needle and removal of the needle leaving the wire or marker in place in the breast. The guide plug, fenestrated plate and compression plates may then be removed from the breast and the interventional procedure completed.

Example 2

MR-Guided Angulated Breast Biopsy

Figure 26:
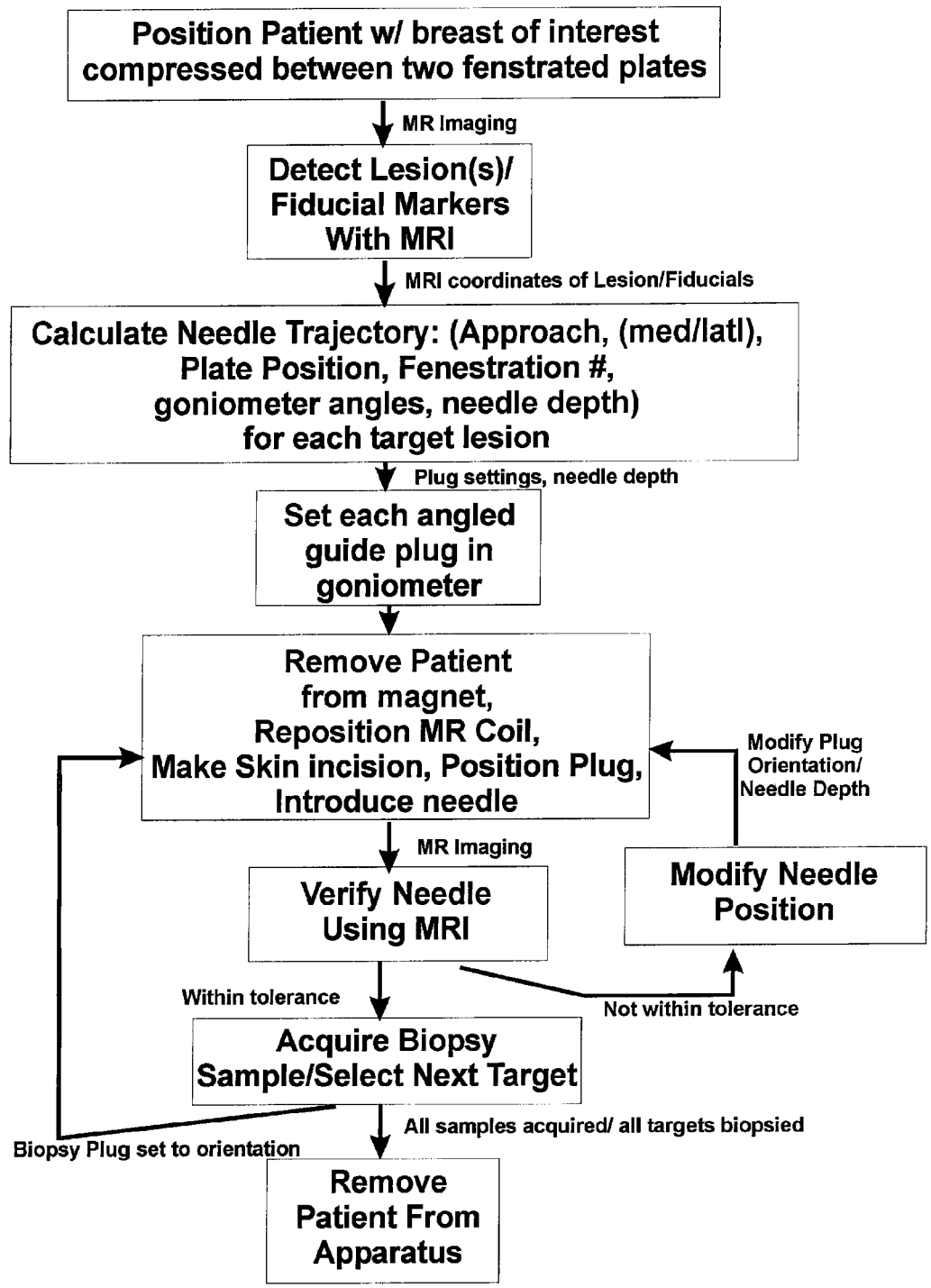
FIG. 26. Flowchart illustrating the MRI-guided core biopsy procedure according to the invention.

According to the invention, a core biopsy needle may be delivered to the breast on an oblique trajectory as illustrated in the flowchart shown in FIG. 26. A needle guide plug having straight (medial-lateral) holes of a larger diameter than the biopsy needle, or angulating guide plugs may be used in cases. Patient positioning with fenestrated plates and MR imaging is performed in an identical manner as described under MR-guided wire localization, with the option of implementing the various compression plates indicated in the diagram. Calculation of the needle trajectory is done using compound angles to define the needle trajectory and a goniometer is used to set the orientation of the guide plug. In cases where access to some targets is limited by the fenestration access, the fenestrated plate's position may be altered without moving the breast.

Introducer needle insertion is preceded by producing an incision in the skin at the center of the fenestration to facilitate needle entry into the breast. MR validation of needle position is performed before the biopsy sample is taken. In cases where small corrections in needle orientation are required, the guide plug gimbal can be unlocked and the needle orientation corrected by hand. In cases where a large correction is required, a new needle trajectory can be calculated based on the MRI validation images and a new guide plug orientation defined. In cases where multiple samples are required, multiple guide plug orientations may be defined in parallel with biopsy sample acquisition. Various systems in clinical use (Koebrunner 1999, Kuhl 1997) use angulated needle trajectories to acquire multiple samples, however this technique is unique in that the definition of the guide plug orientation is done away from the patient with the use of a goniometer. This enables multiple trajectories to be prescribed rapidly and accurately (currently in with an included angle of 60 degrees).

Example 3

MR-Guided Marker Placement

Figure 15:
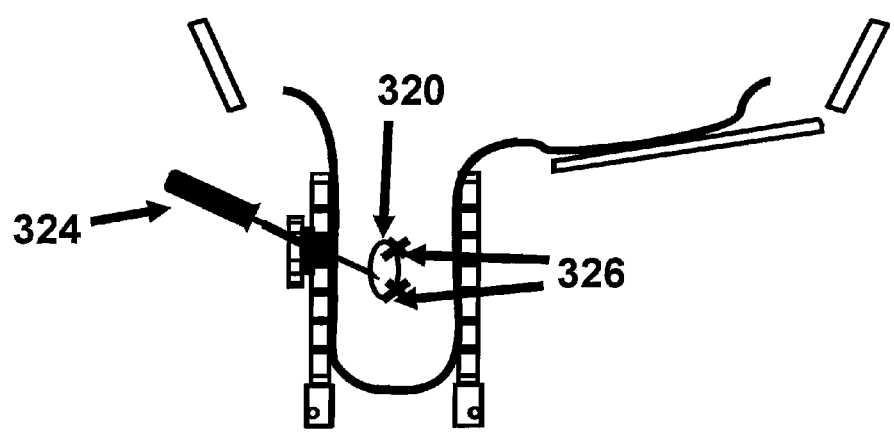
FIG. 15 illustrates the MR-Guided delivery of tumor boundary marking clips according to the invention
Figure 27:
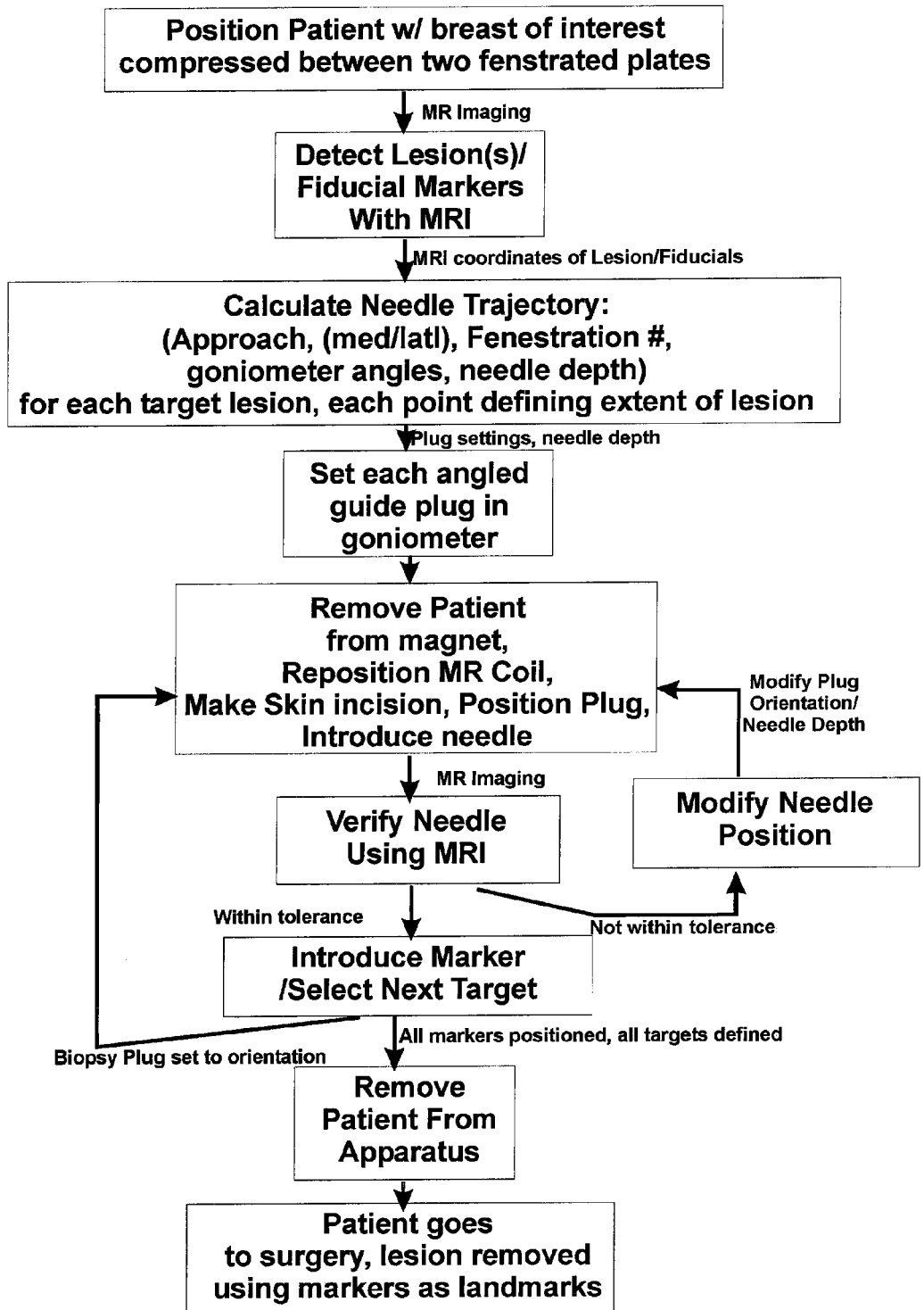
FIG. 27. Flowchart illustrating another embodiment of the MRI-guided core biopsy procedure according to the invention.

The concept of MR-guided biopsy presented in EXAMPLE 2 can easily be extended to placement of small position markers in the breast, according to the invention. This may or may not be done in conjunction with MR-guided biopsy, or done in conjunction with MR-guided needle localization. This application would take advantage of the fact that a large tissue segment can be accessed through a single incision point (repositioning of the fenestrated plate to provide better access may be required). As shown in FIG. 15, a linear tumor 320 can be delineated by way of a set of markers 326 These markers 326 may be identified after the procedure defining the maximal extent of the tumor. Markers such as endovascular occlusion coils, surgical clips, or any of the devices as disclosed by Foester et al. in U.S. Patent Application Ser. 2002/0193815 A1 may be used. Furthermore, radiotherapy implantable seeds, or local chemotherapy delivery devices may also be distributed around the periphery of the tumor. Clips can be delivered through the center of a hollow needle 324, and when fully extended and uncoiled, they remain fixed in the tissue at the end of the needle 324. These clips would have to be made of the appropriate MR-compatible material (e.g., titanium, platinum, stainless steel, etc.) to ensure they can be identified and do not compromise subsequent MR images, and to ensure they can be safely used within the MR magnet room. The use of this procedure according to the invention is illustrated in the flow chart shown in FIG. 27.

Example 4

MR-Guided Interstitial Therapy Delivery and Monitoring

In the method of the present invention, the techniques described above may be easily extended to deliver a variety of tissue investigation or ablation devices such as invasive ultrasound tissue ablation devices, RF-heating devices, cryotherapy systems, local delivery of chemotherapeutic agents, local delivery of radioactive material for therapy, optical ablation (lasers), optical photodynamic systems or any other tissue destruction technique. Monitoring of these devices may be done using MR imaging to measure temperature distributions, chemical concentrations or other parameters during therapy. In the case of the optical systems, the treatment region may be defined using other techniques (i.e. T2-weighted contrast sequences).

MR/US Hybrid Imaging and Intervention

With the system outlined above, an apparatus for delivering a device to a lesion is described with an arbitrary trajectory. However, the needle path may deviate from the planned trajectory due to either tissue heterogeneity which can cause needle deflection. A hard lesion and surrounding tissue may move during device entry. Further, the ability to biopsy small lesions can be limited due to the size needle-generated artifact on the MR images as previously mentioned. This is particularly problematic when preformed on a high field imaging system (i.e., greater than 1.5 T magnetic field strength). Ideally, a means to observe the needle path in real-time is optimal to ensure correct lesion penetration. According to the present invention, an ultrasound imaging capability can be added in the same biopsy apparatus in order to deliver a US transducer using the same stereotactic delivery strategy as outlined in the previous section. A device can then be delivered into the breast under the guidance of this real-time US imaging in several ways.

Through a simple modification to the biopsy system, removal of the compression plates and substitution with an acoustically transparent window held in a frame containing fiducial reference points, the invention can be used to perform hybrid (MR/US) imaging. This aspect of the invention involves detecting the lesion using MRI, than removing the patient from the MR magnet's intense field to perform US imaging. Using the system in this manner constitutes an automated strategy to identify MR-detected lesions in US images as well as a means of fusing MR and US images. The real-time US data can be used to position a device accurately into the lesion and to verify its position. This may be done using US exclusively when the lesion can be identified on the US image, or using a combination of the MRI and US data if the lesion is not easily identified using US, or if the patient may have moved.

The approach to breast imaging disclosed by the present invention has many useful clinical applications as generally demonstrated in the following examples. These applications can also be extended to existing MR and US imaging modalities (e.g. contrast-enhanced MRI/US, compound US imaging, US Doppler imaging, etc), or to those available in the future, without departing from the scope of the invention.

Example 5

Hybrid MRI/US Imaging

This application involves accurate location and assessment of extent of an MRI-detected lesion using US in the same procedure while the patient remains in the same apparatus that was used for MR imaging. This offers an alternative to retrospective US detection of MRI-detected lesions in two different procedures. This retrospective technique can be inaccurate and time consuming as the patient is in two very different configurations for both imaging procedures. This relies on the skill of the radiologist to mentally transform data from the two modalities. Hybrid MR/US imaging enables the radiologist to confidently identify MR-detected lesions using US which may allow them to improve diagnostic ability based on features visible under US. It also allows them to identify anatomical landmarks which can be used for subsequent US-guided biopsy with the patient removed from the biopsy apparatus. Knowledge of the US characteristics of the lesion could lead to easy identification of the lesion in a follow-up US examination. In cases where the lesion is difficult to identify on the US image, the option to view the lesion as an image where MR and US-visible features are combined.

Example 6

Hybrid Biopsy

This application of hybrid imaging involves biopsy acquisition under US-guidance while the patient remains on the biopsy table with their breast immobilized. The region of interest for US examination is identified using previously acquired MR images. This procedure involves stereotactic delivery of the US transducer in conjunction with free-hand, or stereotactic delivery of the biopsy needle. This may be augmented by the use of combined MR/US data set, and with or without the use of a US transducer whose position and orientation are measured in real-time, and/or tracked biopsy needle. This image can be superimposed onto the MR/US fused dataset in such a way that the needle is easily identified on the MR/US fused image set, and in a way that the presented MR/US image(s) updates with the changing position of the US transducer.

Example 7

Hybrid-Guided Marker Placement

In a similar manner as hybrid-guided biopsy, and in the same way as MR-guided marker placement differed from MR-guided biopsy, this system can be utilized to place numerous implantable devices to denote breast tumor extent. In this case the applicator needle placement will be performed using US-guidance and may be done either using free-hand applicator guidance or stereotactic needle delivery with the ability to correct for applicator and tissue deflection. In this case the fused MRI/US data may provide better determination of lesion boundaries than US guidance would give alone.

Example 8

Interstitial Therapy Device Delivery and Monitoring

The hybrid device delivery technique may also be used to deliver devices other than biopsy needles, or marker placement devices. This system can also be used to position a variety of tissue investigation or ablation devices, such as invasive ultrasound tissue ablation devices, RF-heating devices, cryoablative systems and, optical photodynamic systems as described previously. In many cases it is advantageous to monitor the therapy using the US images, particularly using cryotherapy. This technique may offer the ability to improve the accuracy of the delivery, was well as reducing the amount of MR imaging required. Again this can be done using the combined MR/US data set, or using only the US data if the lesion can be confidently identified on the US image. However, the use of the combined MR/US data may be beneficial as MRI may provide much better definition of tumor boundaries.

In all applications described above, US imaging modes (e.g. Doppler, 3D imaging, US contrast agents) may improve lesion detection. According to the invention, various means of image fusion can be used to assist in image correction in both the MR and US images.

For all MR/US hybrid imaging procedures set forth in Examples 5-8, standard apparatus may be used as outlined in the following section. The methods are useful for accurate location of the US transducer to all regions of breast tissue, transformation of coordinates between the MR and US imaging data, MR/US image fusion/integration techniques, MR/US image correction and reformatting. According to the invention, this equipment can be integrated with the biopsy system presented in the previous sections, (i.e. the patient support, biopsy table, compression system, MR imaging coils).

US Transducer Delivery

Figure 16:
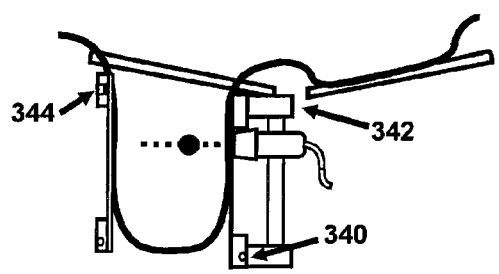
FIG. 16 illustrates the MR/US co-registration procedure which can be used according to the invention. The lesion and fiducial markers are identified using MRI. Based on the MRI information, an US transducer is delivered to the appropriate position so that the lesion is centered in the US image using a stereotactic frame.
Figure 17:
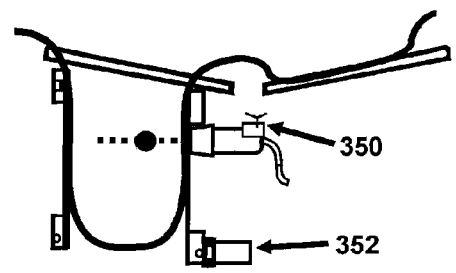
FIG. 17 illustrates the MR/US co-registration procedure where a free-hand US transducer positioning system may be used. A touch point is used to register the coordinate system of the tracking device to the fiducial marker defined, and therefore to the MR image's coordinate system.
Figure 18:
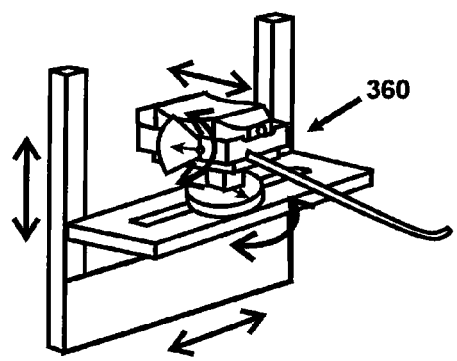
FIG. 18 shows different US probe delivery techniques which can be used according to the invention. Using a mechanical stage with 5 degrees of freedom, capable of fixing an US probe horizontally or on edge, allows accurate transducer positioning. Important features enable imaging near the chest wall (i.e. apparatus and structure do not encumber access to this region). a shows a frame with open central aperture and embedded fiducial markers that may be inserted into the compression frame to provide touch point reference to co-register the tracking system to the images.
Figure 18A:
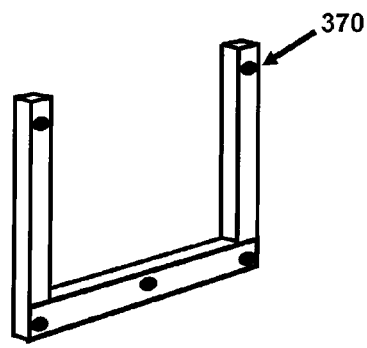
Figure 20A:
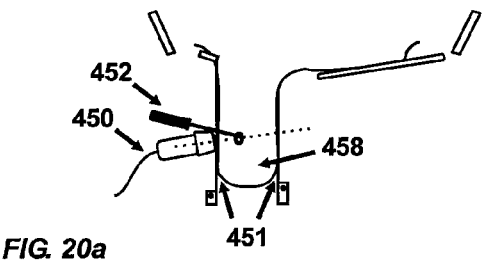
FIG. 20 shows various MR/US Hybrid biopsy configurations according to the invention. a shows the breast compressed between two sterile, US transparent plates. Imaging and intervention occur from the same side. b shows a configuration with one fenestrated plate and one US permeable plate. The needle approaches from the opposite side from US imaging. c shows a plate with larger fenestrations that can be used to introduce a transducer and needle for same-sided imaging and intervention. d shows transducer and needle delivery through the same side using a positioning stage.

Another aspect of the invention provides the ability to deliver an US imaging transducer to a particular MR-detected position in space using MR-detectable fiducial references. A US transducer holder and positioning apparatus is affixed at a known position relative to these markers. If the position of a target on an MR image is known relative to these MR detected markers, then the position of a US transducer relative to these same markers can be calculated such that the device and the corresponding US imaging plane can intercept that target. If the US imaging plane and field of view is known relative to the US transducer, then a transformation from MR to US image coordinates can be obtained. The devices involved include a constraint plate incorporating an acoustically permeable membrane to immobilize the breast, a stereotactic frame with embedded/attached fiducial markings 340 and attachment points 344 for a transducer positioning/tracking system 342. FIG. 16, FIG. 17, FIG. 18, and FIG. 18a show these components. FIG. 16 is the positioning stage where a mechanical stage with five degrees of freedom and capable of two different transducer orientations allows accurate transducer positioning. FIG. 17 is the tracking system with a free-hand position tracking device 350 and registration apparatus for free-hand tracking 352. FIG. 18 shows how a nest 360 may be positioned in two or more orientations. FIG. 18a shows touch points 370 at known positions relative to MRI visible fiducial markers to provide an alternative means of free-hand registration.

In the method of the invention, the function of the membrane is to provide a means to compress the breast as well as provide a window for US imaging. A polymeric membrane that is acoustically matched and is thin enough to not attenuate the US beam in a manner that affects US image quality is suitable (e.g., polyethylene, polystyrene, polyester, polycarbonate, etc.). It is important that the breast is well compressed and that the breast is coupled to the membrane (US coupling gel is applied between the breast and the membrane before the procedure begins). Designing the membrane such that it bends a small amount to conform to the curvature of the breast ensures that there is maximum coupling between the breast and the membrane. This allows maximum imaging access to the breast (FIG. 19a, b, c, d). Strategies to constrain the breast in other directions enable full access to all of the breast, including regions behind the nipple. In an initial presentation of this concept devoid of technical details, the anticipated implementation involved US imaging and intervention occurring on opposite sides of the breast (Plewes et al, 2001 IEEE Ultrasonics Symposium). This was the only presentation of this concept as Prior Art. However this simplistic embodiment without redesigned patient support for probe and needle angulation capacity and without a compression membrane and breast constraints in other orientations proved to be ineffective for clinical usage. The compression membrane configuration presented in FIG. 19 is key to providing complete access to the breast, and at first glance is not obvious. FIG. 19 a, 19 c show that lesion 402 is difficult to access with ultrasound (US) imaging with a taut frame holding the membrane 400 stiff. FIG. 19b and FIG. 19d shows compression with a larger, deformable membrane 404 that places more membrane in contact with the breast. In FIG. 19a and FIG. 19c, the two rigid frames 406 also make the breast difficult to access for US imaging, while in FIG. 19b, 19d the curvature 408 (as seen from below the breast) allowed with a less rigid or taut system allows the lesions 410 more accessibility in US imaging.

According to the invention, the US transducer holding and positioning system can take two general forms; 1) a mechanical stage, 2) a free-hand tracking device. Both techniques involve holding an US transducer in a conformal nest which is then attached to either a mechanical stage, or to a tracking device at a known position and orientation. A mechanical positioning system enables accurate positioning of the transducer with various degrees of freedom. This positioning system is then attached to the compression plate at a known position with the axes of USH motion corresponding to the MR imaging axes (L/R, A/P, S/I), and therefore to the physical frame of reference. This facilitates transformations between the MR frame of reference and the transducer frame of reference as well as eliminating the need to register the positioning apparatus to the stereotactic frame during the procedure. In the embodiment shown in FIG. 18 the transducer can be moved through 5 or more degrees of freedom. This design, with positioning tracks on the periphery of the breast imaging volume, enables access to areas near the chest wall, which is critical for complete access to the breast. The rotational axes of the positioning system further enable the transducer to be angled to image regions of breast tissue that would be inaccessible with a simple horizontal or vertical imaging approach. The design of this stage allows for large angulations of the transducer without interference. This device ensures that the transducer can be moved in the vertical (A/P) and horizontal directions (S/I) with the transducer face always in contact with the membrane surface. This allows for effective scanning through the breast volume, facilitating 3D US imaging applications and also enables a lesion to be inspected using multiple transducer orientations. This design further enables accommodation of various transducers during the procedure by interchanging the transducer nest. The position of the US imaging plane is known because the position of the transducer relative to the USH is known. The ability to easily remove US transducers from the USH allows the radiologist position the US transducer by hand. Once a lesion is identified in the US image, the US transducer can be removed from the nest and be manipulated free-hand. This allows visualization of the lesion through multiple imaging planes which is known to be a critical element of US imaging, however once removed from the nest, the position of the transducer is no longer known. There are no inventions presented in the Prior Art that pertain to a mechanical positioning stage for an US transducer accounting for the presented constraints.

The invention also provides another tracking option that more closely resembles the traditional manner of imaging with the US transducer; namely, a 6 degree of freedom tracking device (or other lower order degree of freedom systems) such as an optical (fiber optic), electro-magnetic tracking, ultrasonic tracking, or other non-contact position tracking system in which the transducer is free to move in space without fixtures. This aspect of the invention accommodates a technique which is more familiar to the radiologist; however, the accuracy with which the transducer can be free-hand positioned to a particular position may be limited. To use such a non-contact tracking system to determine transducer position relative to the fiducial markers, the orientation of the tracking system must be calibrated to the orientation of the stereotactic frame, and thereby to the MR image coordinates. This can be accomplished by positioning the transducer/receiver at points on the stereotactic frame at known positions relative to the fiducial markers, measuring these positions and determining a correlation to convert the tracking system coordinates to the corresponding MR coordinates and vice versa.

In another embodiment of the invention, an algorithm is applied which translates a given MR-detected coordinate to a corresponding USH position for a given US transducer in a given orientation (vertical or horizontal for the USH system presented in FIGS. 16, 17, 18 and 18a), such that the target of interest will appear in the center of the transducer imaging field at a calculated depth. A US imaging plane can be identified such that the shortest imaging distance to the lesion is selected, or to intersect the lesion using a specific transducer orientation. This algorithm enables conversion of a single MR-detected position to a set of USH axis-positions and a unique position on the US image. Techniques to register and fuse MR and US images (i.e. more than one corresponding point at one time) are explained in the following section.

Image Integration:

The present invention provides a method for registering MRI and US breast images (2D and 3D images) to various levels of sophistication based on accurate stereotactic transducer positioning and/or subsequent transducer position tracking. By knowing the orientation of the US transducer, a 3D MR data set can be reformatted to generate an MR image that corresponds to what is visualized on the US image (i.e. generate a 2D image from the 3D MR image set that is the same scale and size and corresponds to the same plane as the acquired US image). The actual transducer position can be determined by either the mechanical systems, or the non-contact transducer position measurement systems presented previously. Presenting the two images side-by-side allows the radiologist to validate that the lesion and surrounding structures in the US image correspond with the MRI data. Segmentation (image processing) and integration of the MRI data in ways to depict anatomical landmarks and functional information such as contrast agent uptake parameters would facilitate identification of the lesion and surrounding landmarks in the breast. This system can further be enhanced by non-contact position tracking of devices such as biopsy needles, or tissue ablation devices. Tracking the position of devices permits indication of the device position on this reformatted MR data and permits free-hand device delivery without guidance plugs or fenestrated plates. In addition, the real-time position-tracked US image of a device can be superimposed onto this image.

There are many tracking systems in the Prior Art related to the tracking of devices for the purpose of display and manipulation of medical images. In Comeau et al, (Med Phys, 27(4), 2000) a presentation of such an integrated system for the purpose of tracking an US probe relative to a patient's skull for the purpose of co-registration with respect to a set of pre-acquired MR images was presented. Here a method of optically tracking the US probe, and using US information to help correct for tissue shift errors associated with MR brain surgery was presented. The use of such a system to assist brain surgery is facilitated by the constraining nature of the boney skull. Such a concept has not been translated to deformable structures such as the breast as there has been no way to appropriately constrain the breast while providing adequate access required for intervention. Furthermore, the procedural difficulties associated with previous attempts have precluded its further development. An integrated system as presented in the invention enables application of image co-registration techniques in a way that is clinically practical.

Similarly, according to the invention, MR data can be displayed with a superimposed marker indicating the position of the scan plane of the US transducer. Visualization strategies such as maximum intensity projection could be used to effectively depict the 3-D MR data in a way the radiologist can clearly interpret. Furthermore, four-dimensional, or time series data could be combined and presented as a 3 dimensional color-coded representation. This technique would be most useful when a free-hand tracking system is used for the transducer.

In the method of the invention, the same concept of image registration and image integration could be extended to modify the real-time US images. Segmenting the critical structures from the 3D MR data (i.e. anatomical landmarks, contrast-enhanced lesion), and knowing the position of the transducer relative to the MR data by way of a tracking system, the two image modalities could be integrated into one image. This technique does not require the lesion to appear in the US image. Rather the MR image of the lesion is identified as the target and is superimposed on the US image. The radiologist could simply adjust the transducer until the superimposed lesion appears in the US image, and guide a needle to that point at a trajectory determined using knowledge of the transducer position. Similarly, the image may include a superimposed marker representing a position-tracked device to assist in its visualization. Image fusion in this manner will also permit a quantitative measure of the accuracy with which the images have been combined. A measure of how well the MR and US modalities are registered can be obtained by performing a cross correlation calculation at any time. The radiologist can ensure that the registration is accurate before proceeding with the intervention. In the method of the invention, the integration of 3-D MRI and 2-D US information and the overlay of segmented data (data which has been processed to highlight anatomical features), needle position and US image plane orientation enables real-time tracking of the needle position and US beam path to facilitate real-time guidance of a device towards a target by ensuring they are co-aligned throughout the imaging/intervention procedure.

There is no known Prior Art presenting a system that incorporates these technologies so as to provide an MRI/US combined approach to perform intervention, or imaging procedures on MRI detected targets in non-rigid regions of the body that are required to be constrained to reduce errors associated with motion and deformations. The physical and mechanical restrictions associated with such an invention have been presented as aspects of the invention thus far.

Image Error Correction:

The present invention also provides for integration of MR and US data, whereby information from one modality can be used to correct errors associated with the other modality.

Correction for US Positional Errors

Another aspect of the invention provides image integration techniques, whereby MRI data can be used to correct for errors in the US data set. It is well known that the location of features in a US image is determined using known values for the average speed of sound in tissue. However, fat and fibrous tissues are known to exhibit speeds of sound that differ by 5-10%. In routine US images, a fixed speed of sound is assumed to determine location. This is an approximation and will result in positional errors in the co-registration of the MR and US data sets. For example, if the space between the skin surface and the lesion is composed of purely fat and represents a thickness of ~3 cm, then the location of the lesion in the US image would be in error by approximately 1.5-3 mm and as such the MRI and US images would not be accurately co-registered. In most applications of US imaging, this is not a limitation, as relative position is often all that is required. In the method of this invention, absolute position in terms of an MRI coordinate frame is what is required. In practical terms, the main effect of the assumption of constant US speed-of-sound will be to distort the image in the direction parallel to the sound propagation, causing the image to be either compressed or expanded depending on the assumed speed of sound. However, refraction together with the fact that each point in the image is formed by multiple RF measurements from each element in a typical US transducer can lead to lateral distortions as well. This will be evident on the US image as spatial errors or regions of misalignment as one attempts to overlay the US and MRI image. In order to overcome these distortions corrections for the actual speed-of-sound for each transducer element must be made reflecting the actual tissues through which the US field propagates. Two possible approaches can be taken to overcome this limitation.

An approach is to attempt to correct for speed of sound variations by combining the MRI and US data. This can be achieved in an interactive fashion by repeatedly correcting the US data on the basis of knowledge of the tissue composition from the MRI data. In its most simple form, the MRI data can be used to make a first order correction of US position by estimating the amount of fat and fibroglandular tissue through which each US measurement is made. We note that standard T1-weighted MRI images render fat and fibroglandular tissues with very different signal intensities. Typically, fat appears with a high signal level (bright) as a result of a short spin-lattice (T1) time constant while fibroglandular tissues with longer T1 times, exhibit a lower signal and are seen as a dark region on the image. One this basis of this contrast between these two tissues, it is straightforward to segment the varying regions of the MRI data from which to calculate the distant of US propagation (and speed) for both fat and fibroglandular tissue. As the location of the US transducer has been positioned over the tissue on the basis of measurements from the MRI image, we know the position of the US transducer in the MRI imaging field to first order. From this the corresponding paths of the US field for each US transducer element can then be determined for each point within the US image. By referring to the same point on the MRI data the path length of the fat and fibroglandular tissue can then be estimated and the corresponding speed of sound variations for that location and US transducer element can be determined. This can then be used to scale the all the US RF data to the varying speed of sound within the tissue. The corrected RF data can then be combined to form the US image and create a corrected US image. This corrected image will represent a first order correction to align the US and MRI data. When attempting to overlay the US and MRI images, the boundaries of well-defined anatomical structures, such as interfaces between fat and fibroglandular tissue, should be better coregistered.

As a result of this operation, each point in the corrected US image will now be closer to its true location within the US image. This same process could be repeated in an interactive or interactive manner with each successive iteration moving the points in the US image to gradually migrate to their true corresponding location on the MRI data.

The discussion above, presumes that the geometry of MRI data is geometrically accurate; however, it is known that various factors will make the MRI image also exhibit spatial distortions. The most significant of these are positional errors arising from magnetic field gradient non-linearities. Most manufacturers of MRI equipment attempt to provide some form of correction for these gradient non-linearities on the basis of pre-determined measurements of the gradient spatial performance over the 3D imaging volume. In order for the segmentation scheme outlined above to be most effective, correction of MRI data is needed.

An alternative approach to this problem is to use image co-registration methods to map the US data to the MRI data. A number of co-registration methods exist which transform the location of point with one image to best match its location in another by satisfy varying metrics of image similarity such as mutual information (Hill D L, Batchelor P G, Holden M, Hawkes D J Medical image registration Phys Med Biol. 2001 March; 46(3):R1-45.). With these techniques it would be possible to correct for subtle changes arising from variations in the speed of sound in the US images and match them to MRI images. As such, lesions which are expected to appear on the US images can be determined uniquely from MR image. In addition, we could use the calculated deformation field to calculate the speed of sound variations that would be needed to generate this deformation in an iterative manner similar to that described above. As such, the MRI data will be used to constantly update the US data in real-time to provide accurate co-registration of the two data sets.

Defining the MR Image Plane to Track US Transducer Motions

A further aspect of this invention uses motions detected with US data during an intervention to modify the MR image, reflecting the new tissue geometry. The MRI image would appear to be updated in a real-time manner, without necessitating acquisition of new images in the MR magnet. In the method of the invention, the entire post-MRI imaging operation could be done outside of the magnet room by detaching the transport stretcher from the magnet and rolling the patient out of the magnet's field. This would reduce the amount of time needed for MR magnet access but ensure that meaningful use of the MR images would be made during an intervention. Further embodiments include gathering 3D US data (rather than the normal 2D images) during intervention to monitor tissue and device motions. Another embodiment involves measuring the orientation of the needle from an external tracking system to overlay this estimate of device orientation on the image data. This would serve to corroborate the device orientation with that visible on the US image, helpful when the device position is unclear in the US image. Furthermore, US imaging serves to reduce the need for further MRI.

As mentioned previously, Cormeau et al, 2000, presented a system that integrates US and MRI data registered using fiducial points and with probes positioned and tracked using an optical tracking system. This embodiment has been specifically developed for brain applications and does not translate to breast applications for reasons previously mentioned. Tissue shift correction techniques presented by Cormeau using information from both modalities can be translated to the breast application. The current invention differs in that a well-immobilized breast with US imaging access provided through multiple access points (medial and lateral) enables high quality US imaging (shortest distance imaging to the target) to be performed without gross tissue motion associated with craniotomy associated with neurological procedures. The current invention also considers the nature of imaging errors associated with mis-registration errors not considered by Cormeau.

Additional Examples Of Clinical Applications Of The Invention

Example 9

Hybrid MR/US Imaging

Figure 28:
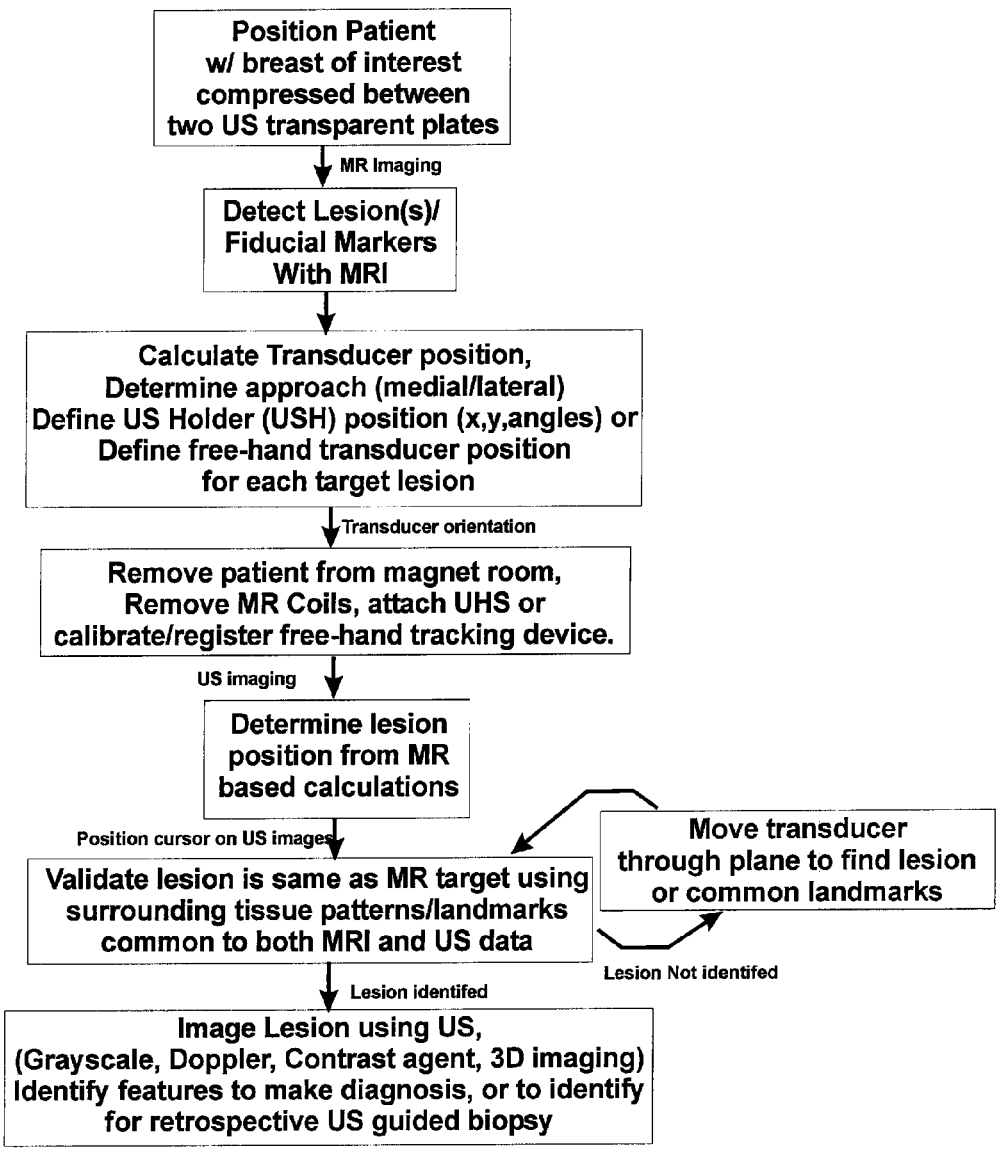
FIG. 28. Flowchart illustrating the hybrid MR/US imaging procedure according to the invention.

The simplest implementation of hybrid imaging involves the detection of a lesion using MRI, followed by positioning of an US transducer, such that the lesion appears in the center of the US field of view at a calculated position, as illustrated in the flowchart shown in FIG. 28.

The breast of interest would be compressed between two acoustically transparent compression plates. Attached to these compression plates would be an array of coils for MR imaging. The lesion would be detected using MR imaging techniques and other MR imaging techniques may be used to identify features of the breast that would be visible using US. This would serve to provide features common to both imaging modalities (e.g. T2-weighted MR imaging is appropriate for imaging cysts, T1-weighted for fat-fibroglandular interfaces). The position of the target lesion and the fiducial markers as seen on the MR image would be entered into a computer program which determines the appropriate USH co-ordinates such that the lesion will appear in the US image. The ability to image from medial or lateral sides of the breast without prior knowledge of the lesion position ensures optimal images may be obtained from the side closest to the lesion. After finding the lesion under MRI, the patient is transported from the MR imaging system while still immobilized on the patient stretcher, away from the magnet's field. At this point the MR imager is free to be used for another patient. The MR imaging coils are then removed from the compression plates and the mechanical, or freehand US position tracking system may be attached. The transducer can then aligned with the lesion as indicated by the MR image. The lesion of interest should appear at the center of the US image, at a calculated depth from the surface of the imaging face. Lesions can then be freely examined using a variety of US techniques.

In some cases, the lesion may be difficult to visualize in the US image, or the position prescribed for the US transducer may be in error for various reasons. In these cases, additional techniques can be applied with some increase of complexity. The techniques of MR/US image fusion/integration and image correction may provide the radiologist with tools to aid in identifying the lesion and provide more accurate registration between the images. Freehand transducer positioning provides a means of visualizing the lesion in three dimensions by imaging it through different planes. One important technique involves the identification of common features found in MR and US images in order to confidently identify the lesion.

In FIGS. 20 and 21, various MR/US Hybrid biopsy configurations are shown. In a lateral biopsy approach in FIGS. 20a, b, c and d, a breast 458 (for example) is compressed between two sterile, US permeable plates 451. Imaging and intervention occur from the same side. FIGS. 21a, b, c and d are essentially the same configuration as FIG. 20, with a medial biopsy approach selected. FIG. 20b is a configuration with one fenestrated plate and one US permeable plate. Needle approach is from the opposite side from US imaging. FIG. 21b is the same configuration as FIG. 20b with a needle guide plug used to deliver needle. FIG. 20 c uses a plate with larger fenestrations which can be used to incorporate a transducer and needle for same side imaging and intervention. FIG. 21c is the same configuration as FIG. 20c showing a view from a lateral side. FIG. 20d shows an alternative transducer and needle delivery through the same side using a positioning stage. FIG. 21d is another embodiment with 2-point needle positioning system on opposite side to US imaging.

A radiologist may use the information in the registered MR/US images to determine the pathological status of the tissue in question. For example, a breast lesion may be defined as malignant or benign based on well-understood features visible in the US image such as lesion morphology, or blood flow characteristics. The radiologist may also identify unique features of the lesion such as its appearance, size or location relative to anatomical landmarks in order that it may be identified on a subsequent retrospective US-guided biopsy.

Example 10

Hybrid Biopsy

A preferred embodiment of the hybrid imaging technique disclosed by the present invention is its application in acquiring biopsy samples of lesions that are detected using MRI and cannot be biopsied retrospectively through any other traditional means (e.g. if the lesion is not identifiable on the basis of US alone). Biopsy would then be performed making use of hybrid imaging.

Figure 29:
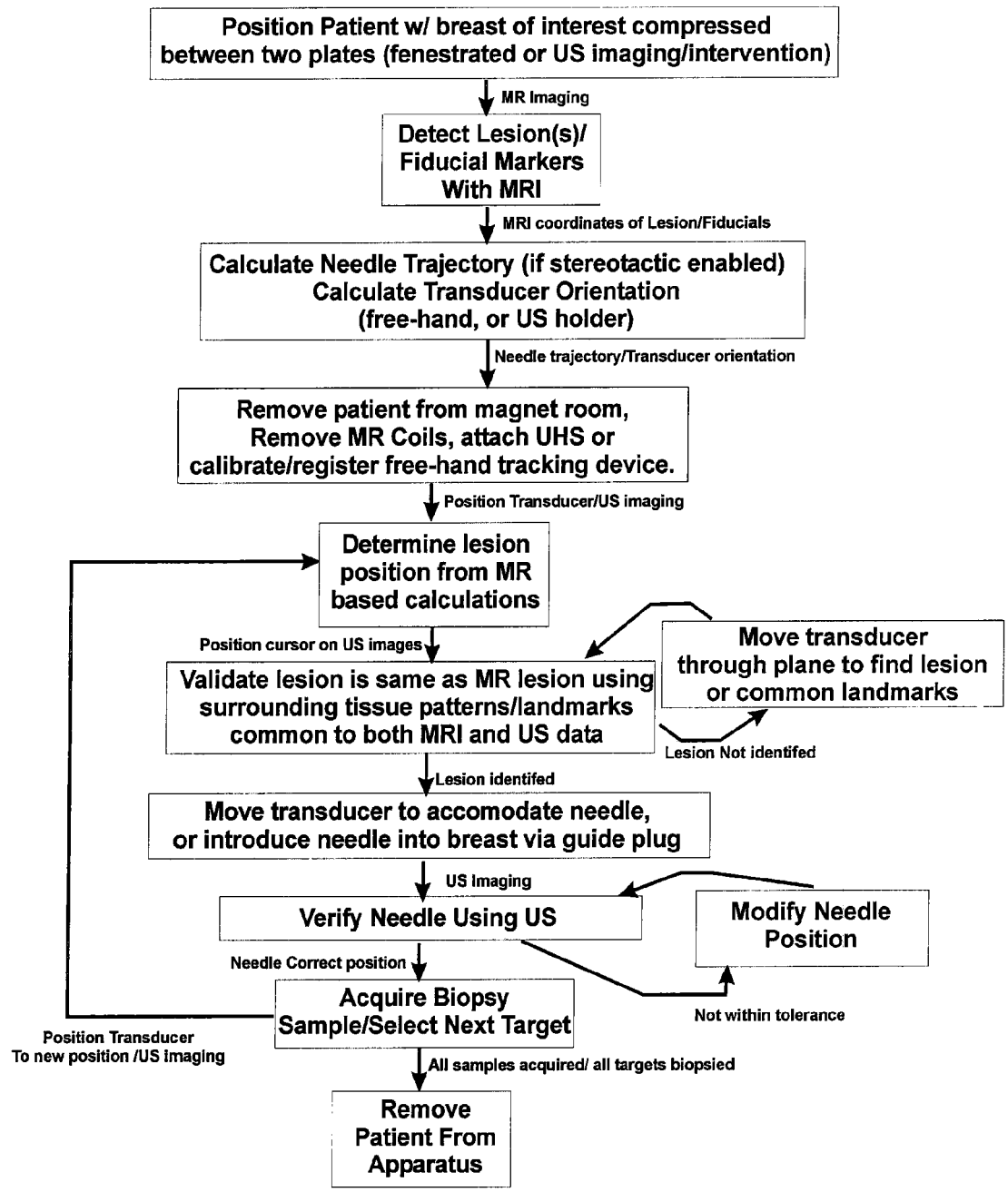
FIG. 29. Flowchart illustrating the hybrid-guided core.

According to this invention, the procedure for hybrid biopsy is similar to that for hybrid imaging, but in addition a biopsy needle would be introduced into the breast with US verification imaging. The general procedure is illustrated in the flowchart shown in FIG. 29.

This procedure requires the same apparatus as the hybrid imaging procedure, except the compression plates used would differ and a needle guidance strategy and apparatus may be incorporated into the procedure as required. Various setups for the procedure are shown in FIG. 21 and FIG. 22. In all cases shown, the contralateral breast is compressed against the chest wall. However both breasts can be constrained between plates and biopsied if both breasts extend into the interventional volume below the patient support. This would limit the biopsy approach to a lateral approach on either breast.

Figure 21A:
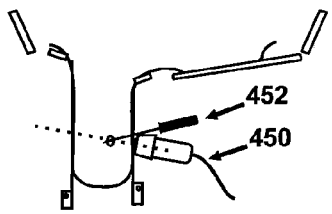
FIG. 21 Illustrates various MR/US Hybrid biopsy configurations according to the invention. a shows the breast compressed between two sterile, US permeable plates. Imaging and intervention occur from the same side with a medial approach b illustrates a configuration with one fenestrated plate and one US permeable plate. Needle approach selected opposite side from US imaging. c shows a plate with larger fenestrations that can be used to incorporate a transducer and needle for same-side imaging and intervention. d shows an embodiment with 2 point needle positioning system on opposite side to US imaging.
Figure 21B:
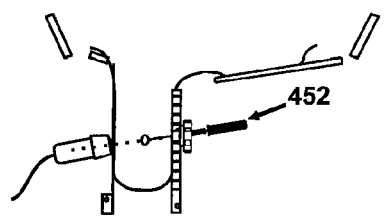
Figure 21C:
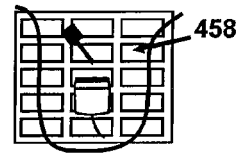
Figure 22:
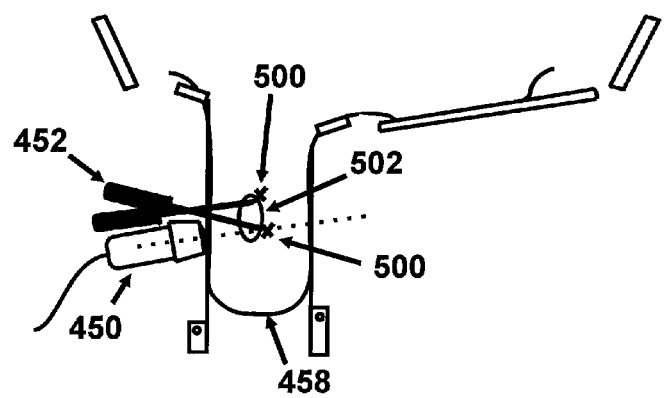
FIG. 22 Shows hybrid device guidance for delivering multiple markers in the breast to demarcate tumor boundaries using various compression plate configurations. According to the invention, this can be performed in an analogous manner to MR-guided marker placement.

In each of the configurations shown in FIGS. 20 and 21a, b, c and d, the compression plates have electrical connections for MR imaging coils (connections not shown). MR imaging is performed to detect the tumor and breast's features along with fiducial markers. The relative positions fiducial marker and target lesion are used to determine appropriate USH axis positions, bringing the US imaging plane through the lesion. After this point the biopsy techniques employed differ according to the particular strategy used.

According to one aspect of the invention, the breast of interest would be compressed between two US-transparent compression plates, as shown in FIGS. 20 and 21 a, b, c and d. These plates would be prepared with a sterilized membrane, as well as requiring that the coupling gel between the membrane and the sterilized breast would be sterile. Such a compression system presented as a sterile surface and an acoustically transparent member has not been presented in any Prior Art and is fundamental to the success of such a technique. After lesion detection, an appropriate US transducer position would be determined such that the following criteria are satisfied: i) the shortest imaging distance is selected (either medial or lateral approach) ii) transducer position provides clearance for biopsy needle entry and avoidance of biopsy system components, iii) the transducer orientation is optimized for lesion visualization. The transducer may be delivered to the appropriate orientation using the USH device and/or a free-hand tracking technique. The transducer positioning technique that provides the greatest access to the breast for needle positioning is preferred. The access provided by the system to the breast further enables the option of freehand US imaging with one hand from one side of the breast, and needle positioning from the other side of the breast. This configuration may not be optimal from the standpoint of the radiologist's dexterity, however this approach option is provided in one embodiment of the invention. The approach shown in FIGS. 20 and 21 with needle delivery and US imaging from the lateral approach would be used when the lesion is positioned in the lateral region of the breast. The approach shown with needle delivery and US imaging from the medial side of the breast would be used when the lesion is located in the medial region. In all cases the lesion would first be identified on the US images using the techniques previously presented. When identified, the transducer would be positioned so as to provide room for needle entry, or positioned so as to monitor the needle as it is introduced into the breast. In cases where the lesion is not obvious, addition of MR/US fusion strategies could be applied. Further application of needle tracking and presentation on the fused image set would also be of great benefit in this application as well as all other hybrid imaging strategies to assist in needle identification.

In another embodiment of the invention, the breast would be compressed between one US-transparent compression plate and one fenestrated plate on the opposite side, as illustrated in FIGS. 20 and 21. It is customary to select the shortest biopsy trajectory in order to minimize breast trauma. In this configuration the hybrid biopsy concept can be performed in a variety of ways, each using the basic concept of US transducer positioning and either free-hand needle delivery or stereotactic needle delivery. These techniques are described below, in accordance with the invention.

1) Stereotactic US Transducer Delivery, Freehand Needle Delivery

The lesion and fiducial are located using MRI. The patient/biopsy apparatus are removed from the MR imager and apparatus prepared for US imaging and needle intervention. The US transducer would be delivered according to MR image coordinates, and the lesion is identified on the US images. The US transducer may be repositioned to aid in identifying the lesion. On the opposite side of the breast, the appropriate aperture of the fenestrated plate is selected for needle entry using knowledge of the lesion's position. The needle would be introduced into the breast and its trajectory modified based on the US images. A biopsy sample would then be acquired the guide needle is in the appropriate position. Multiple samples may be acquired using, offsetting the biopsy needle's position for each. Multiple lesions may also be examined in the same breast, in the same procedure using this strategy.

2) Stereotactic US Transducer Delivery, Stereotactic Needle Delivery (No MR Verification)

This embodiment of the invention is similar to the one proposed above, differing only in the extent to which the MRI data is used to help position the needle and transducer. The lesion and fiducial markers would be identified using MRI. These positions would then be entered into a program that would determine the appropriate needle delivery trajectory based on the shortest distance to the lesion, or restricted to a fenestration selected by the radiologist. Based on the needle orientation, the transducer orientation would be calculated such that the needle would appear in the plane of the US transducer as it is introduced into the breast. The patient would then be removed from the magnet bore, and prepared for US imaging. The US transducer would be positioned according to the above calculation and the lesion identified on the US image. The needle would be introduced into the opposite side of the breast through the needle guide plug and its trajectory modified based on the MR or US verification images. The guide plug may be loosened and the needle trajectory modified as required. Multiple samples may be acquired.

3) Stereotactic US Transducer Positioning, Stereotactic Needle Delivery (MR Verification)

In a third embodiment of the invention used with this plate configuration, MRI is used to detect and to validate the needle position before the US imaging procedure is performed. The lesion and fiducial markers would be located using MRI. The appropriate needle delivery orientation to the lesion would be calculated based on the MR data such that the shortest distance to the lesion would be selected (also considering the positioning of the US transducer and limitations of the apparatus in the immediate area). An MRI compatible needle would then be delivered to the lesion at the desired orientation using the angled needle guide plug presented previously. MR imaging would then be used to validate needle position. The needle position may be modified as required with additional MR imaging. The patient would be removed from the MR magnet room and the apparatus setup for US imaging. The US transducer would be positioned to an appropriate orientation to allow the needle and lesion to be imaged. The needle trajectory may be modified as required by unlocking the needle guide plug before the biopsy sample is acquired.

The examples presented above are all embodiments of the invention. Each embodiment has certain advantages. For instance, one embodiment requires the operator to deliver the needle by free-hand guidance. This strategy is a fast technique requiring no needle guidance apparatus, however it relies on the radiologist's dexterity. A second embodiment (employing stereotactic needle delivery outside the MR magnet) requires more apparatus; however it provides a fast means of needle delivery and has fewer demands for accuracy on the radiologist. The third embodiment, which requires MR-verification of the needle before US imaging/needle verification is a longer procedure, however it does provide an additional MR image as verification. The last embodiment is limited in that the patient must remain in the prone position with the biopsy needle in the breast for a longer period of time.

In another aspect of the invention, fenestrated plates that have openings large enough to accept either the front end of an US transducer, or a biopsy needle, or a needle guide plug, are positioned as medial and lateral compression plates. This configuration enables imaging and intervention from either medial or lateral approaches. This configuration further enables free-hand biopsy, or stereotactic needle delivery techniques. The design of the plates should be such that the openings are large enough to allow the transducer access to the breast, however not large enough that a large volume of breast tissue bulges through the openings. According to the invention, an acoustically permeable membrane is pulled taut and positioned between the breast and the fenestrated plate can be used to constrain the breast in this implementation. This has the benefit of good breast immobilization, good access for US imaging, and provides a frame to which needle positioning plugs may be attached.

Figure 20B:
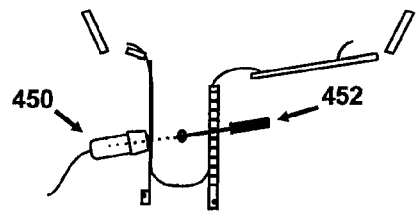
Figure 20C:
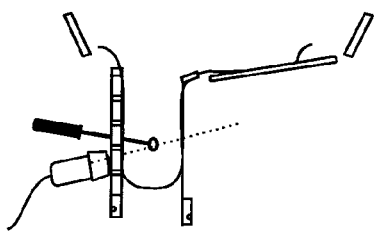
Figure 20D:
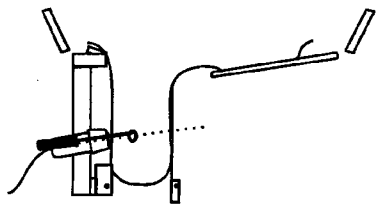
Figure 21D:
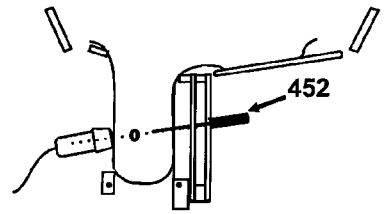

In yet another aspect of the invention, two different needle positioning strategies are applied. The implementation of the two-point needle positioning device corresponding to the US transparent membrane is shown in FIGS. 20*d* and 21*d*. This can be used on either the same side of the breast as the US transducer or, as shown here, on the opposite side. In FIG. 21*d* we see an additional needle guide attached to the US transducer positioning device.

In all of the above hybrid biopsy strategies, the lesion may not be visible to US. In some cases the lesion may not be identifiable due to poor US image contrast. In these cases, the operator may choose to biopsy the tissue identified by the MR images. A biopsy may be acquired more confidently if image fusion techniques are employed. According to the invention, other imaging techniques, including US Doppler, Harmonic and US micro-bubble contrast, may be used to enhance the quality of the images acquired. In the method of the invention, all biopsy strategies can be extended to multiple lesions in a single procedure. None of these techniques have been described in detail in previous Prior Art. An article by Plewes 2001, IEEE, presents a simplistic form of the technique where US and needle delivery is performed from opposing sides with the shortest distance taken to be from the needle insertion to lesion center, however none of the enabling aspects of the invention were presented.

Example 11

Hybrid Marker Placement

According to the invention, using a technique similar to MR-guided biopsy of the breast, a small position-marking device may be implanted in the breast in conjunction with a biopsy or wire localization procedure. Any of the previously presented hybrid biopsy techniques could be applied as needed. Marker placement using MR-guidance alone would require multiple image acquisitions to verify position prior to each marker placement. Lesions only visible under contrast enhancement cannot be imaged repeatedly with MRI during the same procedure. Guidance of marker placement devices using US is not restricted by time-limited lesion contrast enhancement, and does not require long periods of expensive MR magnet time. US cannot always be relied upon to visualize a lesion's exact location or extent, but can be used to track tissue motions during the intervention. In this technique, MR images are reformatted to reflect the changing image plane of a US transducer, and modified in real-time to indicate tissue distortion detected with US. This confers the ability to image in real-time with ultrasound, but to still visualize lesions to the extent possible with MRI.

The marker placement device's position would be known from both the US data and from a separate position tracking system. A representation of the device's location would be overlaid on the reformatted MR image described above. Markers may then be positioned relative to a lesion as it appears on MRI, but whose morphology is being updated based on US monitoring.

Figure 23:
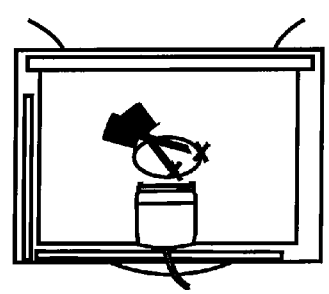
FIG. 23: Hybrid needle guidance for positioning of multiple markers in the breast to define tumor boundaries demonstrated from the physicians point-of-view.
Figure 30:
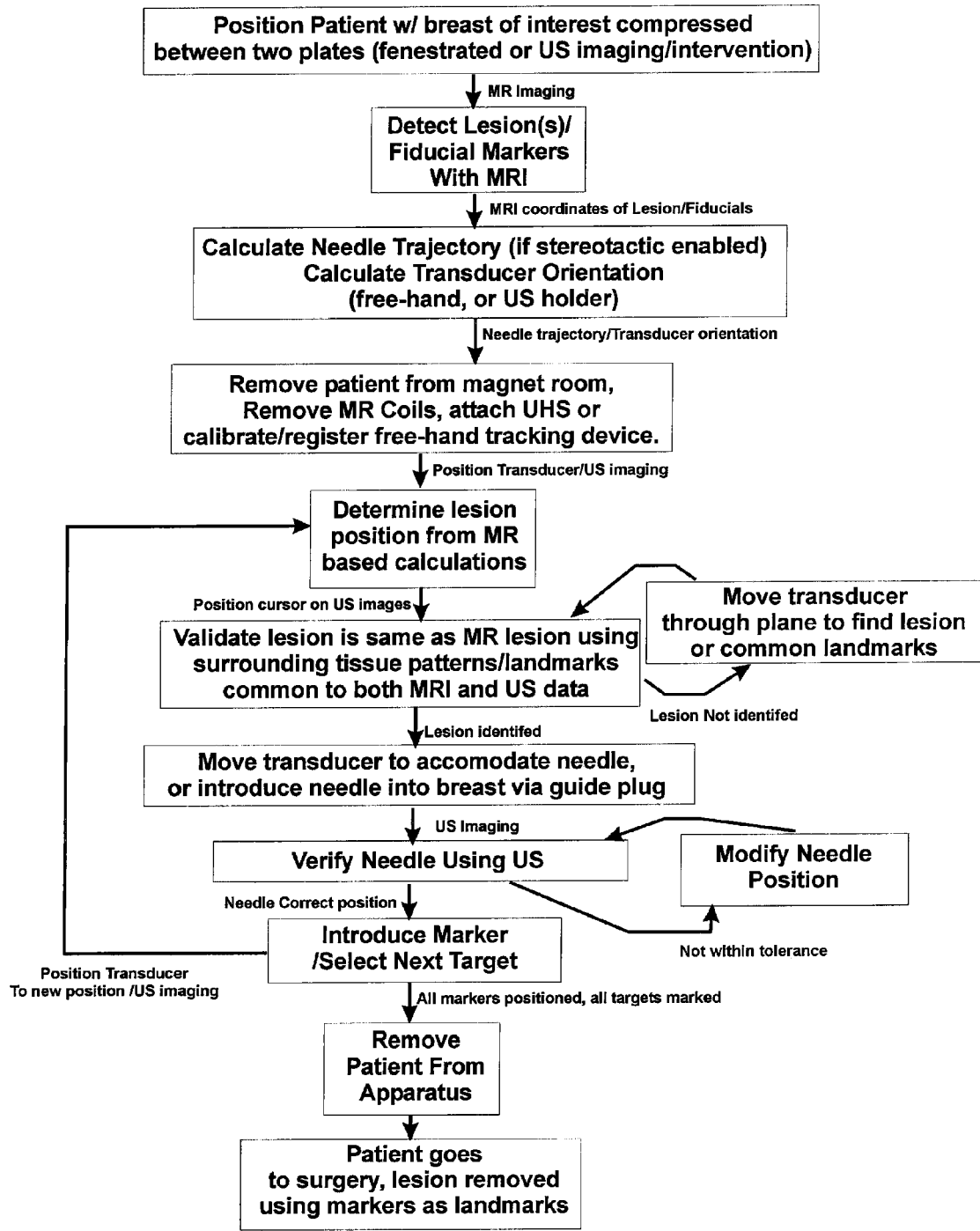
FIG. 30. Flowchart illustrating the hybrid-guided marker placement procedure according to the invention.

According to the invention, these markers do not have to be made of MR compatible materials. In one embodiment, they are constructed of materials and geometries that are easily identified on US images (highly US reflective scattering). In another embodiment, these markers are made of MR compatible materials so that their positions may be verified relative to the lesion enhancement pattern on subsequent MR imaging procedures (e.g. supine MR imaging may be preferable, in order to locate markers with the patient in the position used for surgery). This procedure is demonstrated in FIG. 22 and FIG. 23 and in the flowchart shown in FIG. 30. Marker placement under mammography, ultrasound and MRI have been presented in recent years, however multiple marker placement, and MR/US combined marker placement have not been presented in the prior art. FIG. 22 shows the positioning of multiple clips 500 at a lesion 502 in a breast 458 by devices 452 guided by transducer 450 from a medial perspective. FIG. 23 shows an image of the devices inserting the markers from the physician's point of view.

Figure 24A:
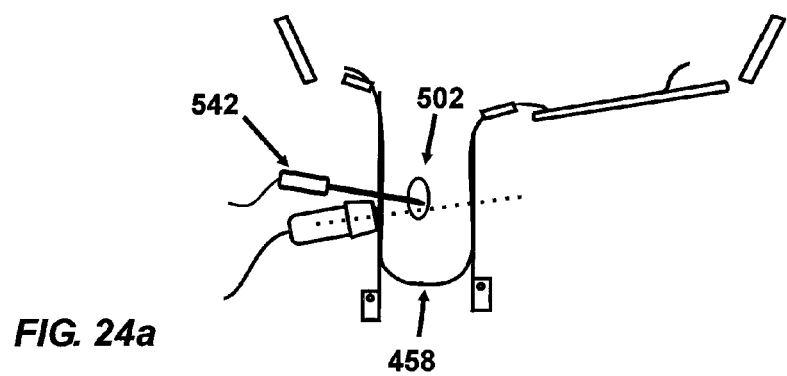
FIG. 24a According to the invention, hybrid needle guidance can be used to position tissue ablation probes and monitor therapy progression. In this example, a cryoablation probe can be positioned to the center of the lesion using hybrid guidance. b shows how reformatted MR images may be used to define the tumor extent, while US may be used to monitor ice the development of the resultant ice ball.
Figure 24B:
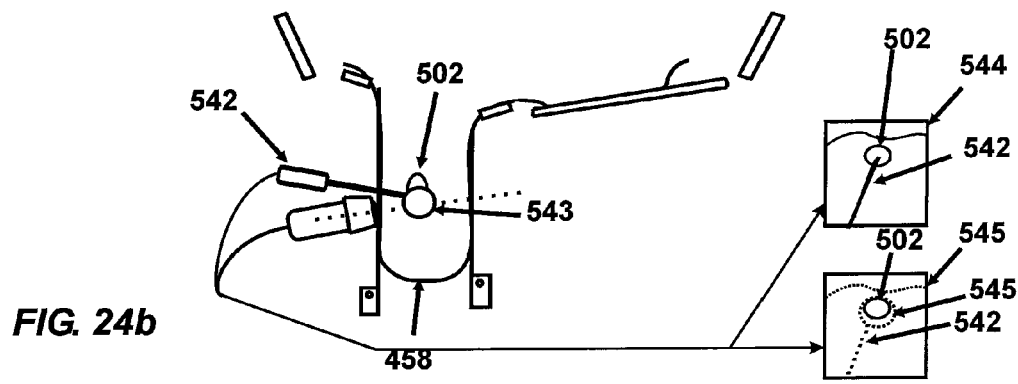

FIG. 24*a* shows that hybrid needle 542 (e.g., tissue ablation probe such as a cryotherapy probe) may be delivered to a lesion 502 in a breast 458, with delivery made in multiple positions based on MRI imaging. In FIG. 24*b*, it is indicated that therapy can be monitored with US and/or corresponding MR data as a US image 545 or reformatted MRI image 544. A lesion 502 may be segmented from the MRI data through various means, with probe position 542 and tissue architecture demonstrated in the reformatted MR image 544. The corresponding features may be present in the corresponding US image as an US visible lesion 545 with or without fused MRI data to assist in validation of lesion position and/or probe position.

Example 12

Hybrid Monitoring of Therapy Delivery

Figure 31:
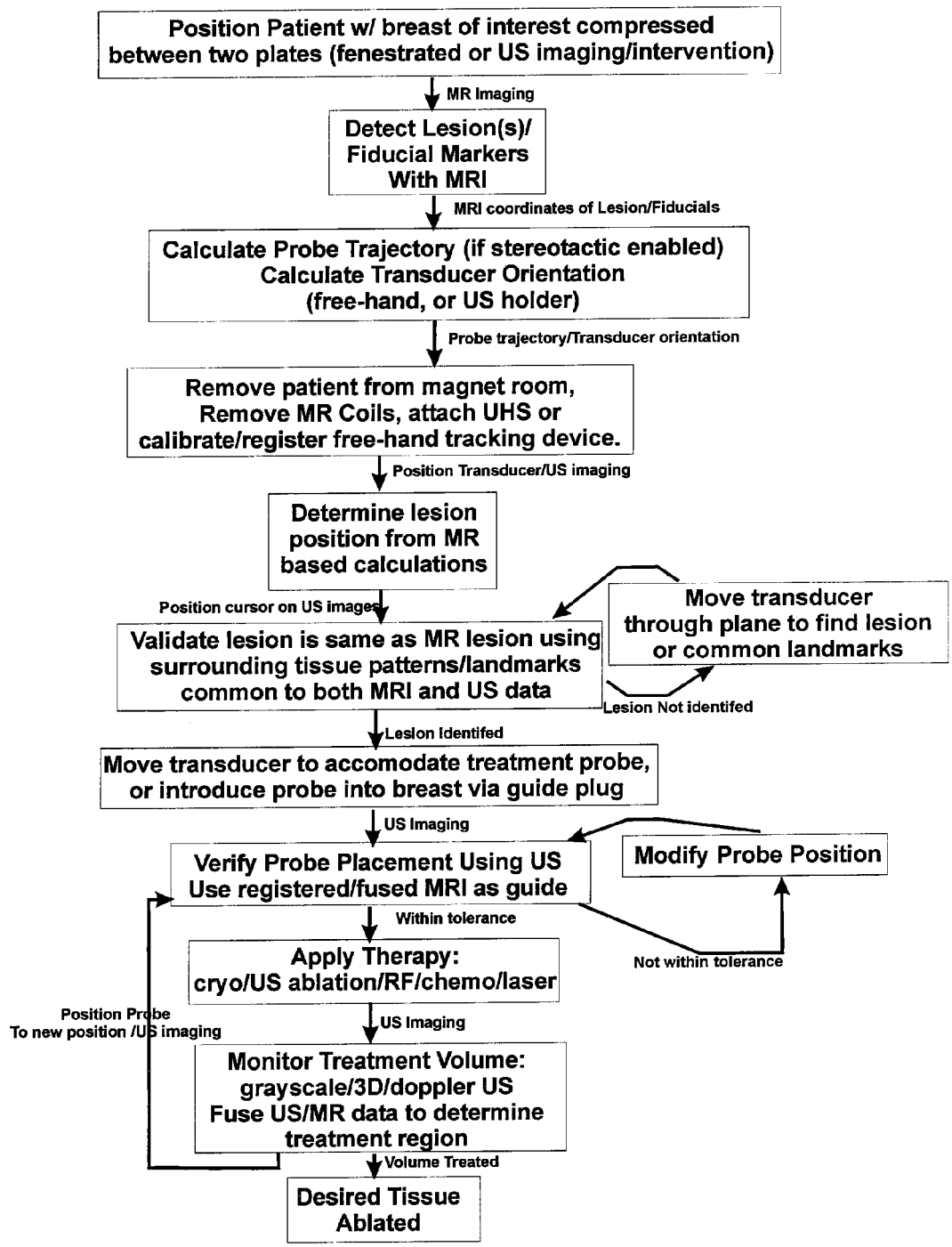
FIG. 31. Flowchart illustrating the hybrid-guided delivery of tissue ablation probes and monitoring of therapy according to the invention.

According to the invention, this system can be used to accommodate a variety of tissue investigation or ablation devices, such as invasive ultrasound tissue ablation devices, RF heating devices, cryotherapy systems, local delivery of chemotherapeutic agents, optical ablation (lasers), optical photodynamic systems, or any other tissue destruction technique. Monitoring of these therapies may be performed using the position-tracked US transducer with imaging techniques such as standard grayscale imaging, Doppler imaging to characterize in blood flow, or measurement of temperature as a function of changes in the speed of sound and attenuation properties. Grayscale US imaging has been shown to be a reliable technique to monitor delivery of cryoablative therapy, as the ice formed in the tissue is readily detected as a highly US-reflective surface. The utility of US as the monitoring and device guidance technique is to provide more accurate device placement, as well as limit the amount of expensive MR imaging time required to monitor long treatments (thermal ablation of tumors may be up to ninety minutes in duration). This procedure is demonstrated in FIGS. 24a and b and in the flowchart shown in FIG. 31.

Minimally invasive tissue ablation techniques have been presented in recent years for breast, brain prostate and liver therapy. Limited use for breast cancer ablation has been presented. No prior art has been presented involving a combined MRI detection and US guidance strategy for these therapies. MRI detection and MRI monitoring has been used for cryoablation and laser ablation of breast tumors, without US guidance and monitoring. Differing from the presented invention is a system developed by TxSonics Inc using MRI guidance to detect tumors and monitor therapy, and high-power US to ablate tumors. Only through a modification of the approaches taken in inventions thus far can an appropriate embodiment be realized. Only the use of US-guidance to monitor ablation therapies can decrease the expensive MRI time required to perform these procedures making them more economically appropriate. The preceding specific embodiments are illustrative of the practice of the present invention. It is to be understood that other embodiments known to those skilled in the art or disclosed herein may be employed without departing from the invention or the scope of the claims.

The practice of the invention as described above provides the following systems functions:

Technique for medial/lateral MR-guided delivery of needle to the breast using straight or angled needle trajectories.
Techniques for MR/US hybrid biopsy
Technique to co-register MR and US images
Reformatting of MR image to correspond to US image
Correction of US image for speed of sound variations
Correction of image co-registration errors
Registration of common anatomical features used to calculate co-registration accuracy
Delivery of a variety of needle gauge sizes as well as various minimally invasive treatment devices.
Positioning of multiple marking coils into the breast to define boundaries of lesions through a single incision.

According to the invention, the following functions are provided with minimal reconfiguration of the apparatus:

1) High quality breast images in bilateral screening and unilateral follow-up examinations using various MR coil configurations can be used for both procedures, and comprising an optimal breast compression strategy as well as optimizing access to the breast by the MR technician;

2) MR-guided localization, including medial or lateral biopsy, without prior knowledge of lesion location;

3) MR-guided multiple biopsy, including medial or lateral biopsy, with or without angulated needle approach;

4) MR-guided marker placement for improved surgical excision, under MR guidance, wherein a marker is positioned at the edges of the lesion as defined by MRI. The procedure would be similar to the MRI-guided biopsy procedure, however, a marker would be placed into the breast rather removing a sample of tissue. This may be conducted in conjunction with MR-guided biopsy, in conjunction with MR-guided needle localization.

5) MR-guided positioning of devices other than biopsy needles, including tissue investigation or ablation devices, such as invasive ultrasound tissue ablation devices, RF-heating applicators, cryoablative systems, miniature imaging coils, or optical photodynamic systems. According to the invention, monitoring of these devices may be done using the MR system to measure heating or cooling patterns during therapy. In the case of the optical systems, treatment region may be determined using other techniques (i.e. T2-weighted contrast sequences).

6) MR-US fusion imaging, wherein real-time US data can be used to position a device accurately into the lesion. This may be done using US exclusively when the lesion is visible on the US image, or using a combination of the MRI and US data fused using a variety of techniques. This strategy involves detecting the lesion using MRI, then removing the patient from the MR magnet room to perform US imaging. According to the invention, US imaging could involve a number of procedures a. US imaging—simple use of the US so as to identify the lesion and determine its malignancy status. Identification of the lesion in this manner could also act to provide lesion location and US properties with which the lesion may be identified for subsequent US-guided biopsy with the patient removed from the biopsy apparatus. Knowledge of the US features of the lesion could lead to easy identification of the lesion in a follow-up US examination. In cases where the lesion is difficult to identify in the US image, the option to view the lesion as a fusion image may assist in visualization.

b. Hybrid biopsy—this technique involves the use of the interventional US imaging membrane. This procedure requires stereotactic positioning of the US transducer in conjunction with free-hand delivery of the biopsy needle. This may be augmented by the use of a fused MR/US data set, and with or without the use of position-tracked US transducer and biopsy needle. Markers can be superimposed onto the MR/US fused dataset in such a way that the needle is easily identified on the MR/US fused image set, and in a way that the presented MR/US image updates to reflect the position of the US transducer.

c. Hybrid marker placement. Based on the procedure above, except that a MR and US-visible marker is implanted in the breast. This results in more accurate marker placement and reduces the amount of time spend in the MR-magnet room.

d. Hybrid treatment. The hybrid device delivery technique may also be used to deliver devices other than biopsy needles and marker placement devices such as tissue investigation or ablation devices. In this case it is advantageous to monitor the therapy using US. This offers the ability to improve the accuracy of the delivery and reduces the amount of time required for MR imaging. Again, this can be used with either the combined MR/US images, or using only the US images if the lesion can be confidently identified on the US image. The use of the fused MR/US data is beneficial when MRI provides better definition of tumor boundaries.

According to the invention, numerous techniques and methods can be used to enable the practice of the various embodiments of the invention, as illustrated by the following specific examples:

Stereotactic positioning of needle/US transducer based on MR coordinates:
 Specification to deliver needle in straight (e.g. medial-lateral) orientation.
 Specification of angulated needle delivery:
  ability to select shortest needle paths, or desired needle angle.
  ability to eliminate occluded areas behind fenestrated constraint plates ability to identify guide needle position on MR images to ensure that the chest wall will not be punctured during biopsy acquisition Specification of exact US transducer orientation and position, with Transducer mounted horizontally or vertically, under various constraints (minimal distance, selected orientation, etc.)

US transducer position tracking co-registered with breast frame of reference:

Ability to determine transducer frame of reference relative to breast frame of reference. This enables the device plane to correspond with the MRI coordinates.

Uses of tracking position of US imaging plane:

Calculating corresponding plane from 3D MR data set (creating virtual US image composed of reformatted MR data) will correspond to US image position and orientation.

distance to lesion through-plane will be determined and shown relative to virtual US image.

position of lesion center on US image will be identified.

MR data can be combined with the virtual US image to form a fused MR/US image.

Segmentation of MR lesion from contrast-enhanced data will be superimposed on the virtual US image to form a composite image.

Other auditory, tactile and visual cues may be used to guide free-hand US transducer movement, enabling the user to operate the system with or without a view of the US image.

Means of displaying position information about an interventional device:

a device's position may be tracked and an indication of its position superimposed over an acquired image (i.e. tracking a biopsy needle and superimposing an image of the device on the co-registered MR, US, or fused MR/US images.

Integration of images and position tracking data to validate US and MR image co-registration:

use of landmarks identified on US and MR images to confirm that the MR image is aligned with the US image use of image processing techniques and image acquisition techniques to better identify common landmarks on both imaging modalities. (i.e. breast parachymal patterns, vessels, cysts).

Method to quantify the similarity of two modalities. Means of presenting the result to the operator.

Means of correcting the registration between the two modalities:

Speed of sound correction.

Use the MRI data to determine composition of the breast, use known speed of sound values for the appropriate tissues and correct the US image.

Gradient warp shifts.

Correct for large errors due to gradient warp in the MR imaging system.

Position or registration error due to patient motion.

Relies on operator identification of similar features on both modalities. Once selected, the user may displace one image set to match the other, or may use automated image processing algorithms for this purpose.

As discussed herein, the benefits of the invention include, but are not limited to:

System that can be used for breast imaging and multiple intervention functions.

Improved access to the entire breast volume for imaging and intervention.

Improved breast immobilization through full compression of breast (including volume near chest wall).

Improved breast compression technique for operator ease of use.

Improved probe delivery using MRI guidance:

More accurate probe delivery—angled delivery provided greater access.

Multiple target sampling through a single incision point.

Flexibility in the selection of biopsy approach (medial or lateral) to minimize trauma to the breast Real-time US guided probe delivery through hybrid technique.

US guided sampling in the fringe field or even in another procedure room.

Flexibility in the selection of biopsy approach (medial or lateral) to minimize trauma to the breast and distance of breast tissue traversed for US imaging.

Ability to obtain many tissue samples through one small skin incision.

Ability to use standard interventional devices under US guidance, not limited to equipment that is MR compatible, thus reducing disposable equipment costs and permitting use of superior, non-MR-compatible devices.

Separation of MR imaging and biopsy procedure into two stages that can be performed in different locations using one dedicated transport stretcher, thus freeing the MR facility and its own dedicated patient transport stretcher for the next patient.

The foregoing description of the invention is not intended to describe every object, feature, advantage, and implementation of the present invention. While the description of the embodiments of the invention is focused on applications for breast imaging, it will be understood by those skilled in the art that the present invention has utility to applications elsewhere in the body. The primary differences would relate essentially to the geometry of the frames, which would hold the needle entry plate and the US plate.

All patents and printed publications referenced herein are hereby incorporated by reference into the specification hereof, each in its respective entirety.

We claim:

1. An apparatus for substantially immobilizing an anatomy of interest of a patient during MRI imaging of the anatomy of interest using a MRI scanner having a bore and during ultrasound imaging of the anatomy of interest, the apparatus comprising:

a patient support structure including a superior section and an inferior section, the inferior section being offset horizontally a distance from the superior section to define an opening therebetween, the inferior section connected to the superior section by a connection member lateral to the opening;

a transporter having a base and a pedestal, the pedestal supporting the patient support structure and the patient support structure horizontally translatable relative to the transporter between an extended and retracted position to allow the patient support structure to be positioned into the bore of the MRI scanner in the extended position, at least a portion of the opening extending beyond the pedestal in a horizontal direction providing medial, lateral and anterior access to the anatomy of interest in the retracted position;

an immobilization device coupled to the patient support structure, the immobilization device having a membrane support frame defining an open area and a deformable membrane configured to constrain the anatomy of interest within the opening in a selected position and conformation during both of a MRI imaging exam and an ultrasound imaging exam; and the deformable membrane being coupled to the membrane support frame and covering at least a portion of the open area, and the deformable membrane constructed from a non-magnetic and substantially ultrasound-transparent material, wherein a portion of the first deformable membrane is adjacent to the anatomy of interest when the anatomy of interest is constrained by the immobilization device.

2. The apparatus of claim 1, wherein the deformable membrane is of a thickness selected to allow puncturing or cutting of the deformable membrane by a standard medical instrument.

3. The apparatus of claim 1, further comprising a plurality of fiducial markers coupled to the immobilization device, wherein the fiducial markers are constructed from a material visible on images reconstructed from data acquired during the MRI imaging.

4. The apparatus of claim 1, wherein the immobilization device further comprises a second membrane support frame defining an open area and a second deformable membrane, wherein the membrane support frames are translatably positionable on opposite sides of a breast, and are configured to compress the breast by decreasing the distance between the membrane support frames, the second deformable membrane being coupled to the second membrane support frame and covering at least a portion of the open area and constructed from a non-magnetic and substantially ultrasound-transparent material.

5. The apparatus of claim 1, further comprising:
a mechanical stage coupled to the patient support structure; and
a holder coupled to the mechanical stage and configured for holding an ultrasound transducer, the mechanical stage and the holder being configured to provide a plurality of degrees of freedom for positioning the ultrasound transducer.

6. A method for MRI imaging and ultrasound imaging of an anatomy of interest in a patient, the method comprising the steps of:
positioning the patient on a patient support structure having a superior section and an inferior section defining an opening therebetween and connected by a connection member lateral to the opening, the patient support structure supported by a transporter and horizontally translatable relative to the transporter;
constraining the anatomy of interest in a fixed position and conformation using an immobilization device coupled to a patent support structure, the immobilization device having a membrane support frame defining an opening and a deformable membrane;
coupling the deformable membrane comprising a substantially ultrasound-transparent material to the membrane support frame, at least a portion of the deformable membrane covering the open area, a portion of the deformable membrane adjacent to the anatomy of interest;
horizontally translating the patient support structure to an extended position into a bore of a MRI scanner;
performing a MRI imaging exam on the anatomy of interest to acquire MRI imaging data;
horizontally translating the patient support structure to a retracted position, at least a portion of the opening horizontally extending beyond the transporter providing medial, lateral and anterior access to the anatomy of interest;
reconstructing and storing a MRI image from the MRI imaging data;
performing an ultrasound imaging exam on the anatomy of interest to acquire ultrasound imaging data through the deformable membrane; and
reconstructing and storing an ultrasound image from the ultrasound imaging data.

7. The method of claim 6, further comprising the step of deforming the deformable membrane to the anatomy of interest to increase an area of contact between the deformable membrane and the anatomy of interest.

8. The method of claim 6, further comprising the steps of:
determining a coordinate transformation between a reference frame corresponding to the MRI imaging exam and a reference frame corresponding to the ultrasound imaging exam.

9. The method of claim 8, wherein the step of determining the coordinate transformation comprises the steps of:
identifying on the image a known position on the immobilization device; and
determining an ultrasound transducer position and orientation relative to the known position.

10. The method of claim 8, wherein the step of determining a coordinate transformation comprises the step of identifying an anatomical landmark in both the MRI image and the ultrasound images.

11. The method of claim 8, wherein the image reconstructed from the MRI data is from the same plane and location as the ultrasound image.

12. The method of claim 11, further comprising the step of displaying the ultrasound image side-by-side with the MRI image on a display device.

13. The method of claim 11, further comprising the step of correlating the field of view for the ultrasound image and the MRI image.

14. The method of claim 11, further comprising the step of coregistering the MRI image and the ultrasound image to correct image errors.

15. The method of claim 11, further comprising the step of creating a fusion image from the ultrasound image and the MRI image.

16. The method of claim 8, further comprising the steps of:
identifying a location of interest in the MRI image; and
determining coordinates of the location of interest in the reference frame corresponding to the MRI imaging exam.

17. The method of claim 16, further comprising the step of:
using the coordinate transformation to position and orient the ultrasound transducer at a location and orientation such that a plane defined by the beam of the ultrasound transducer includes the location of interest.

18. The method of claim 16, further comprising the step of:
using the coordinate transformation to position and orient a medical instrument to target the location of interest.

19. The method of claim 18, further comprising the step of:
displaying the position and orientation of the medical instrument on the at least one of the MRI image and the ultrasound image.

20. The method of claim 19, wherein the medical instrument is a device for performing at least one of a biopsy, a marker placement, a cryotherapy treatment, an RF heating treatment, an invasive ultrasound tissue ablation, a local delivery of a chemotherapeutic agent, an optical ablation, and an optical photodynamic therapy.

21. The method of claim 9, wherein the step of determining the position and orientation of the ultrasound transducer relative to the known position comprises using a freehand tracking device coupled to the ultrasound transducer.

22. The method of claim 17, wherein the step of using the coordinate transformation to position and orient the ultrasound transducer at a location and orientation such that a plane defined by the beam of the ultrasound transducer includes the location of interest comprises using a freehand tracking device coupled to the ultrasound transducer.

* * * * *